United States Patent
Edwards, Jr. et al.

(10) Patent No.: US 10,857,216 B2
(45) Date of Patent: Dec. 8, 2020

(54) METHODS AND KITS FOR USE IN PREVENTING AND TREATING VULVOVAGINAL CANDIDIASIS

(71) Applicants: Los Angeles Biomedical Research Institute at Harbor-UCLA Medical Center, Torrance, CA (US); NovaDigm Therapeutics, Inc., Grand Forks, ND (US)

(72) Inventors: John E. Edwards, Jr., Palos Verdes Estates, CA (US); Scott G. Filler, Rancho Palos Verdes, CA (US); John P. Hennessey, Jr., Lower Gwynedd, PA (US); Michael Timothy Cooke, Brookline, MA (US); Jack D. Sobel, West Bloomfield, MO (US)

(73) Assignees: NovaDigm Therapeutics, Inc., Grand Forks, ND (US); Los Angeles Biomedical Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 16/081,062

(22) PCT Filed: Mar. 7, 2017

(86) PCT No.: PCT/US2017/021094
§ 371 (c)(1),
(2) Date: Aug. 30, 2018

(87) PCT Pub. No.: WO2017/155949
PCT Pub. Date: Sep. 14, 2017

(65) Prior Publication Data
US 2019/0076512 A1 Mar. 14, 2019

Related U.S. Application Data

(60) Provisional application No. 62/305,714, filed on Mar. 9, 2016.

(51) Int. Cl.
| | |
|---|---|
| *A61K 38/00* | (2006.01) |
| *A61K 38/02* | (2006.01) |
| *A61K 39/00* | (2006.01) |
| *A61K 38/16* | (2006.01) |
| *C07K 14/00* | (2006.01) |
| *A61K 33/08* | (2006.01) |
| *A61K 31/4196* | (2006.01) |
| *A61K 45/06* | (2006.01) |
| *A61K 31/00* | (2006.01) |

(52) U.S. Cl.
CPC .......... *A61K 39/0002* (2013.01); *A61K 31/00* (2013.01); *A61K 31/4196* (2013.01); *A61K 33/08* (2013.01); *A61K 38/168* (2013.01); *A61K 45/06* (2013.01); *C07K 14/00* (2013.01); *A61K 2039/55505* (2013.01); *A61K 2300/00* (2013.01)

(58) Field of Classification Search
USPC ........ 424/9.1, 9.2, 93.5, 184.1, 185.1, 274.1
See application file for complete search history.

(56) References Cited

U.S. PATENT DOCUMENTS

| | | | |
|---|---|---|---|
| 4,346,074 A | 8/1982 | Gilmour et al. | |
| 5,578,309 A | 11/1996 | Cutler et al. | |
| 5,622,939 A | 4/1997 | Jamas et al. | |
| 5,668,263 A | 9/1997 | Hoyer et al. | |
| 5,817,466 A | 10/1998 | Hoyer et al. | |
| 5,961,970 A | 10/1999 | Lowell et al. | |
| 6,248,329 B1 | 6/2001 | Chandrashekar et al. | |
| 6,703,025 B1 | 3/2004 | Patti et al. | |
| 6,747,137 B1 | 6/2004 | Weinstock et al. | |
| 7,067,138 B1 | 6/2006 | Edwards, Jr. et al. | |
| 7,241,613 B1 | 7/2007 | Willins et al. | |
| 7,250,286 B2 | 7/2007 | Ellison | |
| 7,666,438 B1 | 2/2010 | Patti et al. | |
| 7,732,187 B2 | 6/2010 | Cochran et al. | |
| 8,541,008 B2 | 9/2013 | Edwards, Jr. et al. | |
| 8,709,446 B2 | 4/2014 | Fu et al. | |
| 2002/0014643 A1 | 2/2002 | Kubo et al. | |
| 2002/0102262 A1 | 8/2002 | Hook et al. | |
| 2002/0146435 A1 | 10/2002 | Evans et al. | |
| 2003/0021737 A1 | 1/2003 | Tamhankar et al. | |
| 2003/0124134 A1 | 7/2003 | Edwards et al. | |
| 2003/0217373 A1 | 11/2003 | Green et al. | |
| 2004/0011638 A1 | 1/2004 | Lepizzera | |
| 2004/0017573 A1 | 1/2004 | Noe | |
| 2004/0116380 A1 | 6/2004 | Jamas et al. | |
| 2004/0175731 A1 | 9/2004 | Pier et al. | |
| 2005/0028714 A1 | 2/2005 | Hagen et al. | |
| 2005/0287146 A1 | 12/2005 | Patti et al. | |
| 2006/0083750 A1 | 4/2006 | Edwards et al. | |

(Continued)

FOREIGN PATENT DOCUMENTS

| | | |
|---|---|---|
| CN | 102574895 A | 7/2012 |
| EP | 2428800 A1 | 3/2012 |

(Continued)

OTHER PUBLICATIONS

Bailey et al., "The Candida albicans HYR1 gene, which is activated in response to hyphal development, belongs to a gene family encoding yeast cell wall proteins," J Bacteriol. 178(18):5353-60 (1996).

(Continued)

*Primary Examiner* — Rodney P Swartz
(74) *Attorney, Agent, or Firm* — Clark & Elbing LLP

(57) ABSTRACT

The invention features methods and kits use in for preventing and treating vulvovaginal candidiasis (VVC), in particular, recurrent VVC.

24 Claims, 25 Drawing Sheets
Specification includes a Sequence Listing.

(56) References Cited

U.S. PATENT DOCUMENTS

| | | |
|---|---|---|
| 2007/0007725 A1 | 1/2007 | Matilla et al. |
| 2007/0027309 A1 | 2/2007 | Weinstock et al. |
| 2007/0077256 A1 | 4/2007 | Edwards et al. |
| 2008/0311135 A1 | 12/2008 | Zheng et al. |
| 2009/0297562 A1 | 12/2009 | Edwards et al. |
| 2010/0001518 A1 | 1/2010 | Okada |
| 2010/0015094 A1 | 1/2010 | Babu et al. |
| 2010/0015095 A1 | 1/2010 | Pan et al. |
| 2010/0015182 A1 | 1/2010 | Lang et al. |
| 2010/0150942 A1 | 6/2010 | Cantor |
| 2010/0150956 A1 | 6/2010 | Patti et al. |
| 2012/0001499 A1 | 1/2012 | Makino et al. |
| 2012/0010731 A1 | 1/2012 | You |
| 2012/0014995 A1 | 1/2012 | Edwards, Jr. et al. |
| 2012/0023753 A1 | 2/2012 | Wen |
| 2012/0107316 A1 | 5/2012 | Cassone et al. |
| 2012/0237534 A1 | 9/2012 | Fu et al. |
| 2014/0033511 A1 | 2/2014 | Swahn et al. |
| 2014/0037689 A1 | 2/2014 | Edwards, Jr. et al. |
| 2014/0127217 A1 | 5/2014 | Edwards, Jr. et al. |
| 2014/0127218 A1 | 5/2014 | Edwards, Jr. et al. |
| 2014/0127243 A1 | 5/2014 | Edwards, Jr. et al. |
| 2014/0335114 A1 | 11/2014 | Fu et al. |
| 2015/0191514 A1 | 7/2015 | Ibrahim et al. |

FOREIGN PATENT DOCUMENTS

| | | |
|---|---|---|
| JP | 2007-512312 A | 5/2007 |
| JP | 2009-524601 A | 7/2009 |
| JP | 2012-530786 A | 12/2012 |
| JP | 2012-532114 A | 12/2012 |
| WO | WO-2005/049081 A1 | 6/2005 |
| WO | WO-2006/036817 A2 | 4/2006 |
| WO | WO-2006/059228 A2 | 6/2006 |
| WO | WO-2006/121895 A2 | 11/2006 |
| WO | WO-2007/081896 A2 | 7/2007 |
| WO | WO-2007/126813 A2 | 11/2007 |
| WO | WO-2010/151544 A1 | 12/2010 |
| WO | WO-2011/003085 A1 | 1/2011 |
| WO | WO-2012/163533 A1 | 12/2012 |
| WO | WO-2013/015831 A1 | 1/2013 |
| WO | WO-2014/144024 A1 | 9/2014 |
| WO | WO-2014/144211 A2 | 9/2014 |
| WO | WO-2014/144222 A2 | 9/2014 |
| WO | WO-2016/142660 A1 | 9/2016 |
| WO | WO-2017/155949 A1 | 9/2017 |

OTHER PUBLICATIONS

Barki et al., "Isolation of a Candida albicans DNA sequence conferring adhesion and aggregation on *Saccharomyces cerevisiae*," J Bacteriol. 175(17):5683-9 (1993).

Bates et al., "Candida albicans Iff11, a secreted protein required for cell wall structure and virulence," Infect Immun. 75(6):2922-8 (2007).

Bendel et al., "Distinct mechanisms of epithelial adhesion for Candida albicans and Candida tropicalis. Identification of the participating ligands and development of inhibitory peptides," J Clin Invest. 92(4):1840-9 (1993).

Bork, "Powers and pitfalls in sequence analysis: the 70% hurdle," Genome Research 10, 398-400, 2000.

Bowie et al., "Deciphering the message in protein sequences: tolerance to amino acid substitutions," Science. 247(4948):1306-10 (1990).

Caesar-TonThat et al., "A monoclonal antibody to Candida albicans enhances mouse neutrophil candidacidal activity," Infect Immun. 65(12):5354-7 (1997).

Campbell, General properties and applications of monoclonal antibodies, Monoclonal Antibody Technology. Elsevier Science Publishers, 1-32 (1984).

Cassone et al., "Recent progress in vaccines against fungal diseases," available in PMC Aug. 1, 2013, published in final edited form as: Curr Opin Microbiol. 15(4):427-433 (2012) (14 pages).

Castaldo et al., "Clinical spectrum of fungal infections after orthotopic liver transplantation," Arch Surg. 126(2):149-56 (1991).

Cheng et al, "Comparison between Candida albicans agglutinin-like sequence gene expression patterns in human clinical specimens and models of vaginal candidiasis, " Infect Immun. 73(3):1656-63 (2005).

Choi et al., "Acinetobacter baumannii invades epithelial cells and outer membrane protein a mediates interactions with epithelial cells," BMC Microbiol. 8:216 (2008) (11 pages).

Chowdhary et al., "Candida auris: A rapidly emerging cause of hospital-acquired multidrug-resistant fungal infections globally," PLoS Pathog. 13(5):e1006290 (2017) (10 pages).

Coleman et al., "Monoclonal antibodies specific for Candida albicans Als3 that immunolabel fungal cells in vitro and in vivo and block adhesion to host surfaces," available in PMC Jul. 1, 2010, published in final edited form as: J Microbiol Methods. 78(1):71-8 (2009) (19 pages).

Colman, "Effects of amino acid sequence changes on antibody-antigen interactions," Res Immunol. 145(1):33-6 (1994).

Communication from the Examining Division and Annex to the Communication issued in European Patent Application No. 11008862.2 dated Apr. 23, 2014 (6 pages).

Communication pursuant to Article 94(3) EPC for European Patent Application No. 07709622.0, dated Jun. 30, 2011 (4 pages).

Communication pursuant to Article 94(3) EPC for European Patent Application No. 07709622.0, dated Mar. 3, 2010 (6 pages).

Communication pursuant to Article 94(3) EPC for European Patent Application No. 07709622.0, dated Nov. 17, 2010 (12 pages).

Communication pursuant to Article 94(3) EPC for European Patent Application No. 10794828.3, dated May 19, 2014 (5 pages).

Communication pursuant to Article 94(3) EPC for European Patent Application No. 11008862.2, dated Apr. 23, 2014 (6 pages).

Communication pursuant to Article 94(3) EPC for European Patent Application No. 12001586.2, dated Apr. 23, 2014 (6 pages).

Communication pursuant to Article 94(3) EPC for European Patent Application No. 12001595.3, dated Apr. 23, 2014 (6 pages).

Communication pursuant to Article 94(3) EPC for European Patent Application No. 12817530.4, dated Jul. 6, 2017 (7 pages).

Communication pursuant to Article 94(3) EPC for European Patent Application No. 12817530.4, dated May 7, 2018 (7 pages).

Communication under Rule 71(3) EPC for European Patent Application No. 07709622.0, dated Jan. 27, 2012 (8 pages).

Cormack et al., "An adhesion of the yeast pathogen *Candida glabrata* mediating adherence to human epithelial cells," Science. 285(5427):578-82 (1999).

Cutler et al., "Characteristics of Candida albicans adherence to mouse tissues," Infect Immun. 58(6):1902-8 (1990).

De Bernardis et al., "Protective role of antimannan and anti-aspartyl proteinase antibodies in an experimental model of Candida albicans vaginitis in rats," Infect Immun. 65(8):3399-405 (1997).

Dromer et al., "Protection of mice against experimental cryptococcosis by anti-Cryptococcus neoformans monoclonal antibody," Infect Immun. 55(3):749-52 (1987).

EBI Accession No. GSP:AJF41554. Retrieved on Nov. 19, 2012 (1 page).

Ebi Accession No. GSP:ATC95389. Retrieved on Nov. 19, 2012 (1 page).

Edwards, "Fungal cell wall vaccines: an update," J Med Microbiol. 61(Pt 7):895-903 (2012).

Ekenna et al., "Natural history of bloodstream infections in a burn patient population: the importance of candidemia," Am J Infect Control. 21(4):189-95 (1993).

Ellis, Vaccines, Chapter 29—New technologies for Making Vaccines, Plotkin et al., eds., W.B. Saunders Company (Philadelphia), pp. 568-575 (1988) (9 pages).

English Language Translation of Notice of Final Rejection issued in Japanese Patent Application No. 2008-549598, dated Feb. 21, 2013, dated Feb. 25, 2013 (5 pages).

English Language Translation of Notice of Reasons for Rejection issued in Japanese Patent Application No. 2008-549598, dated Mar. 15, 2012, dated Mar. 21, 2012 (9 pages).

(56) References Cited

OTHER PUBLICATIONS

English Translation of Official Communication for Japanese Patent Application No. 2008-510281, dated Dec. 12, 2011 (3 pages).
Examination Report for Indian Patent Application No. 1302/DELNP/2014, dated Sep. 26, 2018 (7 pages).
Examination Report for New Zealand Patent Application No. 597442, dated Jul. 18, 2012 (2 pages).
Examiner's First Report for Australian Patent Application No. 2006244401, dated Nov. 25, 2010 (1 page).
Examiner's Report for Canadian Patent Application No. 2,607,176, dated Nov. 26, 2012 (3 pages).
Examiner's Report for Canadian Patent Application No. 2,636,277, dated Dec. 4, 2012 (5 pages).
Examiner's Report for Canadian Patent Application No. 2636277, dated May 13, 2014 (2 pages).
Extended European Search Report for European Application No. 06752341.5, dated Nov. 13, 2009 (15 pages).
Extended European Search Report for European Application No. 12817530.4, dated Dec. 18, 2014 (7 pages).
Extended European Search Report for European Patent Application No. 07709622.0, dated Nov. 19, 2009 (9 pages).
Extended European Search Report for European Patent Application No. 10794828.3, dated Nov. 30, 2012 (9 pages).
Extended European Search Report for European Patent Application No. 11008862.2, dated Feb. 10, 2012 (10 pages).
Extended European Search Report for European Patent Application No. 12001586.2, dated Nov. 13, 2012 (14 pages).
Extended European Search Report for European Patent Application No. 12001595.3, dated Nov. 13, 2012 (12 pages).
Extended European Search Report for European Patent Application No. 12832321.9, dated Jun. 3, 2015 (9 pages).
Extended European Search Report for European Patent Application No. 18166876.5, dated Jul. 31, 2018 (10 pages).
Filler, "Candida-host cell receptor-ligand interactions," Curr Opin Microbiol. 9(4):333-9 (2006).
Final Japanese Office Action for Japanese Patent Application No. 2008-510281, dated Oct. 26, 2012 (3 pages).
Final Japanese Office Action for Japanese Patent Application No. 2008-549598, dated Feb. 25, 2013 (5 pages).
Final Japanese Office Action for Japanese Patent Application No. 2012-207831, dated Dec. 16, 2014 (10 pages).
Final Office Action for U.S. Appl. No. 14/034,216, dated Mar. 30, 2016 (28 pages).
Finks et al., "Vancomycin-resistant *Staphylococcus aureus*, Michigan, USA, 2007" Emerg Infect Dis. 15(6):943-945 (2009).
First Examiner's Report issued in Australian Patent Application No. 2007205065, dated Jan. 18, 2012 (2 pages).
First Office Action for Chinese Patent Application No. 201080039446.5, dated May 31, 2013 (English language Translation Provided) (11 pages).
First Office Action for Chinese Patent Application No. 201280046321.4, dated Jan. 19, 2015 (20 pages, English language translation provided).
First Office Action for Chinese Patent Application No. 201280056018.2, dated Mar. 14, 2016 (English language translation provided) (27 pages).
First Office Action for Chinese Patent Application No. 201280056018.2, dated Mar. 14, 2016 (27 pages) (English language translation provided).
Fisher-Hoch et al., "Opportunistic candidiasis: an epidemic of the 1980's," Clin Infect Dis. 21(4):897-904 (1995).
Fonzi et al., "Isogenic strain construction and gene mapping in Candida albicans," Genetics. 134(3):717-28 (1993).
Fu et al., "Candida albicans Als1p: an adhesin that is a downstream effector of the EFG1 filamentation pathway," Mol Microbiol. 44(1):61-72 (2002).
Fu et al., "Cloning and characterization of a gene (LIP1) which encodes a lipase from the pathogenic yeast *Candida albicans*," Microbiology. 143(Pt 2):331-40 (1997).

Fu et al., "Cloning and characterization of CAD1/AAF1, a gene from Candida albicans that induces adherence to endothelial cells after expression in *Saccharomyces cerevisiae*," Infect Immun. 66(5):2078-84 (1998).
Fu et al., "Expression of the Candida albicans Gene ALS1 in *Saccharomyces cerevisiae* Induces Adherence to Endothelial and Epithelial Cells," Infect Immun. 66(4):1783-6 (1998).
Gale et al., "Cloning and expression of a gene encoding an integrin-like protein in Candida albicans," Proc Nat Acad Sci USA. 93(1):357-61 (1996).
Gale et al., "Linkage of adhesion, filamentous growth, and virulence in Candida albicans to a single gene, INT1," Science. 279(5355):1355-8 (1998).
Gaur et al., "Expression, cloning, and characterization of a Candida albicans gene, ALA1, that confers adherence properties upon *Saccharomyces cerevisiae* for extracellular matrix proteins," Infect Immun. 65(12):5289-94 (1997).
GenBank AAO72958.1. Retrieved on Jan. 6, 2016 (2 pages.).
Gietz et al., "Studies on the transformation of intact yeast cells by the LiAc/SS-DNA/PEG procedure," Yeast. 11(4):355-60 (1995).
Greenspan et al., "Defining epitopes: Its not as easy as it seems," Nat Biotechnol. 17(10):936-7 (1999).
Gustafson et al., "Molecular mimicry in Candida albicans. Role of an integrin analogue in adhesion of the yeast to human endothelium," J Clin Invest. 87(6):1896-902 (1991).
Han et al., "Antibody response that protects against disseminated candidiasis," Infect Immun. 63(7):2714-9 (1995).
Hasenclever et al., "Antigenic relationships of Torulopsis glabrata and seven species of the genus *Candida*," J Bacteriol. 79:677-81 (1960).
Hoyer et al., "Candida albicans ALS1: domains related to a *Saccharomyces cerevisiae* sexual agglutinin separated by a repeating motif," Mol Microbiol. 15(1):39-54 (1995).
Hoyer et al., "Candida albicans ALS3 and insights into the nature of the ALS gene family," Curr Genet. 33(6):451-9 (1998).
Hoyer et al., "Characterization of agglutinin-like sequence genes from non-albicans Candida and phylogenetic analysis of the ALS family," Genetics. 157(4):1555-67 (2001).
Hoyer et al., "Detection of Als proteins on the cell wall of Candida albicans in murine tissues," Infect Immun. 67(8):4251-55 (1999).
Hoyer et al., "Identification of Candida albicans ALS2 and ALS4 and localization of Als proteins to the fungal cell surface," J Bacteriol. 180(20):5334-43 (1998).
Hoyer, "The ALS gene family of Candida albicans," Trends Microbiol. 9(4):176-80 (2001).
Ibrahim et al., "Evidence implicating phospholipase as a virulence factor of Candida albicans," Infect Immun. 63(5):1993-8 (1995).
Ibrahim et al., "NDV-3 protects mice from vulvovaginal candidiasis through T- and B-cell immune response," Vaccine. 31(47):5549-56 (2013) (10 pages).
Ibrahim et al., "The anti-Candida vaccine based on the recombinant N-terminal domain of Als1p is broadly active against disseminated candidiasis," Infect Immun. 74(5):3039-41 (2006).
Ibrahim et al., "Vaccination with recombinant N-terminal domain of Als1p improves survival during murine disseminated candidiasis by enhancing cell-mediated, not humoral, immunity," Infect Immun. 73(2):999-1005 (2005).
Illustrated Stedman's Medical Dictionary, 24th Edition. Williams and Wilkins, London. p. 707 (1982).
Inhibitex reports favorable results from aurexis phase II trial for the treatment of staph bloodstream infections. Inhibitex Inc. (2005) (Accessed Sep. 19, 2005) (5 pages).
International Preliminary Report on Patentability for International Application No. PCT/US2006/017482, dated Nov. 6, 2007 (4 pages).
International Preliminary Report on Patentability for International Application No. PCT/US2007/000433, dated Jul. 8, 2008 (5 pages).
International Preliminary Report on Patentability for International Application No. PCT/US2010/040949, dated Jan. 4, 2012 (5 pages).
International Preliminary Report on Patentability for International Application No. PCT/US2017/021094, dated Sep. 11, 2018 (10 pages).

(56) References Cited

OTHER PUBLICATIONS

International Preliminary Report on Patentability for International Patent Application No. PCT/US2012/055604, dated Mar. 18, 2014 (11 pages).
International Preliminary Report on Patentability for International Patent Application No. PCT/US2012/000328, dated Jan. 28, 2014 (6 pages).
International Preliminary Report on Patentability for International Patent Application No. PCT/US2014/028256, dated Sep. 15, 2015 (7 pages).
International Preliminary Report on Patentability for International Patent Application No. PCT/US2014/028521, dated Oct. 13, 2015 (11 pages).
International Preliminary Report on Patentability for International Patent Application No. PCT/US2014/028535, dated Sep. 15, 2015 (7 pages).
International Search Report for International Application No. PCT/US17/21094, dated Jul. 7, 2017 (5 pages).
International Search Report for International Application No. PCT/US2006/017482, dated Mar. 19, 2007 (2 pages).
International Search Report for International Application No. PCT/US2010/040949, dated Jun. 6, 2011 (3 pages).
International Search Report for International Application No. PCT/US2018/026889, dated Jul. 11, 2018 (4 pages).
International Search Report for International Patent Application No. PCT/US07/00433, dated Oct. 1, 2007 (1 page).
International Search Report for International Patent Application No. PCT/US12/55604, dated Mar. 8, 2013 (9 pages).
International Search Report for International Patent Application No. PCT/US14/28256, dated Aug. 18, 2014 (4 pages).
International Search Report for International Patent Application No. PCT/US14/28521, dated Nov. 13, 2014 (7 pages).
International Search Report for International Patent Application No. PCT/US2014/28535, dated Oct. 24, 2014 (5 pages).
International Search Report for International Application No. PCT/US12/00328, dated Dec. 18, 2012 (3 pages).
Invitation pursuant to Article 94(3) and Rule 71(1) EPC for European Patent Application No. 10794828.3, dated Sep. 21, 2015 (3 pages).
Jaffe et al., "Culture of human endothelial cells derived from umbilical veins. Identification by morphologic and immunologic criteria," J Clin Invest. 52(11):2745-56 (1973).
Japanese Inquiry Rejection for Japanese Patent Application No. 2008-549598, dated Mar. 7, 2014 (13 pages).
Japanese Office Action for Japanese Patent Application No. 2014-105980, dated Apr. 24, 2015 (2 pages).
Jarvis et al., "Predominant pathogens in hospital infections," J Antimicrob Chemother. 29 (Suppl A): 19-24 (1992) (Abstract only) (2 pages).
Jimenez-Lucho et al., "Cryptococcus neoformans, Candida albicans, and other fungi bind specifically to the glycosphingolipid lactosylceramide (Gal beta 1-4Glc beta 1-1Cer), a possible adhesion receptor for yeasts," Infect Immun. 58(7):2085-90 (1990).
Jones et al., "Molecular cloning of a second form of rac protein kinase," Cell Regul. 2(12):1001-9 (1991).
Kaur et al., "Strategies to reduce mortality in adult and neonatal Candidemia in developing countries," J Fungi (Basel). 3(3):pii:E41 (2017) (20 pages).
Kim et al., "Partial characterization of leukocyte binding molecules on endothelial cells induced by minimally oxidized LDL," Arterioscler Thromb. 14(3):427-33 (1994).
Klein, "Role of cell surface molecules of Blastomyces dermatitidis in the pathogenesis and immunobiology of blastomycosis," Semin Respir Infect. 12(3):198-205 (1997).
Klotz et al., "Effect of an arginine-glycine-aspartic acid-containing peptide on hematogenous candidal infections in rabbits," Antimicrob Agents Chemother. 36(1):132-6 (1992).
Kramer et al., "How long do nosocomial pathogens persist on inanimate surfaces? A systematic review," BMC Infect Dis. 6:130 (2006) (8 pages).

Larkin et al., "The Emerging Pathogen *Candida auris*: Growth Phenotype, Virulence Factors, Activity of Antifungals, and Effect of SCY-078, a Novel Glucan Synthesis Inhibitor, on Growth Morphology and Biofilm Formation," Antimicrob Agents Chemother. 61(5). pii: e02396-16 (2017) (13 pages).
Liang et al., "Prediction of antigenic epitopes on protein surfaces by consensus scoring," BMC Bioinformatics 10:302 (2009) (10 pages).
Lin et al., "Acinetobacter baumannii rOmpA vaccine dose alters immune polarization and immunodominant epitopes," available in PMC Jan. 2, 2014, published in final edited form as: Vaccine. 31(2):313-8 (2013) (14 pages).
Lipke et al., "AG alpha 1 is the structural gene for the *Saccharomyces cerevisiae* alpha-agglutinin, a cell surface glycoprotein involved in cell-cell interactions during mating," Mol Cell Biol. 9(8):3155-65 (1989).
Liu et al., "INH-A21 contains antibodies specific for the Candida ALS protein family," 44th ICAAC, Oct. 30-Nov. 2, Washington D.C . . . p. 425, Abstract M-1144 (2004).
Lotter et al., "Identification of an epitope on the Entamoeba histolytica 170-kD lectin conferring antibody-mediated protection against invasive amebiasis," J Exp Med. 185(10):1793-801 (1997).
Loza et al., "Functional Analysis of the Candida albicans ALS1 Gene Product," Yeast. 21(6):473-82 (2004).
Luo et al., "Active and passive immunization with rHyr1p-N protects mice against hematogenously disseminated candidiasis," PloS One. 6(10):e25909 (2011) (8 pages).
Luo et al., "Candida albicans Hyr1p. confers resistance to neutrophil killing and is a potential vaccine target," J Infect Dis. 201(11):1718-28 (2010) (11 pages).
Mamo et al., "Protection induced in mice vaccinated with recombinant collagen-binding protein (CnBP) and alpha-toxoid against intramammary infection with *Staphylococcus aureus*," Microbiol Immunol. 44(5):381-4 (2000).
Mamo et al., "Vaccination against *Staphylococcus aureus* mastitis: immunological response of mice vaccinated with fibronectin-binding protein (FnBP-A) to challenge with *S. aureus*," Vaccine. 12(11):988-92 (1994).
Mamo et al., "Vaccination with *Staphylococcus aureus* fibrinogen binding proteins (FgBPs) reduces colonisation of *S. aureus* in a mouse mastitis model," FEMS Immonol Med Microbiol. 10(1):47-53 (1994).
Manjarrez-Hernandez et al., "Binding of diarrheagenic *Escherichia coli* to 32- to 33-kilodalton human intestinal brush border proteins," Infect Immun. 65(11):4494-501 (1997).
Mayer et al., "Candida albicans adherence to endothelial cells," Microvasc Res. 43(2):218-26 (1992).
Mayer et al., "Recognition of binding sites on Candida albicans by monoclonal antibodies to human leukocyte antigens," Infect Immun. 58(11):3765-9 (1990).
Miller et al., "Immunity against *Staphylococcus aureus* cutaneous infections," Nat Rev Immunol. 11(8):505-18 (2011).
Mukherjee et al., "Protective murine monoclonal antibodies to Cryptococcus neoformans," Infect Immun. 60(11):4534-41 (1992).
NCBI Blast for Accession No. YP_001084998. Retrieved on Nov. 27, 2012 (2 pages).
Nilsson et al., "Vaccination with a Recombinant Fragment of Collagen Adhesin Provides Protection against *Staphylococcus aureus*-mediated Septic Death," J Clin Invest. 101(12):2640-9 (1998).
Notice of Allowance for U.S. Appl. No. 14/034,300, dated Mar. 30, 2016 (10 pages).
Notice of Reasons for Rejection for Japanese Patent Application No. 2008-549598, dated Mar. 21, 2012 (15 pages).
Notice of Reasons for Rejection for Japanese Patent Application No. 2012-207831, dated Nov. 22, 2013 (15 pages).
Notice of Reasons for Rejection for Japanese Patent Application No. 2014-521610, dated Apr. 20, 2016 (11 pages) (English language translation provided).
Notice of Reasons for Rejection for Japanese Patent Application No. 2015-018131, dated Mar. 16, 2016 (9 pages) (English language translation provided).
Notification of Reason for Rejection for Japanese Patent Application No. 2014-105980, dated Feb. 9, 2016 (13 pages) (English language translation provided).

(56) References Cited

OTHER PUBLICATIONS

Notification of the First Office Action for Chinese Patent Application No. 2012800463214, dated Jan. 19, 2015 (English language translation included) (20 pages).
Office Action for Eurasian Patent Application No. 201391199/28, dated Sep. 20, 2015 (1 page, no English language translation provided).
Office Action for European Patent Application No. 07709622.0, dated Jan. 27, 2012 (8 pages).
Office Action for Georgian Patent Application No. 13225/01, dated Sep. 23, 2015 (1 page, no English language translation provided).
Office Action for Georgian Patent Application No. 13226/01, dated Feb. 9, 2015 (2 pages, English language translation provided).
Office Action for Russian Patent Application No. 2012103502, dated May 21, 2014 (English translation provided) (6 pages).
Office Action for Russian Patent Application No. 2012103502, dated Oct. 14, 2014 (English language translation provided) (5 pages).
Office Action for Ukrainian Patent Application No. a 2013 10981, dated Nov. 13, 2015 (6 pages) (English translation provided).
Office Action for Ukrainian Patent Application No. a 2013 10982, dated Jan. 15, 2016 (6 pages) (no English language translation provided).
Oh et al., "Functional specificity of Candida albicans Als3p proteins and clade specificity of ALS3 alleles discriminated by the number of copies of the tandem repeat sequence in the central domain," Microbiology. 151(Pt 3):673-81 (2005).
Opal et al., "Systemic host responses in severe sepsis analyzed by causative microorganism and treatment effects of drotrecogin alfa (activated)," Clin Infect Dis. 37(1):50-8 (2003).
Palaszynski et al., "Systemic immunization with conserved pilus-associated adhesins protects against mucosal infections," Dev Biol Stand. 92:117-22 (1998).
Panaretou et al., Isolation of yeast plasma membranes. Methods in Molecular Biology, vol. 53: Yeast Protocols. I.H. Evans, 117-21 (1996).
Patent Examination Report No. 1 for Australian Patent Application No. 2010266114, dated Dec. 31, 2014 (3 pages).
Patent Examination Report No. 2 for Australian Patent Application No. 2006244401, dated Aug. 21, 2012 (3 pages).
Patent Examination Report No. 2 for Australian Patent Application No. 2007205065, dated Mar. 12, 2013 (3 pages).
Patent Examination Report No. 3 for Australian Patent Application No. 2007205065, dated Oct. 15, 2013 (3 pages).
Patent Examination Report No. 1 for Australian Patent Application No. 2013203750, dated Aug. 20, 2014 (4 pages).
Patti et al., "MSCRAMM-mediated adherence of microorganisms to host tissues," Annu Rev Microbiol. 48:585-617 (1994).
Patti, "Vaccines and immunotherapy for staphylococcal infections," Int J Artif Organs. 28(11):1157-62 (2005).
Peleg et al., "Prokaryote-eukaryote interactions identified by using Caenorhabditis elegans," Proc Natl Acad Sci USA. 105(38):14585-90 (2008).
Perraut et al., "Successful treatment of Candida albicans endophthalmitis with intravitreal amphotericin B," Arch Opthalmol. 99(9):1565-7 (1981).
Pfaller et al., "National surveillance of nosocomial blood stream infection due to species of Candida other than Candida albicans: frequency of occurrence and antifungal susceptibility in the SCOPE Program. SCOPE Participant Group. Surveillance and Control of Pathogens of Epidemiologic," Diagn Microbiol Infect Dis. 30(2):121-9 (1998).
Pietrella et al., "A beta-glucan-conjugate vaccine and anti-beta-glucan antibodies are effective against murine vaginal candidiasis as assessed by a novel in vivo imaging technique," Vaccine. 28(7):1717-25 (2010).
Polak, "Combination therapy of experimental candidiasis, cryptococcosis, aspergillosis and wangiellosis in mice," Chemotherapy. 33(5):381-95 (1987).

Prasadarao et al., "Identification and characterization of S fimbria-binding sialoglycoproteins on brain microvascular endothelial cells," Infect Immun. 65(7):2852-60 (1997).
Rieg et al., "Unanticipated heterogeneity in growth rate and virulence among Candida albicans AAF1 null mutants," Infect Immun. 67(7):3193-8 (1999).
Rotrosen et al., "Adherence of Candida to cultured vascular endothelial cells: mechanisms of attachment and endothelial cell penetration," J Infect Dis. 152(6):1264-74 (1985).
Rudinger, "Characteristics of the amino acids as components of a peptide hormone sequence," in Peptide Hormones, Parsons, ed., University Park Press, Jun. 1976, pp. 1-7.
Sanford et al., "Passive immunization against Cryptococcus neoformans with an isotype-switch family of monoclonal antibodies reactive with cryptococcal polysaccharide," Infect Immun. 58(6):1919-23 (1990).
Sanger et al., "A rapid method for determining sequences in DNA by primed synthesis with DNA polymerase," J Mol Biol. 94(3):441-8 (1975).
Santoni, "Intravaginal and intranasal immunizations confer equal protection against Candida in experimental vaginitis," Abstracts of the General Meeting of the American Society for Microbiology 101:367-8 (2001) (3 pages).
Saporito-Irwin et al., "PHR1, a pH-regulated gene of Candida albicans, is required for morphogenesis," Mol Cell Biol. 15(2):601-13 (1995).
Schmidt et al., "NDV-3, a recombinant alum-adjuvanted vaccine for Candida and Staphylococcus aureus is safe and immunogenic in healthy adults," available in PMC Dec. 14, 2013, published in final edited form as: Vaccine. 30(52):7594-600 (2012) (18 pages).
Schnaar, "Isolation of glycosphingolipids," Methods Enzymol. 230:348-70 (1994).
Search Information Statement for Australian Patent Application No. 2006244401, dated Nov. 24, 2010 (3 pages).
Search Report for Eurasian Patent Application No. 201591808/26, dated Mar. 23, 2016 (3 pages) (no English language translation provided).
Second Office Action for Chinese Patent Application No. 201080039446. 5, dated Nov. 18, 2013 (English language translation provided) (7 pages).
Second Office Action for Chinese Patent Application No. 201280046321. 4, dated Oct. 26, 2015 (14 pages, English language translation provided).
Segal et al.,"Protection against systemic infections with various Candida species elicited by vaccination with Candida albicans ribosomes," Sabouraudia. 23(4):275-85 (1985).
Sheppard et al., "Functional and structural diversity in the Als protein family of Candida albicans," J Biol Chem. 279(29):30480-9 (2004).
Sherry et al., "Biofilm-forming capability of highly virulent, multidrug-resistant Candida auris," Emerg Infect Dis. 23(2):328-331 (2017).
Sheth et al., "Development of an anti-adhesive vaccine for Pseudomonas aeruginosa targeting the c-terminal region of the pilin structural protein," Biomed Pept Proteins Nucleic Acids. 1(3):141-8 (1995).
Smith et al., "New insights into Acinetobacter baumannii pathogenesis revealed by high-density pyrosequencing and transposon mutagenesis," Genes Dev. 21(5):601-14 (2007).
Soares et al.,"2-DE analysis indicates that Acinetobacter baumannii displays a robust and versatile metabolism," Proteome Sci. 7:37 (2009) (10 pages).
Sobel et al., "Maintenance fluconazole therapy for recurrent vulvovaginal candidiasis," N Engl J Med. 351(9):876-83 (2004).
Spellberg et al., "Current treatment strategies for disseminated candidiasis," Clin Infect Dis 42(2):244-51 (2006).
Spellberg et al., "Efficacy of the anti-Candida rAls3p-N or rAls1p-N vaccines against disseminated and mucosal candidiasis," J Infect Dis. 194(2):256-60 (2006).
Spellberg et al., "Mice with disseminated candidiasis die of progressive sepsis," J Infect Dis. 192(2):336-43 (2005).
Spellberg et al., "Parenchymal organ, and not splenic, immunity correlates with host survival during disseminated candidiasis," Infect Immun. 71(10):5756-64 (2003).

(56) References Cited

OTHER PUBLICATIONS

Spellberg et al., "The antifungal vaccine derived from the recombinant N terminus of Als3p protects mice against the bacterium *Staphylococcus aureus*," Infect Immun. 76(10):4574-80 (2008).
Spellberg et al., "The pathophysiology and treatment of Candida sepsis," Curr Infect Dis Rep. 4(5):387-99 (2002).
Stuehler et al.,"Cross-protective TH1 immunity against Aspergillus fumigatus and Candida albicans," Blood. 117(22):5881-91 (2011).
Sui et al., "The vaccines and antibodies associated with Als3p for treatment of Candida albicans infections," Vaccine 35(43):5786-5793 (2017).
Summons to attend oral proceedings pursuant to Rule 115(1) EPC for European Patent Application No. 11008862.2, dated Oct. 20, 2015 (6 pages).
Summons to attend oral proceedings pursuant to Rule 115(1) EPC for European Patent Application No. 12001586.2, dated Oct. 19, 2015 (7 pages).
Sundstrom, "Adhesion in *Candida* spp.," Cell Microbiol. 4(8):461-9 (2002).
Torosantucci et al., "Protection by Anti-Beta-Glucan Antibodies is Associated with Restricted Beta-1,3 Glucan Binding Specificity and Inhibition of Fungal Growth and Adherence," PLoS ONE 4(4):e5392 (2009) (17 Pages).
Translation of Cited Reference 2: Today's Therapy 2004, Igaku-Shoin Ltd, p. 166 from Japanese Application No. 2012-207831 (5 pages).
Translation of Cited Reference 3: Today's Therapy 2002, Igaku-Shoin Ltd., p. 155-156 from Japanese Application No. 2012-207831 (5 pages).
Tsay et al., "Approach to the Investigation and Management of Patients With Candida auris, an Emerging Multidrug-Resistant Yeast," Clin Infect Dis. 66(2):306-311 (2018).
Uniprot Submission P46591. Nov. 1995. <http://www.uniprot.org/uniprotIP46591.txt?version=39> Retrieved Sep. 16, 2010 (2 pages).
Von Eiff et al., "Distribution of capsular and surface polysaccharide serotypes of *Staphylococcus aureus*," Diagn Microbiol Infect Dis. 58(3): 297-302 (2007).
Wang et al., "Vaccines in the treatment of invasive candidiasis," Virulence 6(4):309-315 (2015).
Webster's II New Riverside University Dictionary, The Riversdie Publishing Company, p. 933, 1984 (2 pages).
Wenzel et al., "*Candida* species: emerging hospital bloodstream pathogens [editoral]," Infect Control Hosp Epidermiol. 12(9):523-4 (1991).
Wey et al., "Hospital-acquired candidemia. The attributable mortality and excess length of stay," Arch Intern Med. 148(12):2642-5 (1988).
Wisplinghoff et al., "Nosocomial bloodstream infections in US hospitals: analysis of 24,179 cases from a prospective nationwide surveillance study," Clin Infect Dis. 39(3):309-17 (2004).
Wojciechowicz et al., "Cell surface anchorage and ligand-binding domains of the *Saccharomyces cerevisiae* cell adhesion protein alpha-agglutinin, a member of the immunoglobulin superfamily," Mol Cell Biol. 13(4):2554-63 (1993).
Written Opinion of the International Searching Authority for International Application No. PCT/US17/21094, dated Jul. 7, 2017 (9 pages).
Written Opinion of the International Searching Authority for International Application No. PCT/US2006/017482, dated Mar. 19, 2007 (3 pages).
Written Opinion of the International Searching Authority for International Application No. PCT/US2007/000433, dated Oct. 1, 2007 (4 pages).
Written Opinion of the International Searching Authority for International Application No. PCT/US2010/040949, dated Jun. 6, 2011 (4 pages).
Written Opinion of the International Searching Authority for International Application No. PCT/US2012/00328, dated Dec. 18, 2012 (5 pages).
Written Opinion of the International Searching Authority for International Application No. PCT/US2018/026889, dated Jul. 11, 2018 (13 pages).
Written Opinion of the International Searching Authority for International Patent Application No. PCT/US12/55604, dated Mar. 8, 2013 (10 pages).
Written Opinion of the International Searching Authority for International Patent Application No. PCT/US2014/028256, dated Aug. 18, 2014 (6 pages).
Written Opinion of the International Searching Authority for International Patent Application No. PCT/US2014/028521, dated Nov. 13, 2014 (10 pages).
Written Opinion of the International Searching Authority for International Patent Application No. PCT/US2014/028535, dated Oct. 24, 2014 (6 pages).
Xiong et al., "New Approaches to the Prevention and Treatment of Severe *S. aureus* Infections," Drugs Today (Barc). 36(8):529-39 (2000).
Yan et al., "Hemoglobin-induced binding of Candida albicans to the cell-binding domain of fibronectin is independent of the Arg-Gly-Asp sequence," Infect Immun. 66(5):1904-9 (1998).
Yeaman et al., "Mechanisms of NDV-3 vaccine efficacy in MRSA skin versus invasive infection," Proc Natl Acad Sci USA. 111(51):E5555-63 (2014).
Zhang et al., "Crystal Structure of Glutathione-Dependent Phospholipid Peroxidase Hyr1 from the Yeast *Saccharamyces cerevisiae*," Proteins. 73(4):1058-62 (2008).
Zhao et al., "Allelic variation in the contiguous loci encoding Candida albicans ALS5, ALS1 and ALS9," Microbiology. 149(Pt 10):2947-60 (2003).
Zhao et al., "ALS3 and ALS8 represent a single locus that encodes a Candida albicans adhesin; functional comparisons between Als3p and Als1p," Microbiology. 150(Pt 7):2415-28 (2004).
Zhao et al., "Analysis of the candida albicans Als2p and Als4p adhesins suggests the potential for compensatory function within the Als family," Microbiology. 151(Pt 5):1619-30 (2005).
Extended European Search Report for European Patent Application No. 17763871.5, dated Feb. 11, 2020 (9 pages).
"Vulvovaginal candidiasis," 2015 Sexually Transmitted Diseases Treatment Guidelines, Centers for Disease Control and Prevention, <www.cdc.gov/std/tg2015/candidiasis.htm> retrieved on Jan. 22, 2020, page last reviewed Jun. 4, 2015 (4 pages).

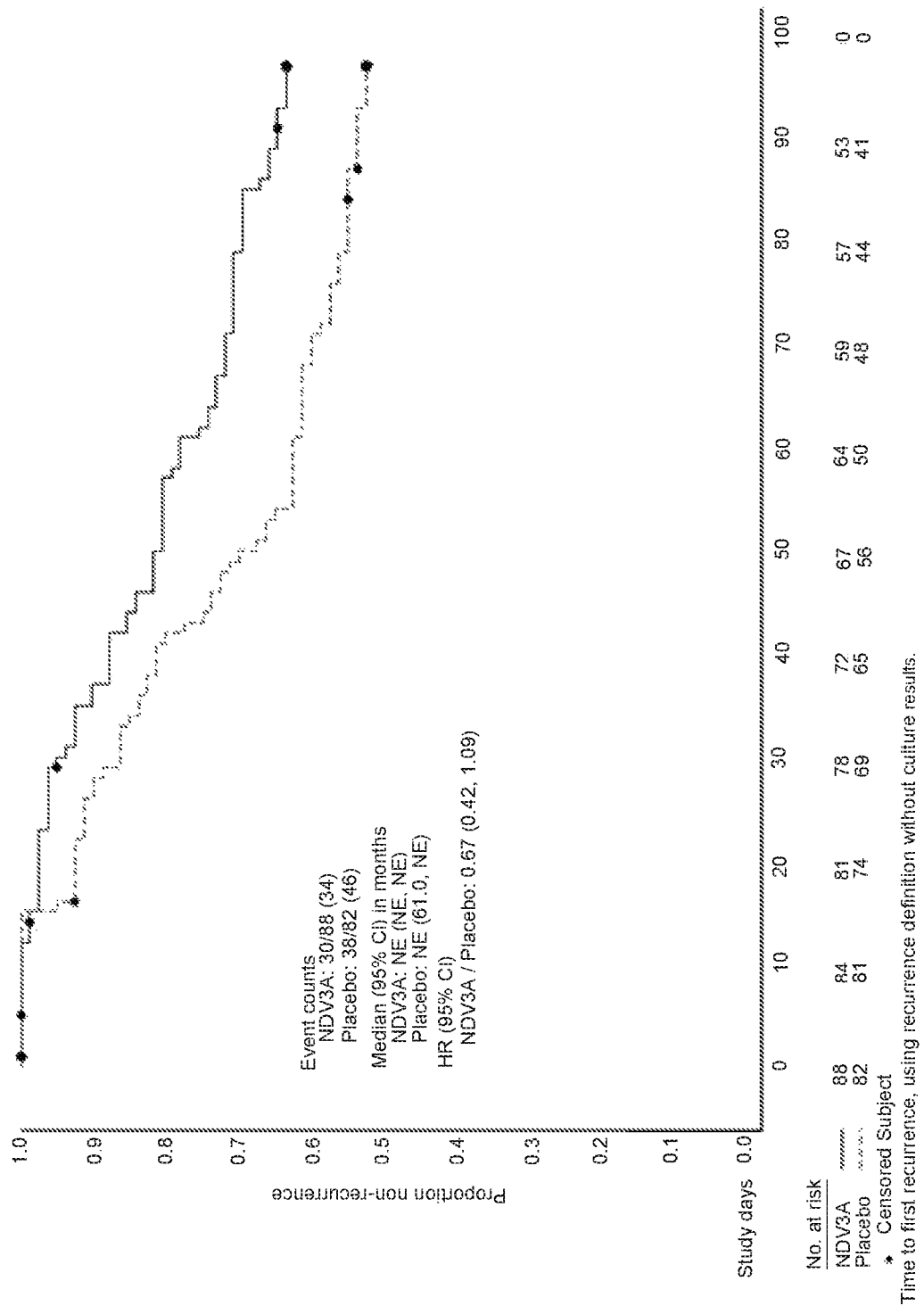

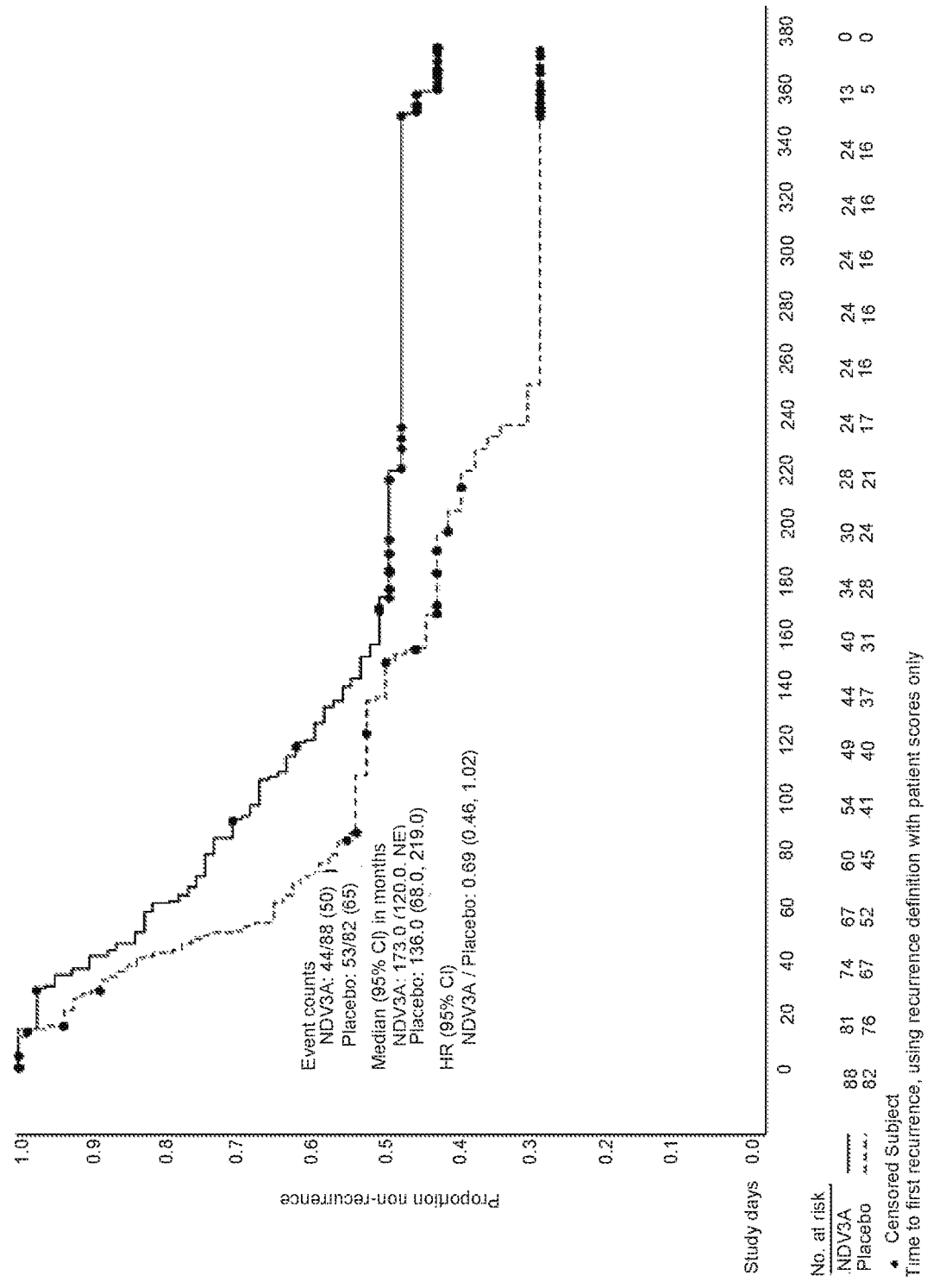

Recurrence definition with culture result.

Recurrence definition without culture result.

Recurrence definition using patient scores only.

Recurrence definition using patient scores only.

METHODS AND KITS FOR USE IN PREVENTING AND TREATING VULVOVAGINAL CANDIDIASIS

FIELD OF THE INVENTION

In general, this invention relates to methods and kits for use in for preventing and treating vulvovaginal candidiasis.

BACKGROUND OF THE INVENTION

Of the many causes of vaginal infections, vulvovaginal candidiasis (VVC) is among the most common, accounting for an estimated 17% to 39% of symptomatic women (Anderson et al. (2004), JAMA 291(11):1368-1379). Recurrent vulvovaginal candidiasis (RVVC) remains a common problem worldwide, affecting all strata of society. RVVC, generally defined as four or more episodes of VVC every year (Centers for Disease Control MMWR Recommendation and Reports 2015, 64(3): 77), is estimated to occur in 5 to 8% of women during their reproductive years Spinillo et al. (1993), Obst Gynecol 81(5 Pt1)):721-727). The majority of women with RVVC have no recognizable risk factors (Spinillo et al. (1992), J Reprod Med 37(4):343-347; Sobel (2002), Curr Infect Dis Rep 4(6):514-519). Symptomatic vulvovaginitis results in considerable suffering and cost and has a markedly negative effect on sexual well-being and relations (Foxman et al. (2000), Sex Transm Dis 27(4):230-235).

Diagnosis and treatment of vulvovaginal candidiasis, together with lost productivity, result in an estimated cost of US $1 billion per year in the United States (Foxman et al. (2000), supra). Vulvovaginal candidiasis is the second most common cause of vaginal infections, after bacterial vaginitis (Fleury (1981), Clin Obstet Gynecol 24 (2):407-438).

*C. albicans*, responsible for the majority of symptomatic episodes of VVC, can include a set of symptoms ranging from asymptomatic colonization to severe symptomatic infection (Sobel et al. (1998), Am J Obstet Gynecol 178(2): 203-211). Two elements are important in the development of symptomatic VVC. First, vaginal colonization, which can occur through several different sources including local spread from the perineum and gastrointestinal tract, digital introduction, and sexual transmission, must be established. Secondly, transformation must occur that results in a change from an asymptomatic to a symptomatic state (Nyirjesy (2008), Infect Dis Clin North Am 22(4):637-652). Recurrent VVC may be the result of a persistent strain of *C. albicans* or the introduction of a new strain of *C. albicans* or other species (Vazquez et al. (1994), *J Infect Dis* 170(6):1566-1569).

Current treatment consists mostly of azole medications (e.g., butoconazole, fluconazole, miconazole, terconazole, and tioconazole) which inhibit fungal cell wall metabolism. Although maintenance fluconazole therapy is prescribed for RVVC, a long term cure remains difficult to find. In a recent study reported by Sobel et al. ((2004) *N Engl J Med* 351(9):876-883), the median time to clinical recurrence in the fluconazole group was 10.2 months, as compared with 4 months in the placebo group.

Thus, there exists a need for effective methods to treat and prevent VVC, including RVVC. The present invention satisfies these needs and provides related advantages as well.

SUMMARY OF THE INVENTION

The invention provides methods for use in preventing and treating vulvovaginal candidiasis (VVC), including recurrent VVC (RVVC).

Accordingly, in a first aspect, the invention provides methods including the steps of: (a) administering to a subject (e.g., a human female) having vulvovaginal candidiasis (VVC; e.g., recurrent VVC (RVVC)) an effective amount of an antifungal agent (e.g., fluconazole, by oral administration of an amount ranging from 100 mg to 200 mg, e.g., 150 mg); and (b) administering an immunogenic amount of an Als3 polypeptide (e.g., Als3-1 (SEQ ID NO: 3), e.g., as part of NDV-3, or Als3-2 (SEQ ID NO: 2), e.g., as part of NDV-3A) to the subject, to reduce VVC in the subject. In various embodiments, the immunogenic amount of the Als3 polypeptide is administered subsequent (e.g., 7 days to 21 days, or 14 days, subsequent) to administration of the antifungal agent.

The methods of the invention also include, optionally, administration of a second dose of antifungal agent about 2 to about 4 days after administration of the antifungal agent of step (a). The methods also include the optional administration of a third dose of the antifungal agent about 2 to about 4 days after administration of the second dose of the antifungal agent.

The Als3 polypeptide administered according to the methods of the invention can have, for example, at least 80% identity (e.g., at least 85%, 90%, 95%, 97%, 99%, or 100% identity) to Als3-2, Als3-1, Als3, Als3 (18-324), or Als3 (Ser/Thr rich sequence).

The amount of Als3 polypeptide administered in the methods of the invention may be, for example, 5 to 500 micrograms, e.g., 10 to 200 micrograms, 20 to 100 micrograms, 30 to 90 micrograms, or 40 to 80 micrograms, or about 300 micrograms. In various examples, about 100 to 300 micrograms, 150 to 200 micrograms, 200 to 250 micrograms, or 250 to 300 micrograms of the Als3 polypeptide is administered to a subject in a single-dose primary regimen. In other examples, about 5 to 60 micrograms, 10 to 50 micrograms, 20 to 40 micrograms, or 30 micrograms of the Als3 polypeptide is administered to a subject in a multi-dose primary regimen.

The methods of the invention also can include the administration of one or more booster doses of an Als3 polypeptide.

Further, the methods of the invention include the optional administration, after step (b), of an effective amount of an antifungal agent to the subject. In these methods, the antifungal agent can optionally be administered about 5 to about 8 days, or about 13 to about 15 days, after administration of the Als3 polypeptide.

The Als3 polypeptide can be administered in the methods of the invention in the form of a vaccine composition including the Als3 polypeptide and an adjuvant such as, for example, an aluminum compound (e.g., aluminum hydroxide). In other embodiments, the Als3 polypeptide can be administered in the methods of the invention in the form of a vaccine composition including the Als3 polypeptide but without an adjuvant.

In a second aspect, the invention provides kits that include (a) an antifungal agent (e.g., fluconazole); and (b) an Als3 polypeptide (e.g., an Als3 polypeptide having at least 80% identity (e.g., at least 85%, 90%, 95%, 97%, 99%, or 100% identity) to Als3-2, Als3-1, Als3, Als3 (18-324), or Als3 (Ser/Thr rich sequence)). The antifungal agent and/or the Als3 polypeptide may be formulated in compositions that include, or lack, an adjuvant.

In a third aspect, the invention provides methods of treating a subject at risk of developing recurrent VVC (RVVC), including administering to the subject a therapeutically effective amount of an Als3 polypeptide, to reduce recurrences of VVC in the subject, wherein the effective amount is at least 5.0 micrograms of the Als3 polypeptide. The therapeutically effective amount of Als3 polypeptide administered can thus be, for example, about 5 micrograms to about 1000 micrograms, about 5 micrograms to about 500 micrograms, about 10 micrograms to about 300 micrograms, about 20 micrograms to about 100 micrograms, about 30 micrograms to about 90 micrograms, about 40 micrograms to about 80 micrograms, or about 300 micrograms. Further, the Als3 polypeptide can have, for example, at least 80% identity (e.g., at least 85%, 90%, 95%, 97%, 99%, or 100% identity) to Als3-2, Als3-1, Als3, Als3 (18-324), or Als3 (Ser/Thr rich sequence). These methods can also include the optional administration of one or more booster doses of an Als3 polypeptide. Furthermore, the subject may not have a current diagnosis of VVC; may not be experiencing a current episode of VVC; or may not have a VVC Sign and Symptom Composite Questionnaire Score of ≥3 at the time of the administering (see Appendix 1: VVC Sign and Symptom Composite Questionnaire). Further, the subject may have previously had a diagnosis of VVC or recurrent VVC.

In the methods of the invention, the antifungal agent and/or the Als3 polypeptide may be formulated in compositions that include, or lack, an adjuvant.

In all aspects of the invention, the subject is a female human subject. In all aspects of the invention, the antifungal agent may be one selected from an azole (e.g., a triazole, such as fluconazole, albaconazole, efinaconazole, epoxiconazole, isavuconazole, itraconazole, posaconazole, propiconazole, ravuconazole, terconazole, and voriconazole; an imidazole, such as bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, and tioconazole; and a thiazole, such as abafungin), a polyene (e.g., amphotericin B, candicidin, filipin, hamycin, natamycin, nystatin, and rimocidin), an allylamine (e.g., amorolfin, butenafine, naftifine, and terbinafine), an echinocandin (e.g., anidulafungin, biafungin (e.g., CD101), caspofungin, and micafungin), lanosterol demethylase inhibitors (e.g., VT-1161), and other antifungal agents, including, but not limited to, benzoic acid, ciclopirox oamine, enfumafungin (e.g., SCY-078), 5-flucytosin, griseofulvin, haloprogin, tolnaftate, aminocandin, chlordantoin, chlorphenesin, nifuroxime, undecylenic acid, and crystal violet, and pharmaceutically acceptable salts or esters thereof. In particular, the antifungal agent is fluconazole.

By "adjuvant" is meant one or more substances that cause stimulation of the immune system. In this context, an adjuvant is used to enhance an immune response to one or more vaccine antigens (e.g., one or more of the Als3 polypeptides described herein). An adjuvant may be administered to a subject before, in combination with, or after administration of a vaccine. Examples of chemical compounds used as adjuvants include, but are not limited to, aluminum compounds (e.g., alum, aluminum hydroxide, Alhydrogel), oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, and co-stimulatory factors.

By "antigen" is meant a molecule to which an antibody can selectively bind. The target antigen may be a protein (e.g., an antigenic peptide), carbohydrate, nucleic acid, lipid, hapten, or other naturally occurring or synthetic compound. The target antigen may also be a polypeptide or peptide mimic. An antigen may also be administered to an animal to generate an immune response in the animal.

By "carrier" in the context of a conjugate is meant a moiety or particle, e.g., KLH, CRM197, tetanus toxoid, a phage, a yeast, a virus, a virosome, or a recombinant virus-like particle, that is suitable for being linked to or displaying a polypeptide as described herein.

By "chimeric vaccine" is meant a vaccine that includes at least two distinct antigens, e.g., joined covalently. An example of a chimeric vaccine is a composition that includes a polypeptide displayed, e.g., on the surface of a particle such as a phage, virus, yeast, virosome, or recombinant virus-like particle.

By "conjugate" is meant a compound that includes a polypeptide of the invention linked to another moiety or particle, e.g., KLH, CRM197, tetanus toxoid, a phage, a yeast, a virus, a virosome, or a recombinant virus-like particle.

By "conservative substitution" in an amino acid sequence is meant replacement of an amino acid for another within a family of amino acids that are related in the chemical nature of their side chains.

Genetically encoded amino acids can be divided into four families: acidic (aspartate, glutamate); basic (lysine, arginine, histidine); nonpolar (alanine, valine, leucine, isoleucine, proline, phenylalanine, methionine, tryptophan); and uncharged polar (glycine, asparagine, glutamine, cysteine, serine, threonine, tyrosine). Phenylalanine, tryptophan, and tyrosine are sometimes grouped as aromatic amino acids. In similar fashion, the amino acids can also be separated into the following groups: acidic (aspartate, glutamate); basic (lysine, arginine, histidine); alipathic (glycine, alanine, valine, leucine, isoleucine, serine, threonine), with serine and threonine optionally grouped separately as alipathic-hydroxyl; aromatic (phenylalanine, tyrosine, tryptophan); amide (asparagine, glutamine); and sulfur-containing (cysteine, methionine).

Whether a change in the amino acid sequence results in a functional variant can be determined by assessing the ability of the variant polypeptide to function in a fashion similar to the wild-type polypeptide using standard methods such as those described herein.

By "effective amount" is meant the amount of a pharmaceutical composition required to achieve a desired clinical response, whether in a single or multiple doses. An effective amount of a pharmaceutical composition used to practice the methods described herein varies depending upon the manner of administration, the age, body weight, and general health of the subject. Ultimately, the prescribers will decide the appropriate amount and dosage regimen.

By "flanking amino acid" is meant an amino acid in a polypeptide sequence that is immediately adjacent to the N- or C-terminus of a particular defined sequence. Desirably, a flanking amino acid is present on the N- and/or C-terminus of the amino acid sequence of SEQ ID NO: 1, 2, 3, 4, or 5 or a fragment thereof; and more desirably, 1, 2, 3, 4, 5, 6, 7, 8, 9, or 10 flanking amino acids are present at the N- and/or C-terminus of the amino acid sequence of SEQ ID NO: 1, 2, 3, 4, or 5, or a fragment thereof.

By "fusion protein" is meant a protein that includes a polypeptide of the invention, e.g., a peptide fragment or variant, and a fusion partner.

By "fusion partner" is meant a sequence that can be fused to a polypeptide or peptide of the invention. Examples of fusion partners include heterologous sequences such as detection markers, stabilizing domains, sequences that aid in production or purification of the protein, or domains that increase the antigenicity of the polypeptide. In other examples, fusion partners include Als3 N-terminal signal sequences that are either not cleaved from the portion of the pre-protein with which they are naturally contiguous, in the case of Als3 polypeptides including N-terminal sequences of mature Als3, or Als3 N-terminal signal sequences fused to N-terminal sequences of Als3 polypeptides that do not include naturally occurring N-terminal sequences of mature Als3. One example of such an N-terminal signal sequence is as follows: MLQQYTLLLIYLSVATA (SEQ ID NO: 6). Variants of this sequence, as defined herein, are also included in the invention.

By "Als3 polypeptide" is meant, in general, a polypeptide having the amino acid sequence of SEQ ID NO: 1, 2, 3, 4, or 5. In some instances, an Als3 protein has substantial identity to SEQ ID NO:1, 2, 3, 4, or 5.

By "immunogenic" is meant any substance that is capable of inducing an immune response in a subject.

By "immunogenic amount" in the context of a vaccine is meant an amount of the vaccine required to induce an immune response in a subject in a clinically relevant manner. An immunogenic amount of vaccine used to practice the methods of vaccination as described herein varies depending upon the manner of administration, the age, body weight, and general health of the subject. Ultimately, the prescribers will decide the appropriate amount and dosage regimen.

By "isolated" or "purified" is meant separated from other naturally accompanying components. Typically, a compound (e.g., nucleic acid, polypeptide, antibody, or small molecule) is substantially isolated when it is at least 60%, by weight, free from the proteins and/or naturally occurring organic molecules with which it is naturally associated. The definition also extends, e.g., to a polypeptide or nucleic acid molecule separated from its flanking sequences (e.g., for an amino acid sequence, isolated refers to a sequence that is free from the flanking amino acids with which the sequence is naturally associated in a polypeptide). In some instances, the compound is at least 75%, more preferably at least 90%, and most preferably at least 99%, by weight, isolated. An isolated compound, e.g., polypeptide, may be obtained by standard techniques, for example, by extraction from a natural source (e.g., purification from a cell infected with *Candida*); by expression of a recombinant nucleic acid encoding an Als3 or CNA fragment or variant, or a fusion protein thereof; or by chemically synthesizing the polypeptide. Purity can be measured by any appropriate method, e.g., by column chromatography, polyacrylamide gel electrophoresis, or HPLC analysis.

By "linked to" or "conjugated to" in the context of a conjugate is meant a covalent or non-covalent interaction between the polypeptide and the carrier or fusion partner. Non-covalent interactions include, but are not limited to, hydrogen bonding, ionic interactions among charged groups, electrostatic binding, van der Waals interactions, hydrophobic interactions among non-polar groups, lipophobic interactions, and Log P-based attractions.

By "patient" or "subject" is meant a mammal, including, but not limited to, a human or non-human mammal, such as a bovine, equine, canine, ovine, or feline. In particular, the subject is a female.

The terms "peptide," "polypeptide," and "protein" are used interchangeably and refer to any chain of two or more natural or unnatural amino acids, regardless of post-translational modification (e.g., glycosylation or phosphorylation), constituting all or part of a naturally-occurring or non-naturally occurring polypeptide or peptide, as is described herein.

As used herein, a natural amino acid is a natural α-amino acid having the L-configuration, such as those normally occurring in natural polypeptides. Unnatural amino acid refers to an amino acid that normally does not occur in polypeptides, e.g., an epimer of a natural α-amino acid having the L configuration, that is to say an amino acid having the unnatural D-configuration; or a (D,L)-isomeric mixture thereof; or a homolog of such an amino acid, for example, a β-amino acid, an α,α-disubstituted amino acid, or an α-amino acid wherein the amino acid side chain has been shortened by one or two methylene groups or lengthened to up to 10 carbon atoms, such as an α-amino alkanoic acid with 5 up to and including 10 carbon atoms in a linear chain, an unsubstituted or substituted aromatic (α-aryl or α-aryl lower alkyl), for example, a substituted phenylalanine or phenylglycine.

The terms "pharmaceutically acceptable carrier" and "pharmaceutically acceptable excipient" are used interchangeably and mean a carrier or excipient that is physiologically acceptable to the treated patient while retaining the therapeutic properties of the compound with which it is administered. One exemplary pharmaceutically acceptable carrier substance is physiological saline. Other physiologically acceptable carriers and their formulations are known to those skilled in the art and described, for example, in Remington's Pharmaceutical Sciences, ($20^{th}$ edition), ed. A. Gennaro, 2000, Lippincott, Williams & Wilkins, Philadelphia, Pa.

By "pharmaceutical composition" is meant a composition containing a polypeptide, conjugate, vaccine, or antifungal agent of the invention, formulated with a pharmaceutically acceptable excipient, and manufactured or sold with the approval of a governmental regulatory agency as part of a therapeutic regimen for the treatment or prevention of a disease or event in a mammal. Pharmaceutical compositions can be formulated, for example, for intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

By "recurrent vulvovaginal candidiasis," or RVVC, is meant a vulvovaginal candidiasis (VVC) infection in a subject (e.g., a human female) that is characterized by the occurrence of at least two (e.g., at least three or four or more) specific episodes of infection in one year or characterized by at least one (e.g., at least two or three or more) episode of infection that is unrelated to antibiotic therapy that occurs within one year. Such subjects may have had, for example, one, two, three, or more VVC infections during the past 12 months prior to treatment. Further, at the time of treatment, these subjects may not have a current diagnosis of VVC, and/or may not be experiencing a current episode of VVC. Further, at the time of treatment, these patients may not have a VVC Sign and Symptom Composite Questionnaire Score of ≥3 at the time (see below).

By "substantially identical" is meant an amino acid sequence or nucleic acid sequence that exhibits at least 50% identity to a reference sequence. Such a sequence is generally at least, e.g., 50%, 60%, 70%, 75%, 80%, 85%, 90%, 95%, 96%, 97%, 98%, or 99% identical at the amino acid level or nucleic acid level to a reference sequence. In general, for polypeptides, the length of comparison sequences can be at least five amino acids, e.g., 10, 20, 30, 40, 50, 60, 70, 80, 90, 100, 125, 150, 175, 200, 250, 300, 400, 500, 600, 700, 800, 900, 1000, 1100, or more amino acids, up to the entire length of the polypeptide (see, e.g., SEQ ID NOs: 1, 2, 3, 4, and 5). For nucleic acids, the length of comparison sequences can generally be at least 10, 20, 30, 40, 50, 60, 70, 80, 90, 100, 125, 150, 175, 200, 250, 300, 400, 500, 600, 700, 800, 900, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., J. Mol. Biol. 147:195-7, 1981) and BLAST (Basic Local Alignment Search Tool; Altschul et al., J. Mol. Biol. 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus™ (Schwarz and Dayhof, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared.

By "treating" or "treatment" is meant the medical management of a patient with the intent to cure, ameliorate, stabilize, reduce the likelihood of, or prevent a disease, pathological condition, disorder, or event, by administering a pharmaceutical composition. This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief of symptoms rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

By "vaccine," as used herein, is meant a composition that elicits an immune response in a subject to which it is administered.

By "vaccinate," as used herein, is meant to treat a patient by administering a vaccine, e.g., to prevent or ameliorate a disease, pathological condition, disorder, or event.

By "variant" in the context of a polypeptide or portion thereof as described herein, or a nucleic acid molecule encoding same, is meant to include substitutions or alterations in the amino acid sequence or nucleic acid sequence, e.g., resulting in a substantially identical sequence. A polypeptide having a variant sequence may maintain at least one biological activity of the original polypeptide, e.g., immunogenic activity. The term "variant" includes, e.g., amino acid insertional derivatives such as amino and/or carboxyl-terminal fusions, as well as intrasequence insertions of single or multiple amino acids. Insertional amino acid variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue inserted in its place. Where the protein is derivatized by amino acid substitution, amino acids are generally replaced by conservative substitutions, e.g., other amino acids having similar physical chemical properties such as hydrophobicity, hydrophilicity, electronegativity, bulky sidechains and the like.

For purposes of the present invention, variants also include single or multiple substitutions, deletions and/or additions of any component(s) naturally or artificially associated with the portion of a naturally occurring protein from which the polypeptide may be derived, such as carbohydrate, lipid and/or other proteinaceous moieties. All such molecules are encompassed by the term "variant."

By "variant sequence" is meant the amino acid or nucleic acid sequence of a variant as defined herein.

Other features and advantages of the invention will be apparent from the detailed description, the drawings, and the claims.

BRIEF DESCRIPTION OF THE DRAWINGS

FIG. 1A is a graph showing total IgG titers. FIG. 1B is a graph showing total IgA1 titers FIG. 2A is a graph showing total IgG antibody titers. FIG. 2B is a graph showing total IgA1 antibody titers.

FIG. 3A is a graph showing Als3-stimulated IFN-γ production. FIG. 3B is a graph showing Als3-stimulated IL-17A production.

FIG. 4A is a graph showing Als3-stimulated IFN-γ production. FIG. 4B is a graph showing Als3-stimulated IL-17A production.

FIG. 5A is a graph showing percentage of subjects responding with IFN-γ-producing PBMCs. FIG. 5B is a graph showing percentage of subjects responding with IL-17A-producing PBMCs.

FIG. 6A shows serum IgG titers, FIG. 6B shows vaginal IgG titers, FIG. 6C shows plasma IgA titers, and FIG. 6D shows vaginal wash IgA titers. The 300 µg with alum (black triangles) has 2-3 fold higher antibody responses than the same dose without alum (black squares). The 30 µg dose administered intradermally (gray diamonds)

showed a similar antibody response to the same dose delivered intramuscularly (with alum). Placebo controls are indicated with black circles.

Figure 7A:
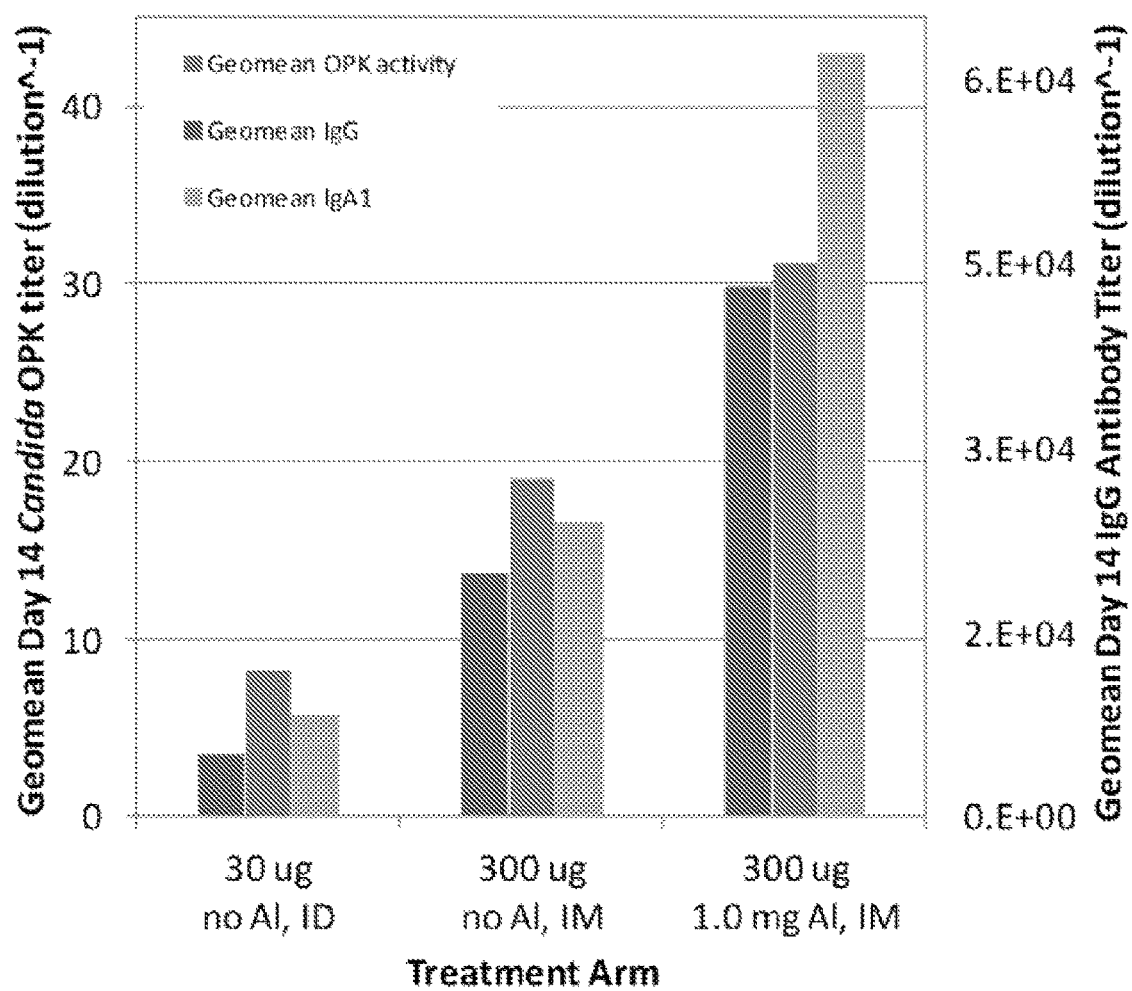
Figure 7B:
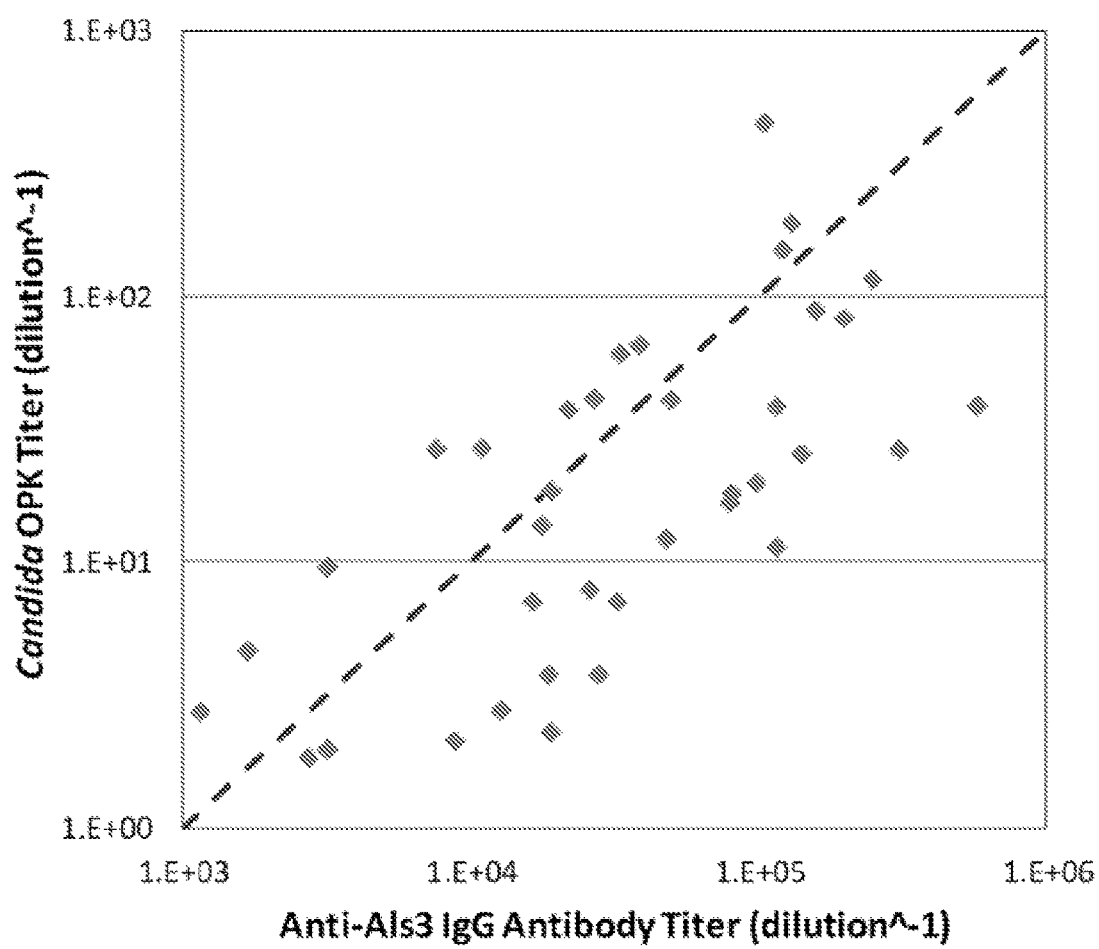

FIGS. 7A and 7B are graphs showing association between plasma anti-Als3 total IgG and IgA1 titers and *C. albicans* opsonophagocytic killing (OPK) activity. FIG. 7A shows the geomean anti-Als3 antibody titer and *C. albicans* OPK activity by treatment group. FIG. 7B shows the *C. albicans* OPK titer versus anti-Als3 IgG plasma antibody titer for day 14 post-vaccination samples.

Figure 8A:
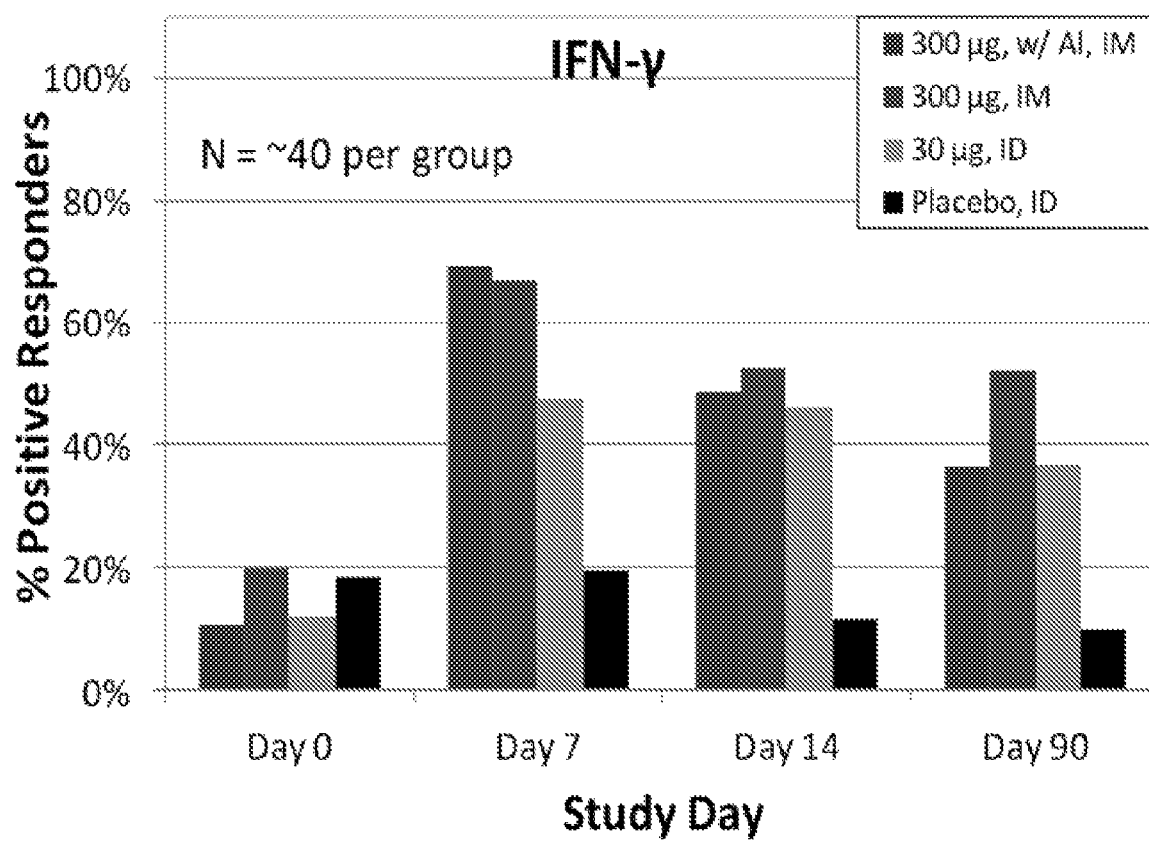
Figure 8B:
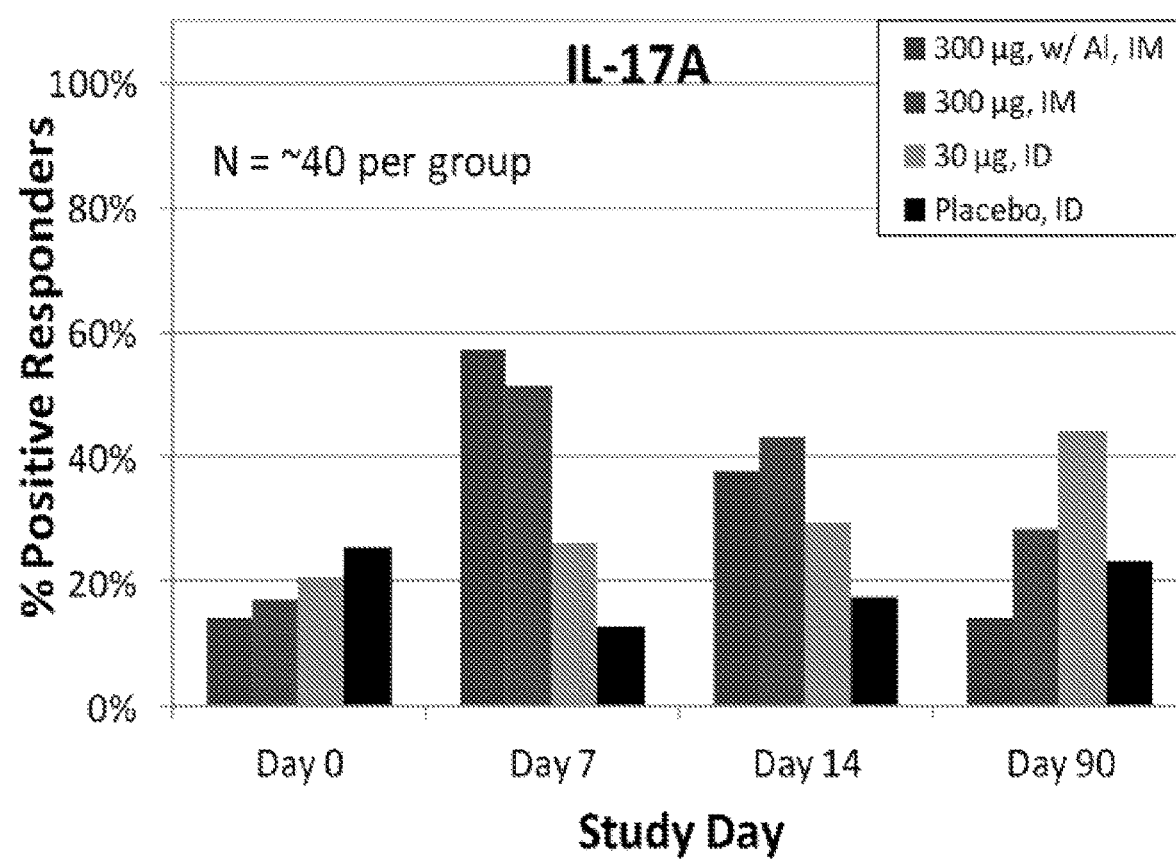

FIGS. 8A and 8B are graphs showing Th1 (FIG. 8A) and Th17 (FIG. 8B) T-cell stimulation by the Als3 antigen. The 300 µg intramuscular dose with or without alum produce similar responses, while the 30 µg intradermal injection produced a reduced, but overall similar response.

Figure 9:
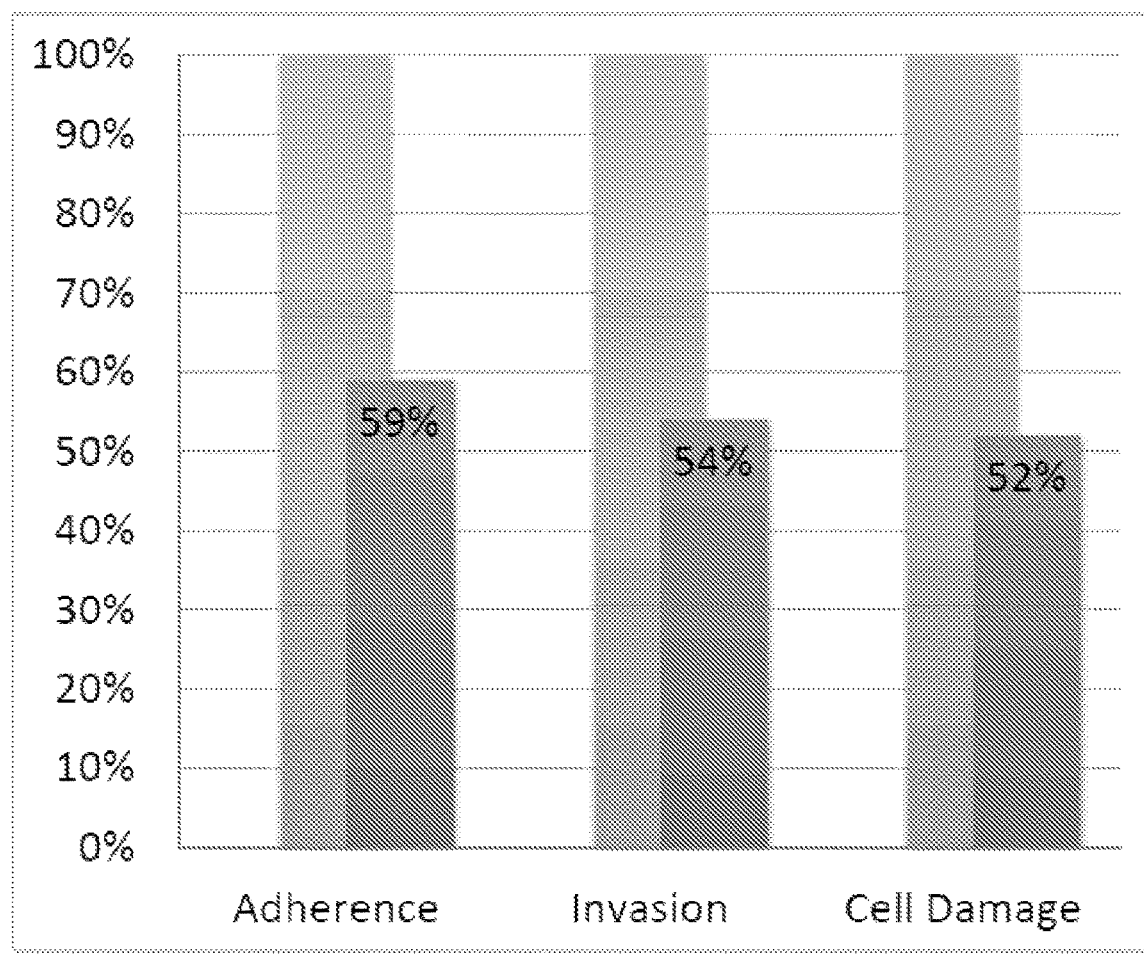

FIG. 9 is a graph comparing post-vaccination sera (light gray bars) to pre-vaccination sera (dark gray bars, normalized to 100%) of each individual administered the Als3 antigen.

Figure 10:
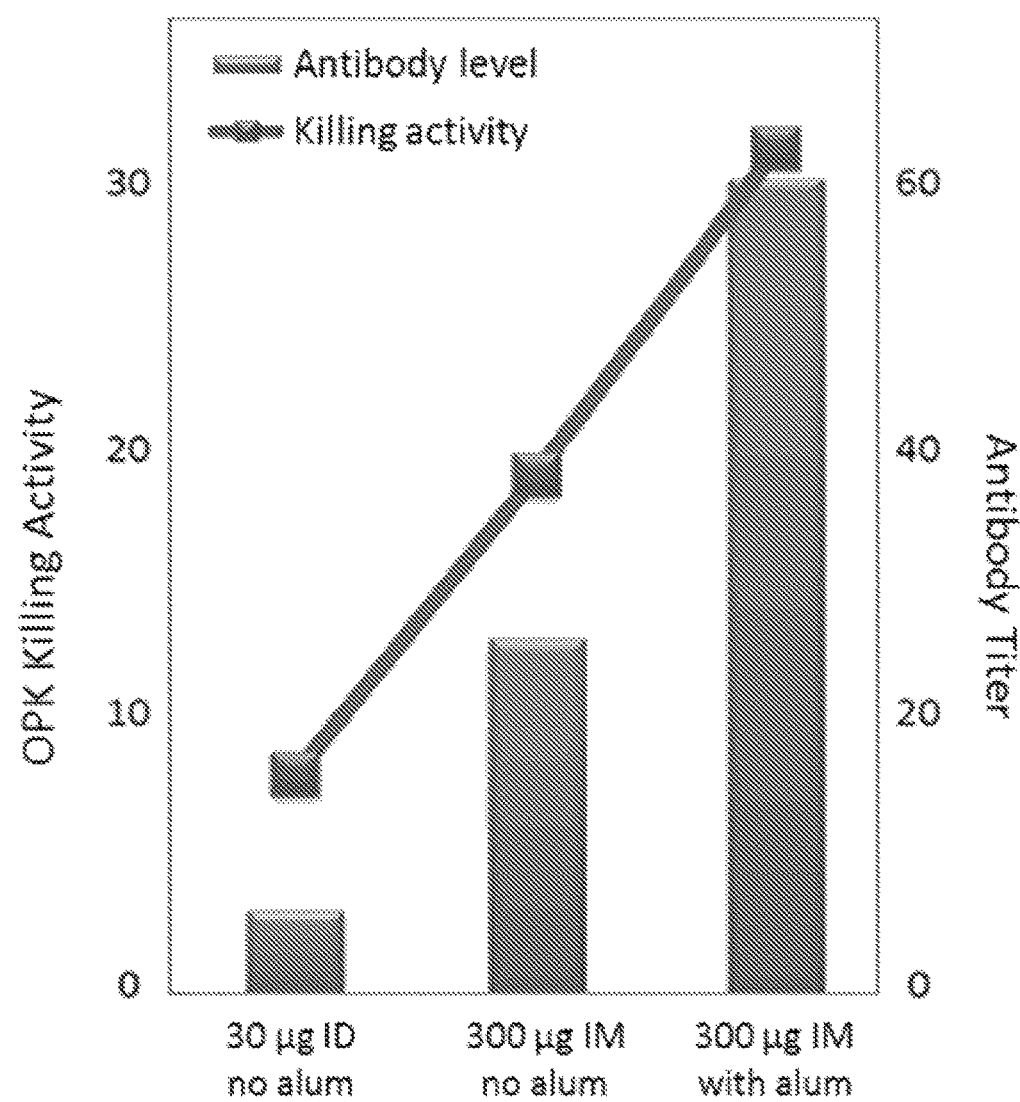

FIG. 10 is a graph showing the geometric mean functional opsonophagocytic killing (OPK) activity (line) in post-vaccination subjects in each treatment group compared to the geomean concentration of anti-Als3 antibodies measured by ELISA among the three treatment groups in the Phase 1 (bars).

Figure 11A:
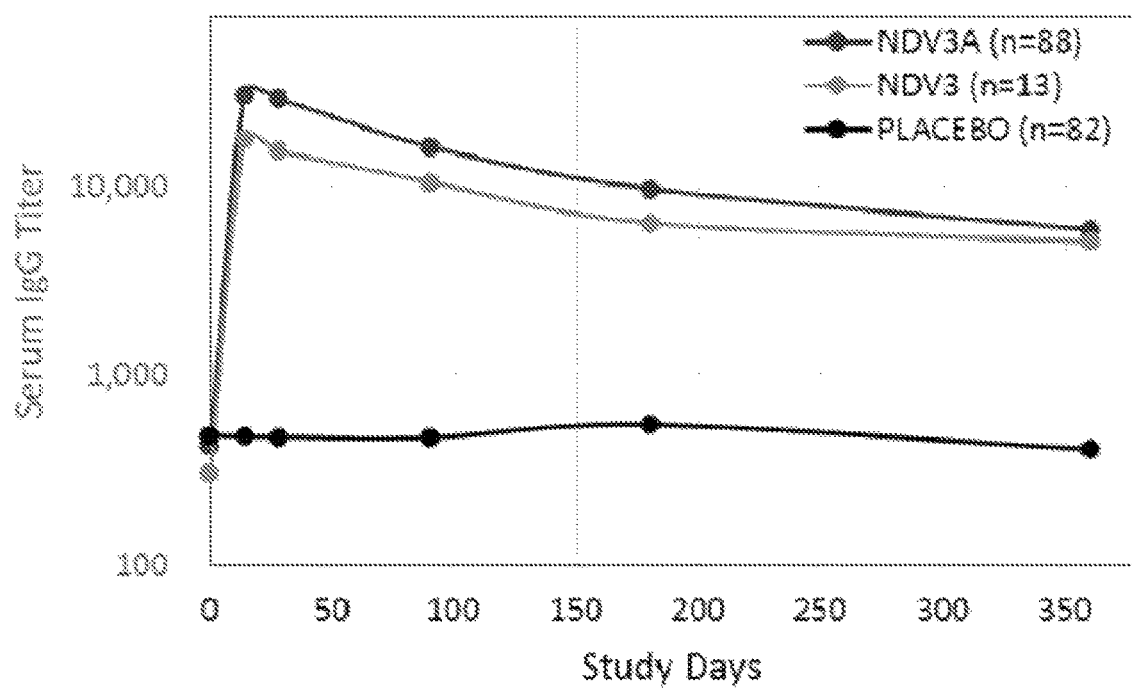
Figure 11B:
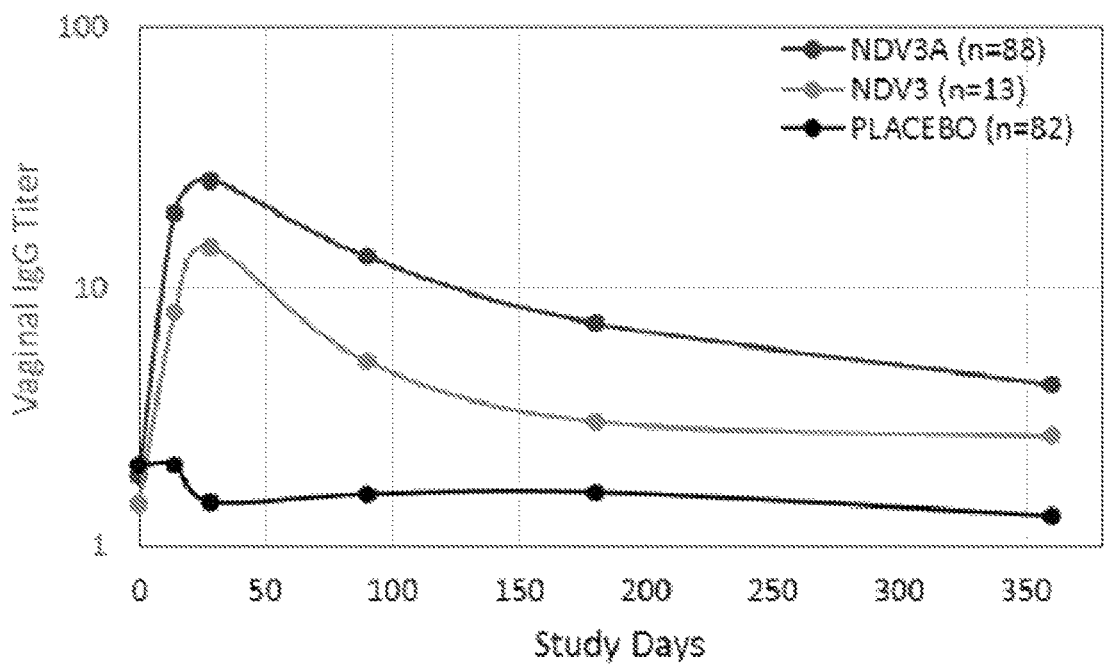
Figure 11C:
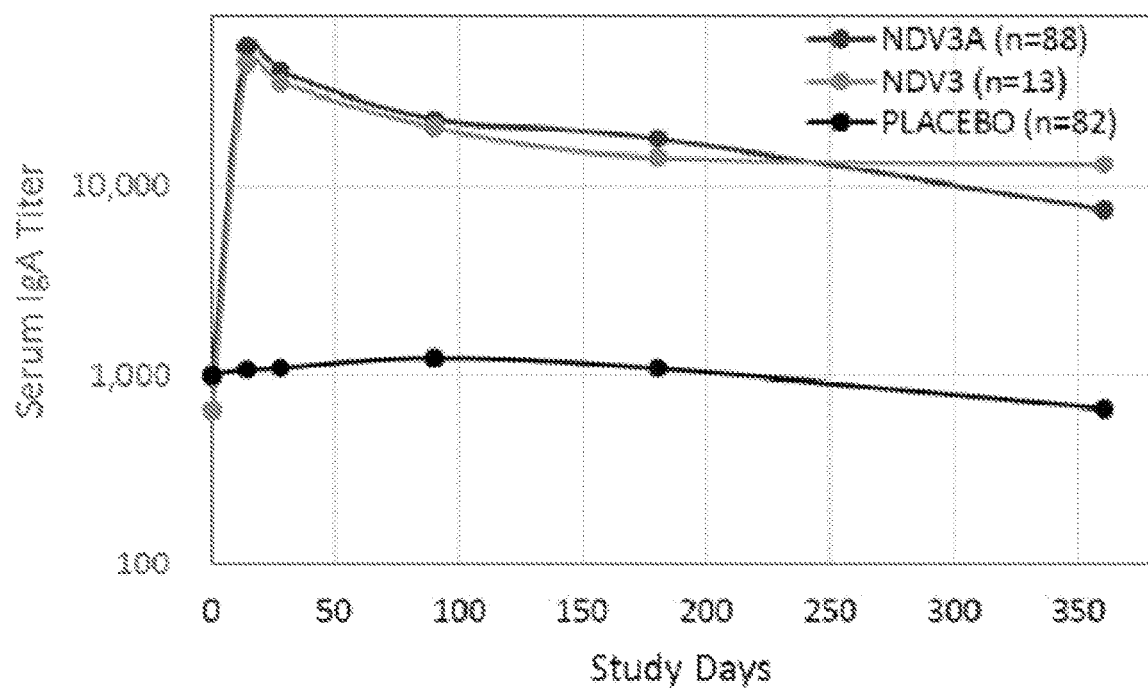
Figure 11D:
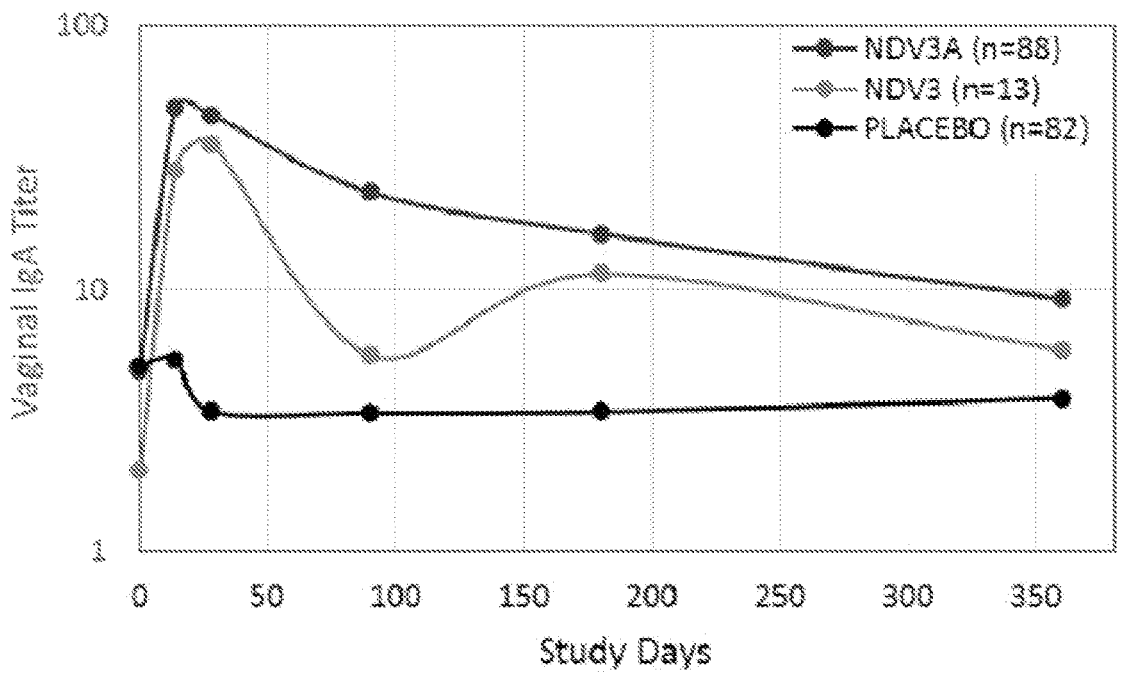

FIGS. 11A-11D are graphs showing anti-Als3 antibody levels in serum (FIG. 11A and FIG. 11C) and vaginal wash (FIGS. 11B and 11D). Each graph shows a comparison between antibody responses to NDV-3A (dark gray line) and NDV-3 (light gray line), relative to placebo (black line). FIG. 11A shows serum IgG titers, FIG. 11B shows vaginal IgG titers, FIG. 11C shows serum IgA titers, and FIG. 11D shows vaginal IgA titers.

Figure 12A:
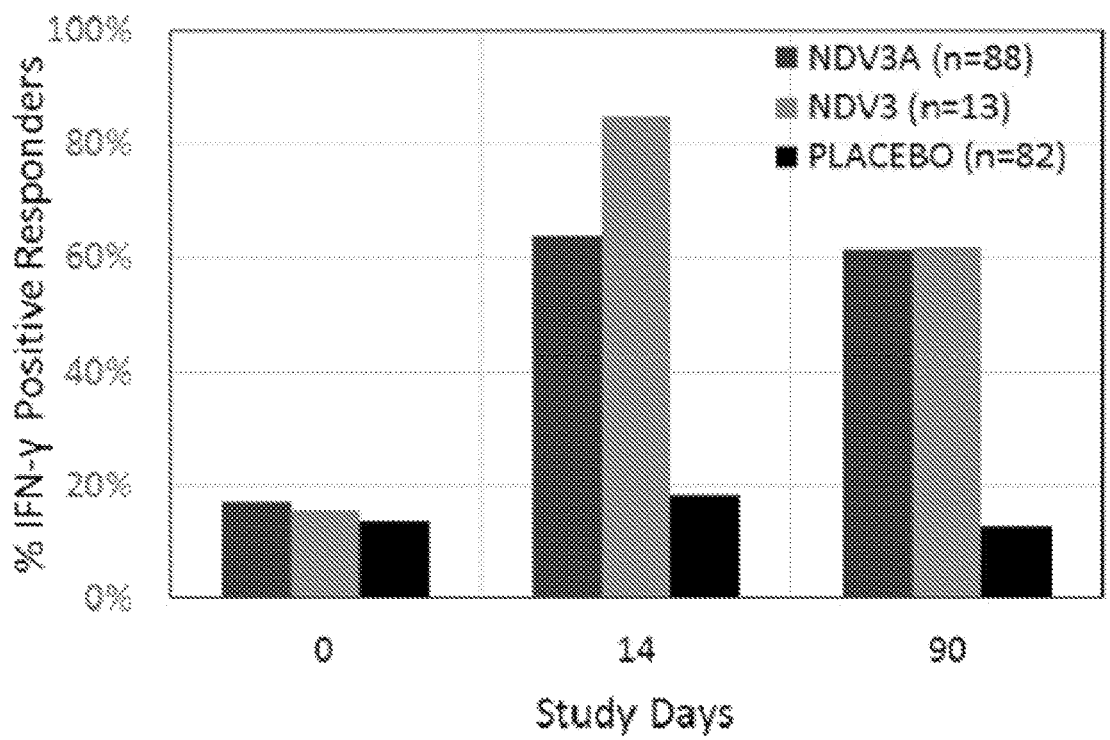
Figure 12B:
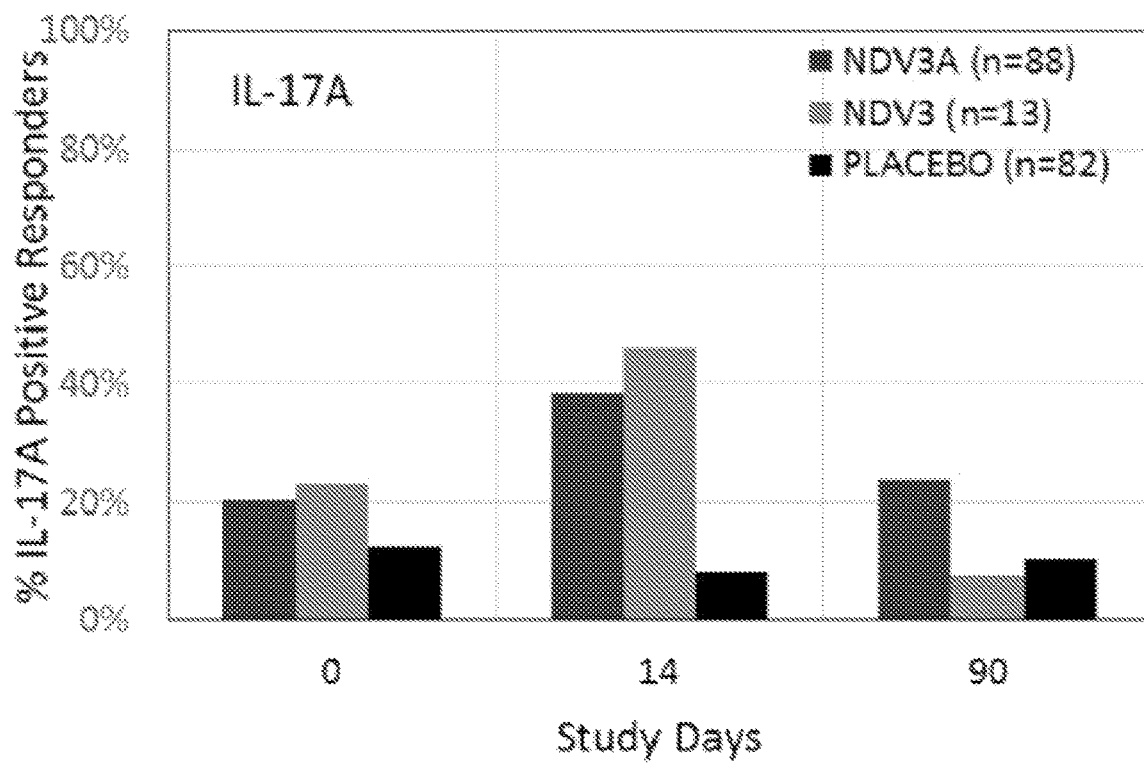

FIGS. 12A and 12B are graphs showing Th1 (FIG. 12A) and Th17 (FIG. 12B) T-cell stimulation by the Als3 antigen. Each graph shows a comparison between cytokine responses to NDV-3A (dark gray bars) and NDV-3 (light gray bars), relative to placebo (black bars). FIG. 12A shows the percentage of IFN-γ positive responders, and FIG. 12B shows the percentage of IL-17A positive responders.

Figure 13:
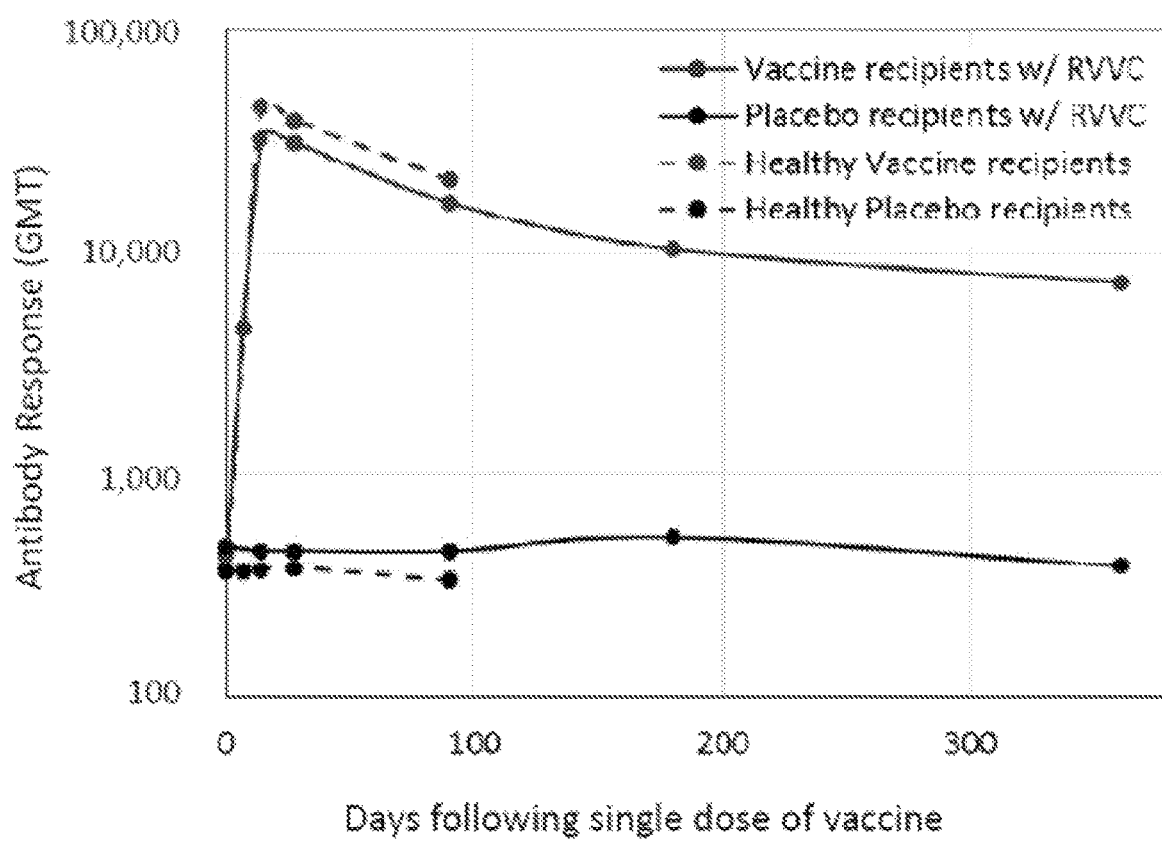

FIG. 13 is a graph comparing the anti-Als3 antibody titers between healthy placebo recipients (black dotted line), healthy vaccine recipients (gray dotted line), placebo recipients with RVVC (black solid line), and vaccine recipients with RVVC (gray solid line).

Figure 14C:
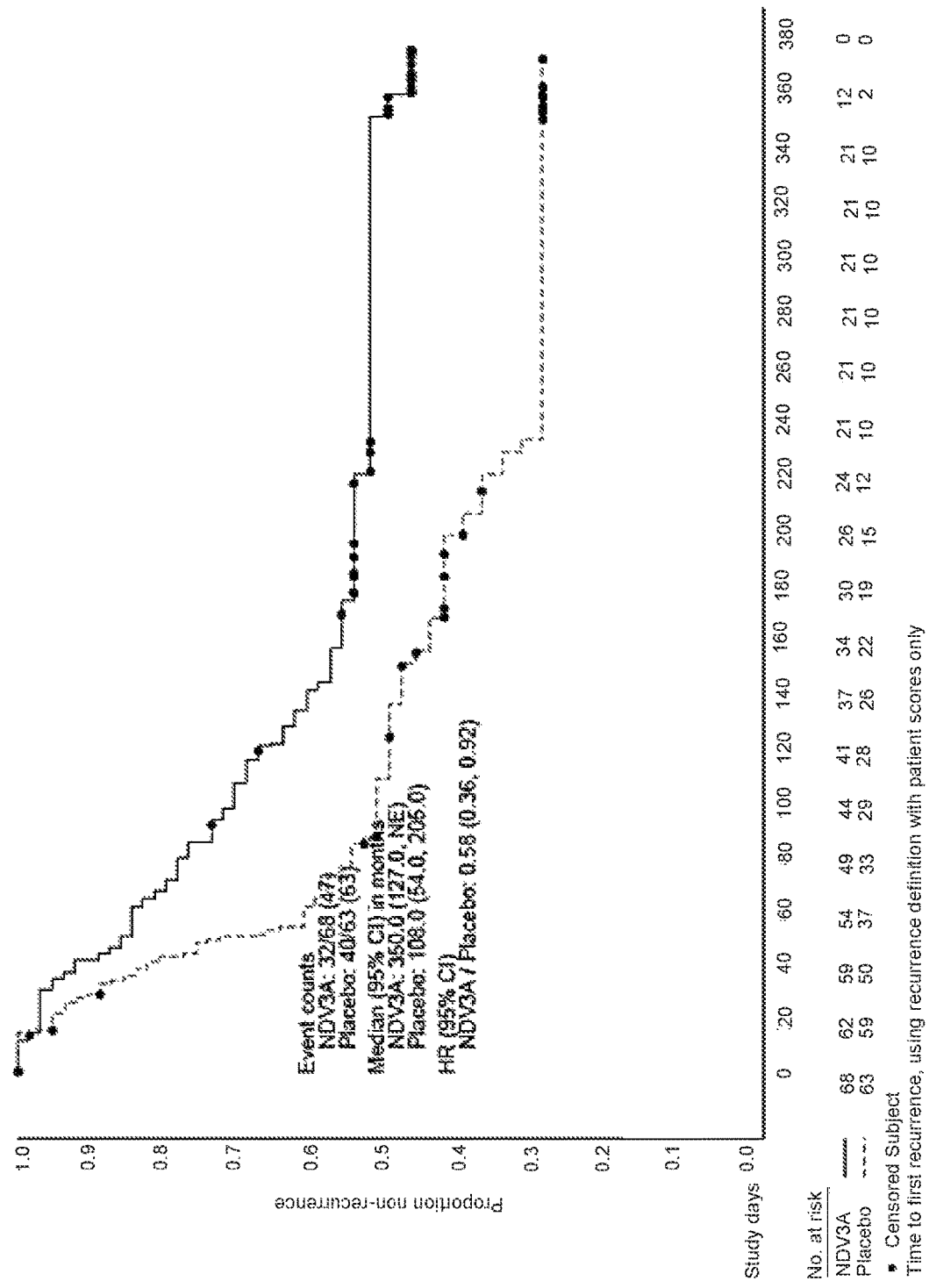

FIGS. 14A-14C are Kaplan-Meier curves showing the time until first recurrence. FIG. 14A shows the proportion of non-recurrence as measured by signs/symptoms score in NDV-3A-treated patients (solid line) in comparison to placebo patients (dashed line) from a cohort of patients of all ages. FIG. 14B shows the proportion of non-recurrence as measured by patient symptom score in NDV-3A-treated patients (solid line) in comparison to placebo patients (dashed line) from a cohort of patients of all ages. FIG. 14C shows the proportion of non-recurrence as measured by patient symptom score in NDV-3A-treated patients (solid line) in comparison to placebo patients (dashed line) from a cohort of patients below the age of 40 years.

Figure 15A:
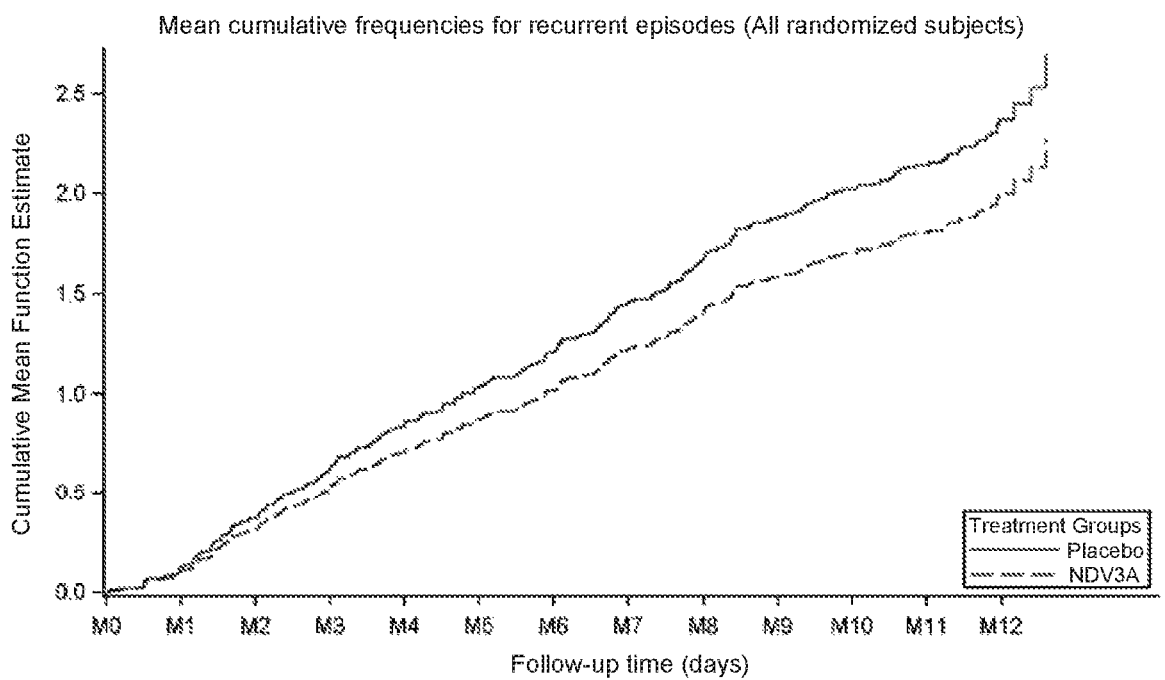
Figure 15B:
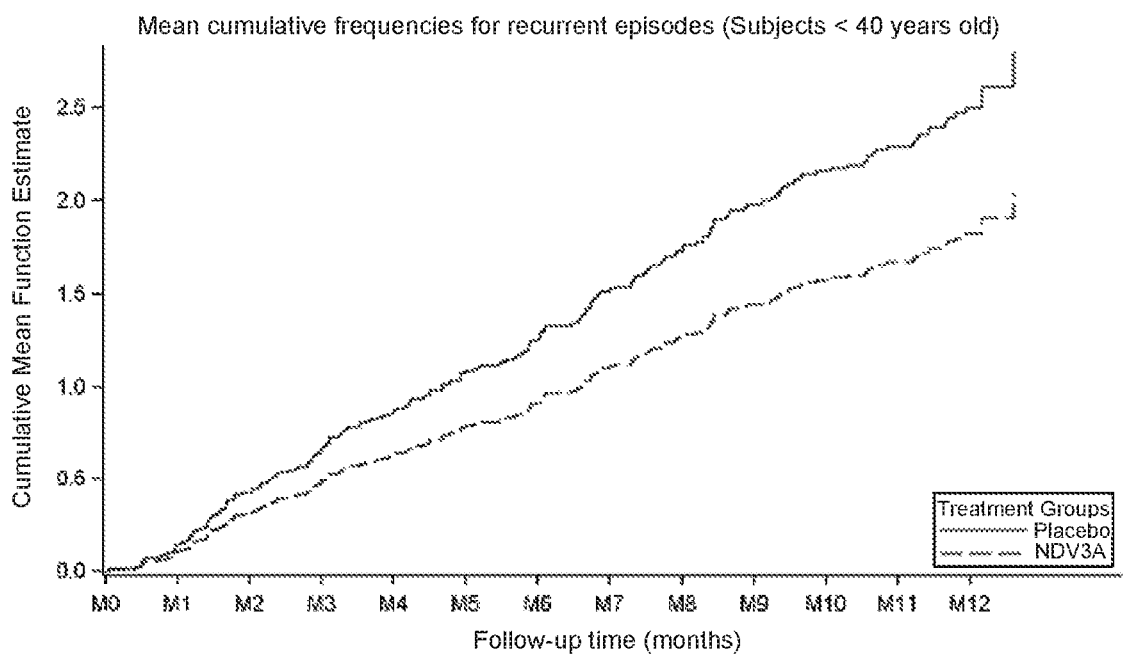
Figure 15C:
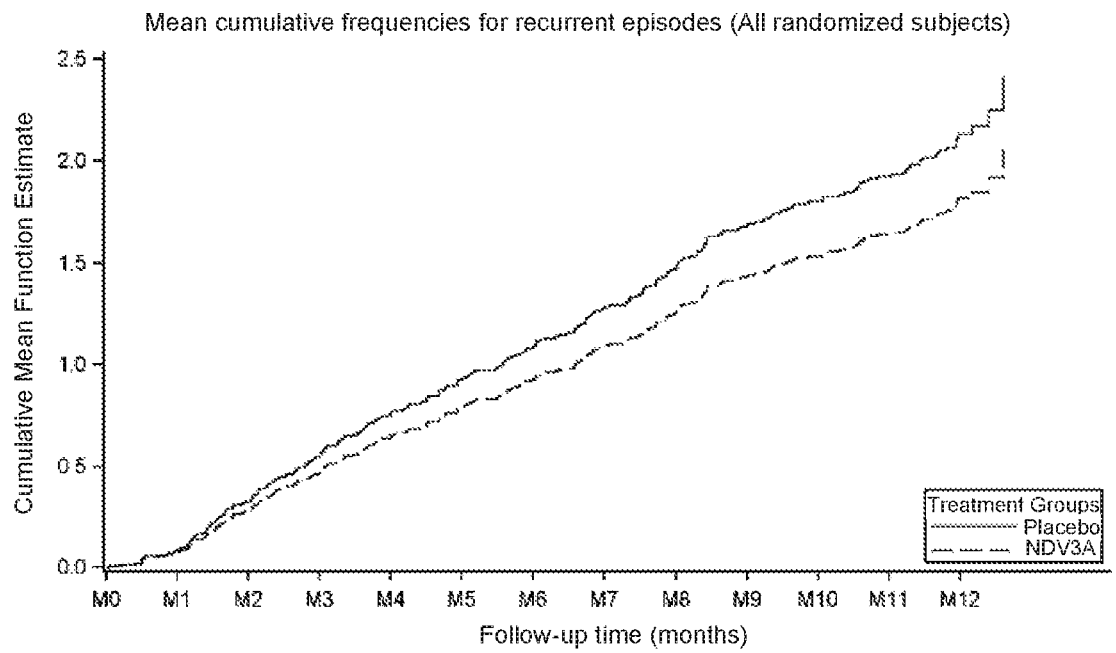
Figure 15D:
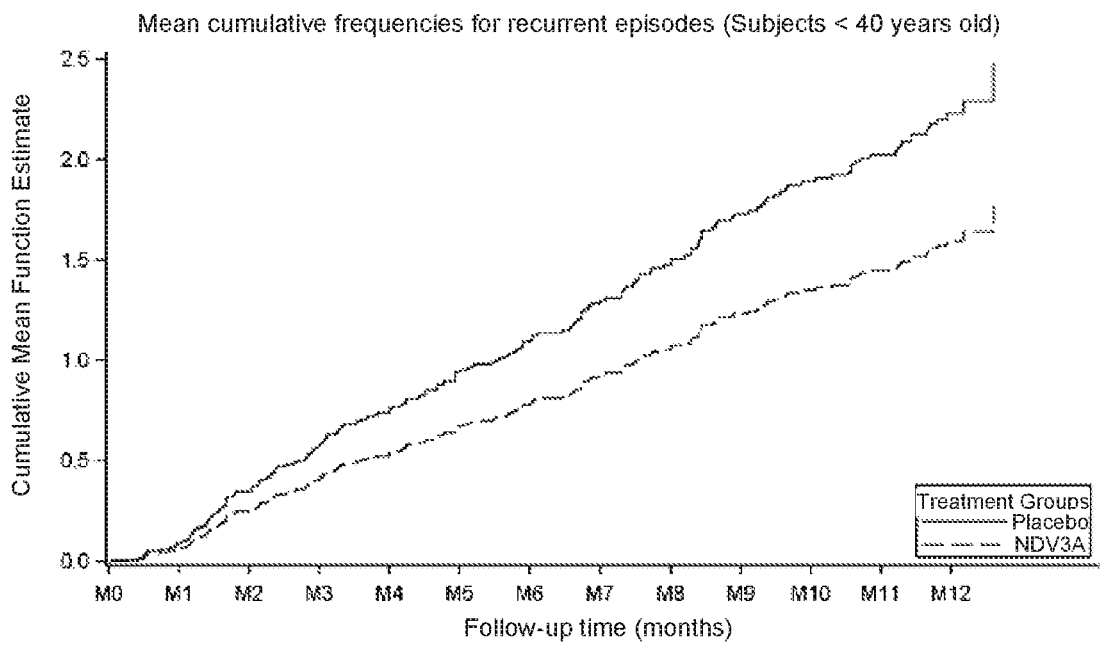

FIGS. 15A-15D are graphs showing cumulative recurrence over time. FIG. 15A shows the mean cumulative number of recurrent episodes as measured by signs/symptom score in NDV-3A-treated patients (dashed line) in comparison with placebo patients (solid line) from a cohort of patients of all ages. FIG. 15B shows the mean cumulative number of recurrent episodes as measured by signs/symptom score in NDV-3A-treated patients (dashed line) in comparison with placebo patients (solid line) from a cohort of patients below the age of 40 years. FIG. 15C shows the mean cumulative number of recurrent episodes as measured by patient symptom score in NDV-3A-treated patients (dashed line) in comparison with placebo patients (solid line) from a cohort of patients of all ages. FIG. 15D shows the mean cumulative number of recurrent episodes as measured by patient symptom score in NDV-3A-treated patients (dashed line) in comparison with placebo patients (solid line) from a cohort of patients below the age of 40 years.

Figure 16:
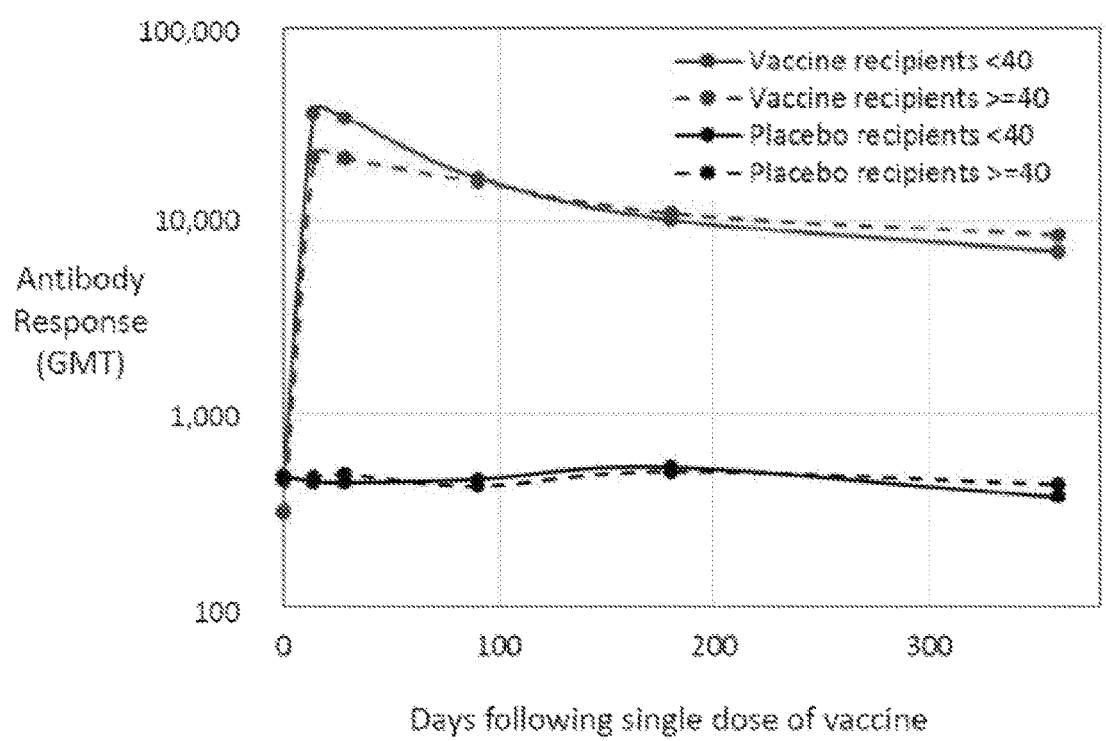

FIG. 16 is a graph comparing the anti-Als3 antibody titers between placebo recipients of age 40 years or over (black dotted line), placebo recipients under the age of 40 years (gray dotted line), vaccine recipients of age 40 years or over (black solid line), and vaccine recipients under the age of 40 years (gray solid line).

DETAILED DESCRIPTION OF THE INVENTION

The invention provides methods for use in preventing and treating vulvovaginal candidiasis (VVC), including recurrent VVC (RVVC). The methods include treatment involving the coordinated use of (i) an agglutinin-like sequence 3 (Als3) polypeptide of *Candida albicans*, and (ii) an antifungal agent. The treatment methods are described further, as follows.

Als3 Polypeptides

The sequence of an agglutinin-like sequence 3 (Als3) pre-protein of *C. albicans* is set forth as follows and designated as SEQ ID NO: 1.

```
                                                           (SEQ ID NO: 1)
  1    MLQQYTLLLIYLSVATAKTI  TGVFNSFNSLTWSNAATYNY  KGPGTPTWNAVLGWSLDGTS

61    ASPGDTFTLNMPCVFKFTTS  QTSVDLTAHGVKYATCQFQA  GEEFMTFSTLTCTVSNTLTP

121    SIKALGTVTLPLAFNVGGTG  SSVDLEDSKCFTAGTNTVTF  NDGGKKISINVDFERSNVDP

181    KGYLTDSRVIPSLNKVSTLF  VAPQCANGYTSGTMGFANTY  GDVQIDCSNIHVGITKGLND

241    WNYPVSSESFSYTKTCSSNG  IFITYKNVPAGYRPFVDAYI  SATDVNSYTLSYANEYTCAG

301    GYWQRAPFTLRWTGYRNSDA  GSNGIVIVATTRTVTDSTTA  VTTLPFDPNRDKTKTIEILK

361    PIPTTTITTSYVGVTTSYST  KTAPIGETATVIVDIPYHTT  TTVTSKWTGTITSTTTHTNP

421    TDSIDTVIVQVPSPNPTVTT  TEYWSQSFATTTTITGPPGN  TDTVLIREPPNHTVTTTEYW

481    SESYTTTSTFTAPPGGTDSV  IIKEPPNPTVTTTEYWSESY  TTTSTFTAPPGGTDSVIIKE
```

```
-continued
 541    PPNHTVTTTEYWSQSYTTTT  TVTAPPGGTDTVLVREPPNH  TVTTTEYWSQSYTTTTTVIA

601    PPGGTDSVIIREPPNPTVTT  TEYWSQSYATTTTITAPPGE  TDTVLIREPPNHTVTTTEYW

661    SQSYATTTTITAPPGETDTV  LIREPPNHTVTTTEYWSQSF  ATTTTVTAPPGGTDTVIIRE

721    PPNHTVTTTEYWSQSYATTT  TITAPPGETDTVLIREPPNH  TVTTTEYWSQSYATTTTIIA

781    PPGETDTVLIREPPNPTVTT  TEYWSQSYTTATTVTAPPGG  TDTVIIYDTMSSSEISSFSR

841    PHYTNHTTLWSTTWVIETKT  ITETSCEGDKGCSWVSVSTR  IVTIPNNIETPMVTNTVDST

901    TTESTSQSPSGIFSESGVSV  ETESSTVTTAQTNPSVPTTE  SEVVFTTKGNNENGPYESPS

961    TNVKSSMDENSEFTTSTAAS  TSTDIENETIATTGSVEASS  PIISSSADETTTVTTTAEST

1021    SVIEQPTNNNGGGKAPSATS  SPSTTTTANNDSVITGTTST  NQSQSQSQYNSDTQQTTLSQ

1081    QMTSSLVSLHMLTTFDGSGS  VIQHSTWLCGLITLLSLFI.
```

This pre-protein includes an N-terminal signal sequence of 17 amino acids (underlined above), which is removed in the generation of mature Als3 protein.

Examples of Als3 polypeptides that can be used in the invention include those which include an N-terminal portion of the mature form of *C. albicans* Als3, and variants thereof. Thus, for example, an Als3 polypeptide can include 416 amino acids of N-terminal sequence of mature Als3.

A specific example of an Als3 polypeptide that can be used in the invention is Als3-2, which is a recombinant polypeptide expressed in *Saccharomyces cerevisiae* that is based on an N-terminal region (416 residues) of mature Als3 from *C. albicans*. A sequence of Als3-2 is set forth as follows and designated as SEQ ID NO: 2.

```
                                                              (SEQ ID NO: 2)
KTITGVFNSF  NSLTWSNAAT  YNYKGPGTPT  WNAVLGWSLD  GTSASPGDTF  TLNMPCVFKF   60

TTSQTSVDLT  AHGVKYATCQ  FQAGEEFMTF  STLTCTVSNT  LTPSIKALGT  VTLPLAFNVG  120

GTGSSVDLED  SKCFTAGTNT  VTFNDGGKKI  SINVDFERSN  VDPKGYLTDS  RVIPSLNKVS  180

TLFVAPQCAN  GYTSGTMGFA  NTYGDVQIDC  SNIHVGITKG  LNDWNYPVSS  ESFSYTKTCS  240

SNGIFITYKN  VPAGYRPFVD  AYISATDVNS  YTLSYANEYT  CAGGYWQRAP  FTLRWTGYRN  300

SDAGSNGIVI  VATTRTVTDS  TTAVTTLPFD  PNRDKTKTIE  ILKPIPTTTI  TTSYVGVTTS  360

YLTKTAPIGE  TATVIVDIPY  HTTTTVTSKW  TGTITSTTTH  TNPTDSIDTV  IVQVPL.     416
```

Another specific example of an Als3 polypeptide that can be used in the invention is Als3-1 which, similar to Als3-2, is a recombinant polypeptide expressed in *Saccharomyces cerevisiae* that is based on an N-terminal region (416 residues) of mature the Als3 from *C. albicans*. In contrast to Als3-2, Als3-1 includes a 15 amino acid sequence containing a six-His tag region on the N-terminal end to facilitate purification. A sequence of Als3-1 is set forth as follows and designated as SEQ ID NO: 3.

```
                                                              (SEQ ID NO: 3)
HHHHHHGIQK  TITGVFNSFN  SLTWSNAATY  NYKGPGTPTW  NAVLGWSLDG  TSASPGDTFT   60

LNMPCVFKFT  TSQTSVDLTA  HGVKYATCQF  QAGEEFMTFS  TLTCTVSNTL  TPSIKALGTV  120

TLPLAFNVGG  TGSSVDLEDS  KCFTAGTNTV  TFNDGGKKIS  INVDFERSNV  DPKGYLTDSR  180

VIPSLNKVST  LFVAPQCANG  YTSGTMGFAN  TYGDVQIDCS  NIHVGITKGL  NDWNYPVSSE  240

SFSYTKTCSS  NGIFITYKNV  PAGYRPFVDA  YISATDVNSY  TLSYANEYTC  AGGYWQRAPF  300

TLRWTGYRNS  DAGSNGIVIV  ATTRTVTDST  TAVTTLPFDP  NRDKTKTIEI  LKPIPTTTIT  360
```

```
TSYVGVTTSY LTKTAPIGET ATVIVDIPYH TTTTVTSKWT GTITSTTTHT NPTDSIDTVI    420

VQVPL.                                                              425
```

Additional Als3 polypeptides include Als3 (18-324) and Als3 (Ser/Thr-rich sequence).

A sequence of Als3 (18-324) is set forth as follows and designated as SEQ ID NO: 4.

```
                                                          (SEQ ID NO: 4)
            KTI TGVFNSFNSLTWSNAATYNY KGPGTPTWNAVLGWSLDGTS

ASPGDTFTLNMPCVFKFTTS QTSVDLTAHGVKYATCQFQA GEEFMTFSTLTCTVSNTLTP

SIKALGTVTLPLAFNVGGTG SSVDLEDSKCFTAGTNTVTF NDGGKKISINVDFERSNVDP

KGYLTDSRVIPSLNKVSTLF VAPQCANGYTSGTMGFANTY GDVQIDCSNIHVGITKGLND

WNYPVSSESFSYTKTCSSNG IFITYKNVPAGYRPFVDAYI SATDVNSYTLSYANEYTCAG

GYWQRAPFTLRWTGYRNSDA GSNG.
```

A sequence of Als3 (Als3 Ser/Thr-rich sequence) is set forth as follows and designated as SEQ ID NO: 5.

```
                                                          (SEQ ID NO: 5)
IVIVATTRTVTDSTTA      VTTLPFDPNRDKTKTIEILK PIPTTTITTSYVGVTTSYST
KTAPIGETATVIVDIPYHTT TTVTSKWTGTITSTTTHTNP TDSIDTVIVQVP.
```

The invention includes the use of proteins or polypeptides that comprise or consist of Als3 proteins and polypeptides such as those described above (e.g., SEQ ID NO: 1, 2, 3, 4, or 5), as well as fragments thereof. In particular, the invention includes the use of NDV-3, a vaccine formulation that includes Als3-1 (SEQ ID NO: 3). The invention also includes the use of NDV-3A, a vaccine formulation that includes Als3-2 (SEQ ID NO: 2). In addition, the invention also includes the use of variants of the Als3 proteins and polypeptides described above. Variants include proteins and polypeptides (or fragments thereof) that are substantially identical to SEQ ID NO: 1, 2, 3, 4, or 5, as set forth above, and in reference to the definition of "substantially identical," as set forth above.

In some instances, a modification to a polypeptide as described herein does not substantially reduce the biological activity, e.g., immunogenic activity, of the polypeptide. The modified polypeptide may have or may optimize a characteristic of a polypeptide, such as in vivo stability, bioavailability, toxicity, immunological activity, immunological identity, or conjugation properties.

Modifications include those by natural processes, such as posttranslational processing, or by chemical modification techniques known in the art. Modifications may occur anywhere in a polypeptide including the polypeptide backbone, the amino acid side chains, and the amino- or carboxy-terminus. The same type of modification may be present in the same or varying degrees at several sites in a given polypeptide, and a polypeptide may contain more than one type of modification.

A variant or otherwise modified polypeptide can also include one or more amino acid insertions, deletions, or substitutions, either conservative or non-conservative (e.g., D-amino acids, desamino acids) in the polypeptide sequence. For example, the addition of one or more cysteine residues to the amino or carboxy terminus of any of the polypeptides of the invention can facilitate conjugation of these polypeptides. Exemplary polypeptides have an N- or C-terminal cysteine.

Amino acid substitutions can be conservative (i.e., wherein a residue is replaced by another of the same general type or group) or non-conservative (i.e., wherein a residue is replaced by an amino acid of another type). In addition, a non-naturally occurring amino acid can be substituted for a naturally occurring amino acid (i.e., non-naturally occurring conservative amino acid substitution or a non-naturally occurring non-conservative amino acid substitution).

Polypeptides made synthetically, e.g., using methods known in the art, can include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Variants may be generated by substitutional mutagenesis and retain or even increase the biological activity, e.g., immunogenic activity, of the original polypeptide.

The polypeptides described herein can be obtained, e.g., by chemical synthesis using a commercially available automated peptide synthesizer. The synthesized protein or polypeptide can be precipitated and further purified, for example by high performance liquid chromatography (HPLC). Alternatively, the proteins and polypeptides can be obtained by recombinant methods that are well-known in the art (e.g., expression in *S. cerevisiae*).

Conjugates

Polypeptides of the invention may, in certain embodiments, be conjugated to another moiety or particle.

Protein Moieties

In some instances, it may be useful to conjugate a polypeptide to a protein that is immunogenic in the species to be immunized, e.g., keyhole limpet hemocyanin (KLH), CRM197 and variants thereof, tetanus toxoid, diptheria toxoid, serum albumin, bovine thyroglobulin, soybean trypsin inhibitor, or a polycation (poly-L-lysine or poly-L-arginine), e.g., using a bifunctional or derivatizing agent as known in the art, for example, maleimidobenzoyl sulfosuccinimide ester (conjugation through cysteine residues), N-hydroxysuccinimide (through lysine residues), glutaraldehyde, or succinic anhydride.

In some instances, the conjugate may be a recombinant fusion protein made, e.g., to facilitate expression and purification of the polypeptide.

Particles for Conjugation or Display of Polypeptides

In some instances, polypeptides are conjugated to or displayed on a particle, e.g., a phage, a yeast, a virus, a virosome, or a recombinant virus-like particle.

For example, one or more polypeptides may be conjugated to a phage, a yeast, or a virus particle, e.g., to the surface of the particle. In one embodiment, a nucleic acid molecule encoding the polypeptide is inserted into the phage, yeast, or virus particle, resulting in expression of the polypeptide in the phage, yeast, or virus, e.g., at the surface of the particle. The phage, yeast, or virus population containing the polypeptide may then be isolated and prepared, e.g., as a vaccine, by adding a pharmaceutically acceptable excipient.

In some embodiments, polypeptides as described herein are conjugated to a virosome or virus-like particle (VLP). Virosomes and VLPs generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. Viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p 1). Virosomes are discussed further in, e.g., Gluck et al. (2002), Vaccine 20:B10-B16, which is incorporated by reference in its entirety.

VLPs are discussed further, e.g., in Niikura et al. (2002), Virology 293:273-280; Lenz et al. (2001), J Immunol 166: 5346-5355; Pinto et al. (2003), J Infect Dis 188:327-338; Gerber et al. (2001), Viral 75:4752-4760; WO03/024480; and WO03/024481, each of which is incorporated by reference in its entirety.

Antifungal Agents

Antifungal agents that can be used in the invention include those that are standardly used by medical professionals in the treatment of candidiasis including, for example, an azole (e.g., a triazole, such as fluconazole, albaconazole, efinaconazole, epoxiconazole, isavuconazole, itraconazole, posaconazole, propiconazole, ravuconazole, terconazole, and voriconazole; an imidazole, such as bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, and tioconazole; and a thiazole, such as abafungin), a polyene (e.g., amphotericin B, candicidin, filipin, hamycin, natamycin, nystatin, and rimocidin), an allylamine (e.g., amorolfin, butenafine, naftifine, and terbinafine), an echinocandin (e.g., anidulafungin, biafungin (e.g., CD101), caspofungin, and micafungin), lanosterol demethylase inhibitors (e.g., VT-1161) and other antifungal agents, including, but not limited to, benzoic acid, ciclopirox olamine, enfumafungin (e.g., SCY-078), 5-flucytosin, griseofulvin, haloprogin, tolnaftate, aminocandin, chlordantoin, chlorphenesin, nifuroxime, undecylenic acid, and crystal violet, and pharmaceutically acceptable salts or esters thereof.

In particular, the antifungal agent is fluconazole. Huconazole is commercially available and sold under the name DIFLUCAN® in the United States. The chemical name of fluconazole is 2-(2,4-difluorophenyl)-1,3-bis(1H-1,2,4-triazol-1-yl)propan-2-ol, and it has the following structure:

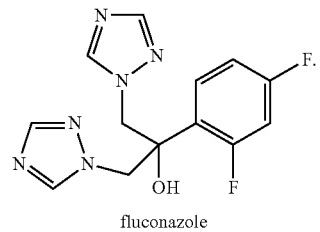 [SMILES: OC(Cn1cncn1)(Cn1cncn1)c1ccc(F)cc1F]

fluconazole

Methods of synthesizing fluconazole are described in U.S. Pat. Nos. 4,404,216 and 5,710,280.

Patient Identification

Patients can be identified for treatment according to the methods of the invention using standard methods, which are widely used in clinical settings. These methods can optionally include any one or more aspects of the following exemplary methods.

A diagnosis of VVC can include positive mycological results for *Candida*. Also, standard testing can be done to rule out other infections. For example, a whiff test and a vaginal pH test can be done to rule out bacterial vaginosis (BV). In addition, a wet mount can be done to rule out clue cells associated with BV, as well as to rule out infection due to *Trichomonas vaginalis*. Samples can be analyzed using DNA amplification assays to rule out *Chlamydia tracomatis* and *Neisseria* gonorrhea using, for example, a commercially available system (e.g., BD ProbeTec™ ET System, BD Diagnostics, Sparks, Md.). In another example, *Candida* can be positively identified, and *Gardnerella vaginalis* and *Trichomonas vaginalis* can be ruled out, using, for example, a commercially available DNA probe test (e.g., BD Affirm™ VPIII Microbial Identification System; BD Diagnostics, Sparks, Md.).

In addition to these methods, a minimum Composite Questionnaire Score of signs and symptoms can be utilized. Per draft FDA guidance published in 1998, signs and symptoms of VVC are scored both by the subject and by the examining clinician. An example of the VVC Sign and Symptom Questionnaire includes asking a subject to score the following symptoms as absent (0), mild (1), moderate (2), or severe (3): itching, irritation, and burning. The examining clinician will examine the subject and score the following signs as absent (0), mild (1), moderate (2), or severe (3): erythema, edema, and excoriation/fissure formation.

The two scores are combined to create a Composite Questionnaire Score. A Composite Questionnaire Score of "0-2" is not clinically indicative of VVC. The following scoring ranges are clinically indicative of VVC:

3-6=Mild Disease
7-12=Moderate Disease
≥13=Severe Disease

Alternatively, a diagnosis of VVC or RVVC can be made based solely on a Composite Questionnaire Score of signs and symptoms as completed by the subject.

Recurrent VVC (RVVC) is generally defined as four or more episodes of VVC in the preceding year, with at least one of these episodes being documented with culture (Workowski et al. (2006), MMWR Recomm. Rep. 55(RR-11):1-94).

The invention includes treatment of patients with RVVC, as defined herein, as well as patients with VVC (e.g., patients having a first incident of candidiasis, or patients having one or two prior episodes within the preceding year).

As described further below, the invention also includes treatment of subjects at risk of developing RVVC. Such patients may not have a current diagnosis of VVC, and/or may not be experiencing a current episode of VVC, at the time of treatment. These subjects, for example, may not have a VVC Sign and Symptom Composite Questionnaire Score of ≥3 at the time of treatment. Furthermore, these patients may have previously had a diagnosis of VVC or recurrent VVC. The diagnosis may be made with or without a positive culture result.

In addition to standard methods of identifying a patient for RVVC treatment, the invention provides a method of identifying a patient based on the age of the patient. As described further below, a patient suitable for treatment by any of the methods or compositions of the present invention can be a female under the age of 40 years.

Vaccine Compositions

Formulations for vaccine compositions as described herein can be prepared using standard pharmaceutical formulation chemistries and methodologies that are readily available to the reasonably skilled artisan. For example, polypeptides or conjugates as described herein can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions may include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (e.g., a powder or granules) form for reconstitution with a suitable vehicle (e.g., sterile pyrogen-free water) prior to parenteral administration of the reconstituted composition. The compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions that are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the polypeptides and conjugates described herein may be encapsulated, adsorbed to, or associated with particulate carriers. Suitable particulate carriers include those derived from polymethyl methacrylate polymers, as well as PLG microparticles derived from poly(lactides) and poly(lactide-co-glycolides). See, e.g., Jeffery et al. (1993) *Pharm. Res.* 10:362-368. Other particulate systems and polymers can also be used, for example, polymers such as polylysine, polyarginine, polyornithine, spermine, spermidine, as well as conjugates of these molecules.

The formulated compositions will include an amount of one or more polypeptides or conjugates described herein that is sufficient to mount an immunological response. An immunogenic amount can be readily determined by one of skill in the art. Such an amount will fall in a relatively broad range that can be determined through routine trials. The compositions may contain from about 0.1% to about 99.9% of the polypeptides, conjugates, or antifungal agents, and can be administered directly to the subject or, alternatively, delivered ex vivo, to cells derived from the subject, using methods known to those skilled in the art.

Compositions can include a mixture of distinct polypeptides or conjugates as described herein. For example, vaccines may include, e.g., 2, 3, 4, 5, 6, 7, 8, or more distinct polypeptides or conjugates as described herein, e.g., containing or consisting of the amino acid sequences of SEQ ID NOs: 1, 2, 3, 4, or 5, or a variant sequence thereof having up to three substitutions (e.g., conservative substitutions), deletions, or additions to the amino acid sequence of any one of SEQ ID NOs:1, 2, 3, 4, or 5.

Substances that stimulate the immune response, e.g., adjuvants, may be included in the compositions, e.g., in vaccines. Examples of chemical compounds used as adjuvants include, but are not limited to, aluminum compounds (e.g., alum, Alhydrogel (aluminum hydroxide), Adjuphos (aluminum phosphate)), oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, and co-stimulatory factors.

Als3 polypeptides, optionally in combination with an adjuvant (e.g., aluminum hydroxide; also see above), can be formulated in compositions including, for example, a buffer and a salt. Such compositions can thus include, for example, sodium phosphate, sodium citrate, histidine, or sodium succinate (2-20 mM, e.g., 5-15 mM or 10 mM), pH 6.0-8.0 (e.g., pH 6.5-7.5 or pH 7.0), as well as sodium chloride (100-300 mM, e.g., 100-200 mM or 154 mM.

A specific example of a vaccine formulation that can be used in the invention is NDV-3, which includes Als3-1 formulated in 10 mM sodium phosphate, pH 7.0, and 154 mM sodium chloride. Another example is NDV3-A, which includes Als3-2 formulated in 10 mM sodium phosphate, pH 6.5, and 154 mM sodium chloride. The NDV-3 and NDV-3A vaccines can optionally be filled in 2 mL glass vials with a 0.7 mL volume containing 600 μg Als3-1 (or Als3-2)/mL, 1.0 mg Al/mL as aluminum hydroxide and phosphate-buffered saline. When withdrawn from the vial with a needle and syringe for injection, approximately 0.5 mL can be injected (e.g., by the intramuscular route), resulting in a delivered dose of 300 μg of Als3-1 (or Als3-2).

Methods of Treatment

As noted above, the methods of the invention involve coordinated administration of (i) an agglutinin-like sequence 3 (Als3) polypeptide of *Candida albicans*, and (ii) an antifungal agent. The Als3 polypeptide and antifungal agent are generally as described elsewhere herein, but can be, as examples, Als3-1, Als3-2, Als3 (18-324), and/or Als3 (Ser/Thr-rich sequence), or variants thereof (with Als3-1 or Als3-2 optionally in the form of NDV-3 or NDV-3A, respectively), and fluconazole.

As will be described further below, there are many different approaches to coordinated administration of an Als3 polypeptide and an antifungal agent that can be used in the invention. For instance, the method may include treatment with an antifungal agent prior to Als3 polypeptide administration. Taking this approach enables treatment of an acute episode quickly with the antifungal agent, while vaccinating with an Als3 polypeptide afterwards, in an effort to prevent recurrence and/or to supplement the action of the antifungal agent in addressing the acute attack.

In one example, a patient is treated with an antifungal agent 1-4, e.g., 2-3, times before vaccination, and the antifungal treatment takes place, for example, within a time frame of 1, 2, or 3 weeks prior to vaccination. Thus, in a specific example, treatment with an antifungal agent can be carried out on days −14, −11, and −8 relative to day 0, which is the day on which vaccination with an Als3 polypeptide takes place. Any of the antifungal treatment and/or vaccination days can vary by, e.g., 1 or 2 days before or after the days noted above.

In other examples, antifungal treatment takes place on the day of vaccination, in addition to (or instead of) prior antifungal treatment according to, for example, a schedule as noted above. Thus, in one specific example, antifungal treatment takes place on days −14, −11, and −8 (±1 or 2 days for each day of administration), and also on day 0, the same day as vaccination (±1 or 2 days).

In further examples, antifungal treatment takes place after the day of vaccination, in addition to (or instead of) prior antifungal treatment according to, for example, a schedule as noted above, and optionally in addition to antifungal treatment on day 0, as noted above. Treatment after the day of vaccination can take place, for example, at any time within 3 to 4 weeks after vaccination, and can take the form of, for example, 1-4 treatments. In one example, post-vaccination treatment takes place on day 7 and/or day 14 (±1 or 2 days). Thus, in one specific example, antifungal treatment takes place on days −14, −11, and −8 (±1 or 2 days for each day of administration), further antifungal treatment and vaccination takes place on day 0 (±1 or 2 days), and is followed by still further antifungal treatment at day 7 and/or day 14 (±1 or 2 days). In the examples described in this paragraph, the "vaccination" is a single dose primary vaccination regimen or the initial dose of a multi-dose primary vaccination regimen (see below).

Treatment according to the regimens noted above can be varied, as determined to be appropriate by those of skill in the art. For example, in the instance of a particularly acute case, the patient may be treated with a single or double-dose of antifungal agent on the first day of treatment, and daily administration of anti-fungal agent may continue until symptoms have dissipated sufficiently, as determined by those of skill in the art. Thus, for example, daily treatment may continue for 2-6 days, 1 week, or 1-2 weeks, and be followed by vaccination (optionally including further antifungal treatment on the same day and/or further antifungal treatment following vaccination as, e.g., described herein).

In addition to coordinated administration of an Als3 polypeptide and an antifungal agent, as described above, the invention also includes methods involving the administration of an Als3 polypeptide without an antifungal agent, to subjects at risk of RVVC (e.g., subjects who have previously had a diagnosis of VVC or RVVC). Such subjects may have had, for example, one, two, three, or more VVC infections during the past 12 months prior to treatment. Further, at the time of treatment, these subjects may not have a current diagnosis of VVC, and/or may not be experiencing a current episode of VVC. Further, at the time of treatment, these patients may not have a VVC Sign and Symptom Composite Questionnaire Score of ≥3 at the time (see above).

The methods of the invention also include optional administration of a primary vaccination regimen and subsequent booster doses of Als3 polypeptides as described herein. The primary vaccination regimen is defined by the number of doses administered and time intervals between the doses. The primary vaccination regimen is optimized to achieve an optimal initial protection in newly vaccinated patients. The number of doses in a primary vaccinated regimen is typically 1-4. The time period for the completion of a primary vaccination regimen is 1-12 months. These primary vaccination doses can be administered at, for example, 1-11 months after the initial vaccination, as determined to be appropriate by one skilled in the art. Thus, in various examples, one or more primary vaccination doses can be administered at 2-10, 3-9, 4-8, 5-7, or 6 months after the initial vaccination. Booster doses can be administered following the primary vaccination regimen to increase the longer-term duration of protection. Booster doses can be administered at 1-10 years following the first dose of the primary series and are typically a single dose. The amount of Als3 polypeptide present in all primary vaccination doses and booster doses is typically the same, but can vary and be, for example, an amount as described elsewhere herein, or optionally can be 5-20%, e.g., 10%, of the amount of the initial dose.

The invention also features methods of detecting recurrence of VVC. Recurrence may be detected by the patient's own observation of her symptoms. Additionally, or alternatively, recurrence may be detected by the physician, in which the physician's observations of signs or symptoms of infection determine whether or not a patient experiences recurrence. Additionally, or alternatively to these detection methods, a vaginal mycological culture positive for *C. albicans* may be used alone or in combination with one or both of the patient's own determination of infection and the physician's assessment of infection to determine whether a recurrence of VVC has occurred.

Compositions as described herein can be delivered to a mammalian subject (e.g., a human or other mammal described herein) using a variety of known routes and techniques. For example, a composition can be provided as an injectable solution, suspension, or emulsion, and administered via intramuscular, subcutaneous, intradermal, intracavity, parenteral, epidermal, intraarterial, intraperitoneal, or intravenous injection using a conventional needle and syringe, or using a liquid jet injection system. Compositions can also be administered topically to skin or mucosal tissue, such as nasally, intratracheally, intestinal, rectally, or vaginally, or provided as a finely divided spray suitable for respiratory or pulmonary administration. Other modes of administration include oral administration, suppositories, and active or passive transdermal delivery techniques.

The compositions described herein can be administered to a subject (e.g., a human patient that has or is at risk of developing VVC or RVVC) in an amount that is compatible with the dosage formulation and that will be prophylactically and/or therapeutically effective. An appropriate effective amount will fall in a relatively broad range but can be readily determined by one of skill in the art by routine trials. The "Physician's Desk Reference" and "Goodman and Gilman's The Pharmacological Basis of Therapeutics" are useful for the purpose of determining the amount needed. An adequate dose of the active antifungal drugs described herein may vary depending on such factors as preparation method, administration method, age and body weight of the patient, severity of symptoms, administration time, administration route, rate of excretion, and responsivity. An adequate dose of the vaccines described herein may vary depending on the primary vaccination regimen, administration route, use of adjuvant as well as the age and immunocompetence of the patient. A physician of ordinary skill in the art will easily determine and diagnose the administration dose effective for treatment.

In the case of, for example, fluconazole, a typical dose is 150 mg given orally, but the dosage amount can optionally range from, e.g., 50-200 mg, and thus can be, for example, 50, 100, 150, or 200 mg, as determined to be appropriate by those of skill in the art. If an antifungal agent other than fluconazole is administered, the dosage of the antifungal may be one that is routinely given for that antifungal agent.

In the case of an Als3 polypeptide vaccine, a typical dose for a single-dose primary vaccination regimen is 300 μg given by intramuscular injection, but the dosage amount can optionally range from, e.g., 60-300 μg. In various examples, for a single-dose primary vaccination regimen the dosage amount is 100-300 μg, for example, 150-200 μg, 200-250 μg, or 250-300 μg. In additional examples for a multiple-dose primary vaccination regimen, the dosage amount is 5-60 μg, for example, 10-50 μg, 20-40 μg, or 30 μg. The Als3 polypeptide vaccine may be injected into the patient in a volume of 1.0 ml or less, such as 0.75 ml, 0.5 ml, or 0.25 ml (e.g., a dosage of 300 μg in 0.5 ml).

Compositions may be prepared into unit-dose or multiple-dose preparations by those skilled in the art using a pharmaceutically acceptable carrier and/or excipient according to a method known in the art.

Kits

The invention also includes kits that can be used to carry out the methods of the invention. Thus, kits of the invention can include one or more Als3 polypeptides (e.g., Als3-2, Als3-1, Als3 (18-324), and/or Als3 (Ser/Thr-rich sequence)), optionally in the form of a vaccine composition including an adjuvant, such as, for example, aluminum hydroxide). In some examples, the Als3 polypeptide (e.g., Als3-2, Als3-1, Als3 (18-324), and/or Als3 (Ser/Thr-rich sequence)) is present in a container (e.g., a glass vial) in liquid form (e.g., in water or a buffered salt solution, such as, 10 mM sodium phosphate, pH 6.5 or 7.0, and 154 mM sodium chloride; see above for other examples of buffer and salt conditions that can be used). In other examples, the Als3 polypeptide (e.g., Als3-2, Als3-1, Als3 (18-324), and/or Als3 (Ser/Thr-rich sequence)) is present in a container (e.g., a glass vial) in lyophilized form. In such examples, the kit may optionally also include a diluent (e.g., water or a buffered salt solution) for reconstitution of the lyophilized polypeptide into liquid form prior to administration. The polypeptide may also be present in another formulation, as described herein, or as is known to be acceptable in the art. The amount of polypeptide and, optionally, adjuvant present in the compositions of the present kits can be, for example, as described above. Thus, for example, the kits can include an Als3 polypeptide (e.g., Als3-2, Als3-1, Als3 (18-324), and/or Als3 (Ser/Thr-rich sequence)) in an amount to facilitate the administration of a dose as described herein.

In addition to the Als3 polypeptide(s), the kits of the invention include one or more antifungal agents (e.g., fluconazole, ketoconazole, butoconazole, miconazole, terconazole, tioconazole, clotrimazole, and nystatin, or any of the other antifungal agents described above). In the case of, for example, fluconazole, the kits can include one or more doses in an amount as described herein, formulated in a tablet for oral administration (e.g., the fluconazole may be present in table form at a dosage of 50, 100, or 200 mg; the tablet may also include the following inactive ingredients: microcrystalline cellulose, dibasic calcium phosphate anhydrous, povidone, croscarmellose sodium, and magnesium stearate). The kit may include a single dose of the antifungal agent (e.g., fluconazole), or 2, 3, 4, 5, 6, 7, 8, 9, or 10 doses (e.g., at least 3 doses) of the antifungal agent (e.g., fluconazole). Other agents, such as butoconazole, miconazole, terconazole, tioconazole, and clotrimazole, can be present in the kits of the invention in the form of a cream, while clotrimazole, miconazole, and terconazole can be present in the form of a vaginal suppository, as is known in the art. These agents can be present in single or multiple doses. The antifungal agent may be packaged in a separate container within the kit so that a user (e.g., a physician) can provide the package containing the antifungal agent to a patient.

The kit components can be provided in dosage form to facilitate administration, and can optionally include materials required for administration and/or instructions for patient treatment consistent with, for example, the methods described herein.

For example, the kit can include instructions for use, which guides the user (e.g., the physician) with respect to the administration of the Als3 vaccine (e.g., at the point of care location). The kit can also include instructions guiding the physician to administer a first dose of an antifungal agent (e.g., fluconazole). These instructions, or a separate set of instructions, in the kit may guide a user (e.g., a patient) with respect to the administration of the antifungal agent, which may be separately packaged in the kit so that the antifungal agent can be given to the patient for later home administration. For example, the instructions may guide the user (e.g., the physician or patient) to administer a first dose of the antifungal agent immediately and to administer a second and subsequent doses of the antifungal agent every 12 hours, 24 hours, 36 hours, 48 hours, or 72 hours, or until the antifungal agent consumed.

For example, for uncomplicated VVC, in which the patient has experienced one or fewer episodes in a year, the symptoms are mild or moderate, and there are no significant host factors, such as poor immune function, the instructions may direct the user to take a 150 mg table by mouth as a single dose. For complicated VVC, in which the patient has experienced two or more episodes in a year, when severe symptoms of vulvovaginal inflammation are experienced, or when symptoms are coupled with pregnancy, poorly controlled diabetes, or poor immune function, the instruction may direct the user to take a 150 mg tablet by mouth every 72 hour for 3 doses or more. For recurrent VVC, in which the patient has experienced four or more episodes in a year, the instructions may direct the user to take a 150 mg tablet by mouth every third day until they have taken three doses total.

The kit may be packaged in materials suitable for storage in a refrigerator at a temperature of between 35° F. and 46° F. (2° C. and 8° C.). The desired average refrigerator vaccine storage temperature is ~40° F. (~5° C.). Exposure to temperatures outside these ranges may result in reduced vaccine potency and increased risk of vaccine-preventable diseases.

EXAMPLES

The following examples are intended to illustrate the invention. These are not meant to limit the invention in any way.

Example 1: Clinical Studies

Methods
Purpose

The purpose of the Phase 1b portion of this study was to compare the NDV-3A vaccine, the NDV-3 vaccine and the placebo head-to-head in the patient population of interest (women with RVVC) to evaluate safety and immunogenicity. The study size for comparing safety and immunogenicity (N=15 per group) is based on the dose comparison design used in NDV3-001 (Schmidt et al. (2012) *Vaccine* 30(52): 7594-7600).

The purpose of the Phase 2a portion of this study is to determine whether the NDV-3A vaccine decreases the recurrence rate of RVVC in female subjects 18-50 years of age compared to placebo. The study size for evaluating efficacy (N=86 per group) is based on a 50% attack rate over 6 months in the placebo group and a 50% vaccine efficacy.

Phase 1a Study Design

The Phase 1a study was a double-blind, placebo-controlled, ascending dose escalation study (30 and 300 μg) that enrolled healthy adults at a single study site. Vaccinations occurred on study day 0, with follow up evaluations on study days 3, 7, 14, 28, 90, and 180. A subset of vaccinees was re-consented to receive a second dose of vaccine on study day 180, with follow up visits 7, 14, and 90 days after the second dose. The lower participation rate in the group receiving the second dose (9 of 15 for the 30 μg dose, and 10 of 15 for the 300 μg dose) was documented as primarily due to the timing of the second dose and follow-up conflicting with mid-summer personal schedules.

Phase 1b/2a Study Design

The Phase 1b and 2a studies were multi-center, double-blind, randomized, placebo-controlled studies to evaluate the safety, tolerability, immunogenicity and efficacy in preventing vulvovaginal candidiasis in subjects with recurrent vulvovaginal candidiasis following administration of single dose of NDV-3A vaccine, NDV-3 vaccine, or placebo. In the Phase 2a portion of the study, to estimate the effect of a single dose of NDV-3A or placebo administered intramuscularly to patients (N=86 per group) diagnosed with recurrent vulvovaginal candidiasis (RVVC) on the safety and tolerability during the 12-months post vaccination period in the NDV-3A vaccine group and the placebo group; the humoral and cellular immune responses at pre-defined time points over a 12-month period in the NDV-3A vaccine group and the placebo group; and the clinical efficacy of NDV-3A in lowering the recurrence rate of VVC in RVVC subjects relative to placebo.

Vaginal cultures for *C. albicans* were obtained at enrollment and at pre-defined time points during the study, concomitant with collection of clinical signs and symptoms of VVC.

An additional subset of subjects was included to compare the humoral and cellular immune response of the NDV-3A vaccine group, NDV-3 vaccine group, and placebo group. The study size for comparing safety and immunogenicity (N=15 per group) was based on the dose comparison design used in NDV3-001.

Inclusion and Exclusion Criteria

Subjects were informed of the nature of the study and have agreed to and are able to read, review, and sign the informed consent document prior to screening. Female subjects had to be 18-50 years of age, inclusive, at the time of vaccination on an acceptable form of birth control. Subjects had to have a current episode of VVC (at Screening/Day −14) that can be confirmed with acute signs and symptoms of VVC (Composite Questionnaire score ≥3), a positive KOH smear, a positive vaginal mycological culture for *C. albicans*. Subjects had to have a history of 2 or more documented episodes of VVC in the 12 months prior to screening, including at least one of the previous episodes confirmed by positive results from a diagnostic lab test specific for the presence of *Candida* (e.g., DNA/Affirm, PCR, mycological culture.) Additional episodes may be self-reported. Subjects were administered 3 doses of oral fluconazole (150 mg dose given orally 3 days apart during the screening period on Days −14, −11, and −8) and were screened for response to the antifungal, as evidenced by a Composite Questionnaire score of <3 on Day 0. Subjects were required to show no clinically significant abnormalities on Papanicolaou (Pap) smear at study entry or a normal Pap test result from the previous 12 months as judged and documented by the investigator(s). During the study period, subjects were readministered 3 doses of oral fluconazole (150 mg dose given orally 3 days apart) if the subjects experienced a recurrence of VVC.

In general, subjects must be in good health as judged and documented by the investigator(s) in the medical history, physical examination (including but may not be limited to an evaluation of the cardiovascular, gastrointestinal, psychiatric, respiratory and central nervous systems), vital sign assessments, clinical laboratory assessments, and by general observations.

Subjects were ineligible if they reported receiving any systemic or topical vaginal antifungal therapy for four weeks prior to vaccination, other than the oral fluconazole provided by the site during the subject's participation in the study. Subjects were ineligible if mycological results from within 4 weeks prior to vaccination showed other yeast species (e.g. *C. glabrata, C. tropicalis*, etc.) as the cause of vaginitis. Subjects were ineligible if they had any other active infectious causes of vulvovaginitis (e.g., bacterial vaginosis, *Trichomonas vaginalis, Chlamydia trachomatis, Neisseria* gonorrhea, symptomatic HSV-1, symptomatic HSV-2, or symptomatic human papilloma virus) at screening or other vaginal or vulvar conditions that would confound the interpretation of clinical response as judged by the investigator. Subjects were ineligible if they would be under treatment or surgery at the start of the study for cervical intraepithelial neoplasia (CIN) or cervical carcinoma. Subjects were ineligible if they had any presence or history of a clinically significant disorder involving the cardiovascular, respiratory, renal, gastrointestinal, immunologic, hematologic, endocrine, or neurologic system(s), diagnosed diabetes mellitus (controlled or not) or psychiatric disease that would confound the interpretation of clinical response as judged by the investigator. Subjects were ineligible if they had a history of allergic response(s) or other serious reactions to nickel, aluminum, or yeast products or any contraindications to fluconazole. Subjects were ineligible if they had a history of clinically significant allergies including food or drug allergies, anaphylaxis (or other serious reaction) to vaccines. Subjects were ineligible if they had a known history of or active infection with hepatitis B, hepatitis C, or human immunodeficiency virus (HIV). Subjects were ineligible if they had received or were planning to receive any investigational drug, investigational vaccine, or investigational device within 4 weeks prior to vaccination, and at any other time during their participation in the study. Subjects were ineligible if they had received or were planning to receive any other live vaccine within 3 weeks prior to vaccination. Subjects were ineligible if they had or showed evidence of a recent history of drug or alcohol abuse. Subjects were ineligible if they reported the use or planned use of any immunosuppressive drugs, including systemic or topical vaginal corticosteroids, within 4 weeks prior to vaccination, with the exception of topical steroids (e.g., OTC hydrocortisone) used elsewhere on the body. Subjects were ineligible if they reported the use planned use of any medications or treatments that may alter immune responses to the study vaccine within 3 weeks prior to vaccination (e.g., cyclosporine, tacrolimus, cytotoxic drugs, immune globulin, *Bacillus* Calmette-Guerin (BCG), monoclonal antibodies, radiation therapy). Subjects were ineligible if they received any blood products within 3 months prior to vaccination and throughout the study. Subjects were ineligible if they reported donating blood/plasma within 4 weeks prior to vaccination. Subjects were ineligible if they were pregnant or intending to become pregnant over the course of the study, if they were breastfeeding, or had any other medical and/or social (e.g., non-compliant) reason which, in the opinion of the investigator, would prevent participation in the study. Subjects were ineligible if they were unable to commit to the follow-up visits and or have unreliable access to a telephone for follow-up contacts, either by self-admission (self-reporting) or in the opinion of the investigator.

Documentation of episodes of VVC prior to vaccination must meet the conditions specified in the inclusion criteria. In addition to a positive vaginal mycological culture for *C. albicans*, examples of diagnostic lab tests specific for the presence of *Candida* include, but are limited to, Affirm™ (BD), NuSwab® (LabCorp), SureSwab® (Qwest).

Vaccine and Adjuvants

The active component of the NDV-3 vaccine is a recombinant version of the N-terminal region (416 amino acids) of the *C. albicans* agglutinin-like sequence 3 protein (Als3p) with the addition of a six-His tag and linker sequences (Spellberg et al. (2006) *J Infect. Dis.* 194(2):256-60). Als3p was produced by batch fermentation of a *Saccharomyces cerevisiae* expression cell line at 100 L scale, harvested by centrifugation and purified using two chromatography columns (nickel-affinity and hydrophobic interaction resins) followed by concentration, diafiltration into phosphate-buffered saline (PBS), pH 7, and filtration. The purified Als3p bulk drug substance was intact, monomeric, and 99% pure by SDS-PAGE with Coomassie staining and was formulated with aluminum hydroxide at 1.0 mg Al/mL in PBS, pH 7. Two final container vaccine clinical lots were used for this study; lot 0939 (60 µg Als3p/mL) and lot 0940 (600 µg Als3p/mL). Clinical lots were stored at 2-8° C. post manufacture and monitored for stability. Manufacture of the bulk drug substance and final container lots using cGMPs was conducted by Althea Technologies (San Diego, Calif.). NDV-3 vaccine (0.5 mL dose containing 300 µg Als3-1 (SEQ ID NO: 3) formulated with aluminum hydroxide (0.5 mg Al) in isotonic PBS. NDV-3A vaccine (0.5 mL dose containing 300 µg Als3-2 (SEQ ID NO: 2) formulated with aluminum hydroxide (0.5 mg Al) in isotonic phosphate-buffered saline (PBS). Subjects were given a 0.5 mL intramuscular (IM) injection of either the study vaccine NDV-3A, study vaccine NDV-3 or a placebo containing aluminum hydroxide (0.5 mg Al) in isotonic PBS.

Immunogenicity Analysis

Blood samples were obtained from subjects on the specified days post vaccination. Plasma and PBMCs were isolated using standardized procedures. Plasma samples were evaluated for anti-Als3 total IgG and for anti-Als3 IgA1 by standardized ELISA methodology. Results are expressed in units of dilution$^{-1}$. PBMCs were evaluated by ELISpot analysis to determine the portion of cells that could be stimulated to produce IFN-γ or IL-17A (two separate assays). Results are expressed in units of spot forming units (SFU) per $10^6$ cells.

Statistical Analyses

Statistical analysis of assay results used non-parametric analysis using the Wilcoxon rank-sum test (Mann et al. (1947) *Ann. Math. Stat.* 18:50-60). Evaluation of trends across groups used the Kruskal-Wallis test (Cuzick (1985) *Stat. Med.* 4:87-90).

Results

Safety

In this study population, NDV-3 was safe and generally well-tolerated after one or two doses. Local injection site reactions to placebo (post dose 1) and vaccine and (post dose 1 and 2) are summarized in Table 1.

TABLE 1

Systemic and injection site AEs reported Days 0-7 post-vaccination regardless of causality.

| MedDRA Preferred Term | Placebo Dose 1 (N = 10) | 30 μg Dose Dose 1 (N = 15) | 30 μg Dose Dose2 (N = 9[a]) | 300 μg Dose Dose 1 (N = 15) | 300 μg Dose Dose 2 (N = 10[a]) |
|---|---|---|---|---|---|
| Injection site | | | | | |
| Erythema | 10% | 20%[b] | 11%[d] | 0 | 10%[b] |
| Induration | 10% | 0 | 0 | 0 | 20%[b] |
| Pain | 20% | 73%[b] | 100% | 73%[c] | 100%[b] |
| Swelling | 0 | 7% | 22%[d] | 7% | 30%[b] |
| Systemic AEs | | | | | |
| Diarrhea | 0 | 7% | 11% | 7% | 0 |
| Nausea | 0 | 13% | 0 | 0 | 30% |
| Fatigue | 10% | 7% | 11% | 7% | 40% |
| Myalgia | 0 | 0 | 11% | 20% | 20% |
| Extremity pain | 0 | 0 | 0 | 13% | 10%[b] |
| Headache | 10%[b] | 7% | 22% | 7%[b] | 30% |

[a]Subjects volunteered to continue in study to receive a 2nd dose.
[b]One graded as "moderate."
[c]Three graded as "moderate."
[d]One graded as "severe." All AEs resolved without sequelae.

The systemic and injection site AEs occurring in at least two study subjects after either the first or the second dose are presented in Table 1. The most common complaint was injection site pain, typically mild, lasting 1-2 days after vaccination and resolving within 2-3 days without sequelae. After dose 1 each of the systemic AEs shown in Table 1 were reflected in ≥2 of the 40 subjects. After dose 2, the most common systemic AEs were fatigue and headache (5 out of 19 (26%) subjects for each). Systemic AEs were usually mild and occasionally moderate, but all resolved without sequelae within a few days. There were no notable differences in systemic AEs between the two dose levels.

Immune Response

Plasma Anti-Als3p Total IgG and IgA1.

Prior to vaccination (day 0), 36 of the 40 subjects exhibited a detectable pre-existing anti-Als3p total IgG titer ranging from 114 to 2608 dilution$^{-1}$, with 4 subjects showing IgG titers below the limit of detection (LOD) of the assay (<50 dilution$^{-1}$). For IgA1 titers, 36 of the 40 subjects exhibited pre-existing detectable anti-Als3p IgA1 titer ranging from 102 to 6473 dilution$^{-1}$, with 4 subjects showing IgA1 titers below the LOD (<50 dilution$^{-1}$). Two subjects had no detectable anti-Als3p IgG or IgA1 prior to vaccination.

Figure 1A:
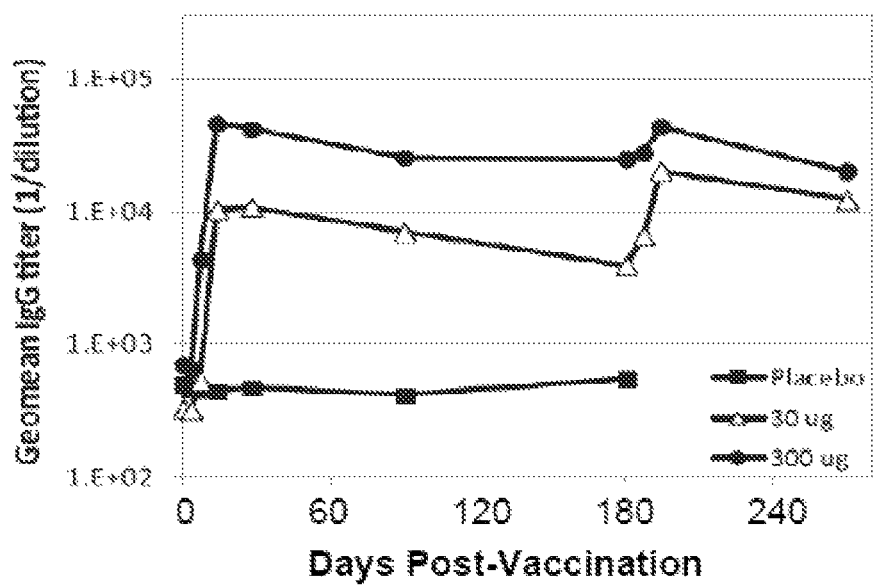
FIGS. 1A and 1B are graphs showing plasma anti-Als3 antibody titers through Day 270 post vaccination.
Figure 1B:
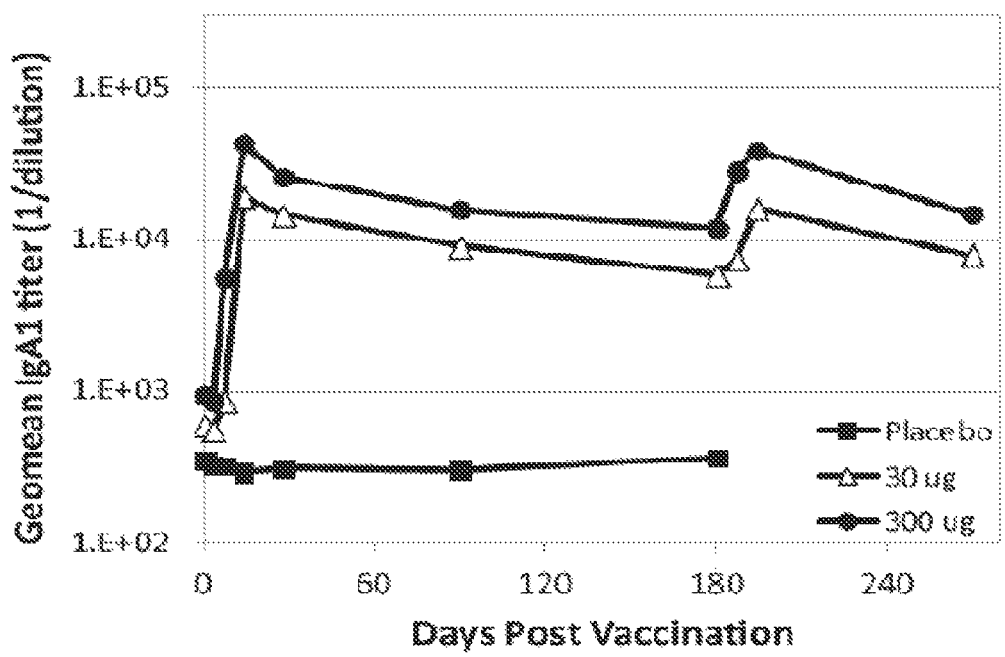

The geometric mean of anti-Als3p total IgG titers (FIG. 1A) and IgA1 titers (FIG. 1B) rose quickly after the first dose of vaccine, showing a substantial rise by day 7 post vaccination and reaching a maximum by day 14 post vaccination. The IgG and IgA1 titers from day 7 on were significantly higher for the 300 μg dose relative to the 30 μg dose (Mann-Whitney test, p<0.05) and both were beyond the range of placebo recipient titers (Mann-Whitney test, p<0.001). Antibody titers out to 180 days post vaccination showed roughly a two-fold decline from the maximum titers.

Following the second dose of vaccine, marked increases in anti-Als3p total IgG and IgA1 were noted, with the increase in the geomean IgG titer of the 30 g recipients being greater than that of the 300 μg recipients.

Figure 2A:
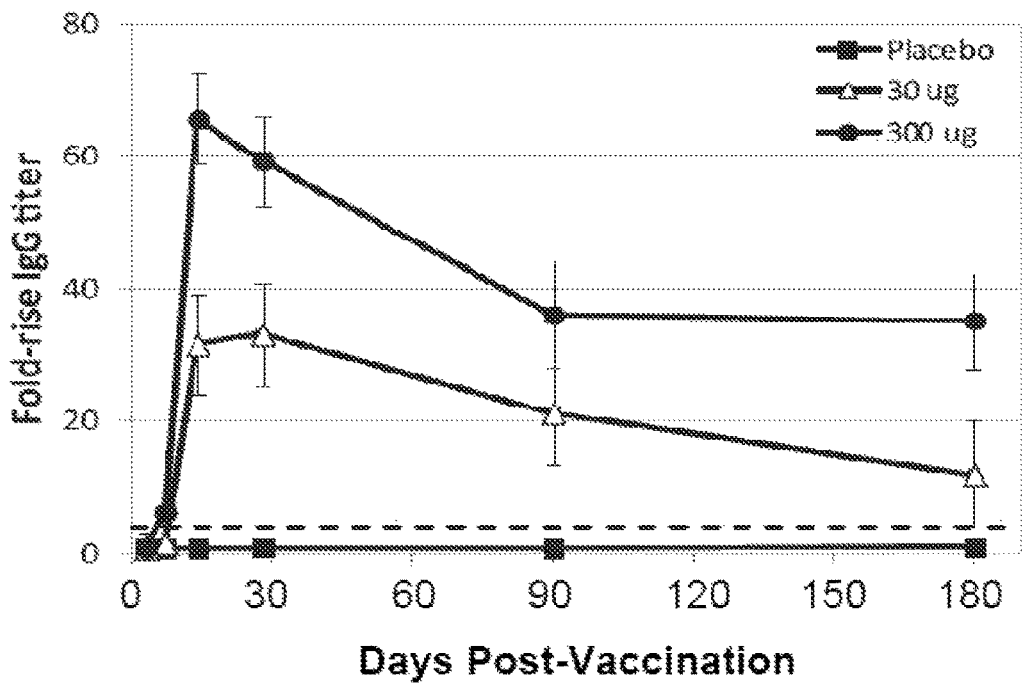
FIGS. 2A and 2B are graphs showing fold-rise increases in plasma anti-Alsip antibody titers through Day 180 post vaccination.
Figure 2B:
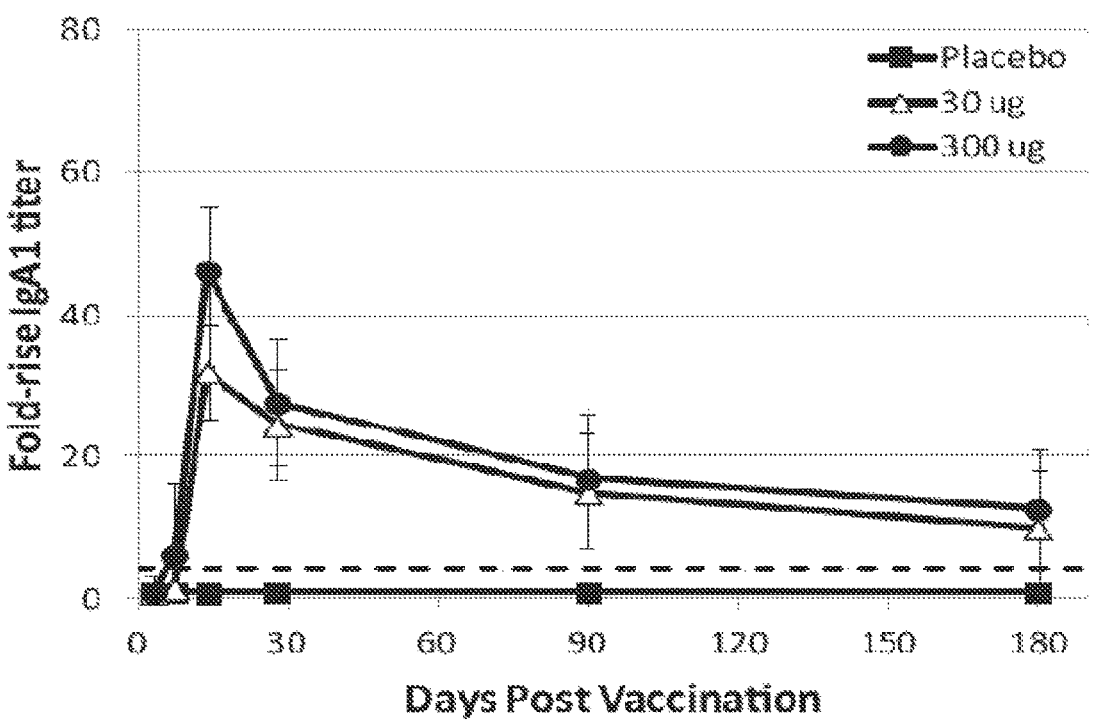

The fold-rise of anti-Als3p total IgG titers (FIG. 2A) and IgA1 titers (FIG. 2B) above the pre-vaccination titers all peaked at 14 days post vaccination. The fold-rise for IgG from day 7 to 180 was significantly higher for the 300 μg dose relative to the 30 μg dose (Mann-Whitney test, p<0.05) and for both dose levels the mean fold-rise remained >7-fold above pre-vaccination titers through day 180 post vaccination. Based on a definition of seroconversion being a ≥4-fold rise in antibody titer relative to the pre-vaccination antibody titer, a single dose of NDV-3 resulted in 13% and 53% of subjects seroconverting in IgG by day 7 (30 and 300 μg dose, respectively) and 100% seroconverting by day 14 in both dose groups (see Table 2). Similar results were observed for IgA1 seroconversion. For the 300 μg dose group, seroconversion remained at 100% for IgG through day 180, although for IgA1 there was a decline from 100% after day 28. For the 30 μg dose group, the seroconversion rate for IgG declined from 100% after day 28, while IgA1 seroconversion rates declined from 100% after day 14 (Table 2).

TABLE 2

Fold rise of anti-Als3 antibody titer relative to pre-vaccination (Day 0) titers.

| Dose (μg) | Ig type | % of subjects with >4-fold rise in anti-Als3 antibody titer | | | |
|---|---|---|---|---|---|
| | | Day 7 | Day 14 | Day 28 | Day 90 | Day 120 |
| 30 | IgG | 13 | 100 | 100 | 93 | 73 |
| 300 | IgG | 53 | 100 | 100 | 100 | 100 |
| 30 | IgA1 | 7 | 100 | 93 | 87 | 87 |
| 300 | IgA1 | 60 | 100 | 100 | 87 | 80 |

When study subjects were given a second dose of vaccine identical to their first, the increase in antibody titer after 14 days was relatively modest for those receiving the 300 μg dose, with increases in the GMT for IgG and IgA1 of 1.8- and 2.0-fold. For those receiving the 30 μg dose the GMT of IgG titers after 14 days increased 4.1-fold and the GMT for IgA1 increased 2.4-fold. At either dose level, the kinetics of the decrease in IgG and IgA1 titers appears to resume about the same rate as seen after the first dose (FIG. 1).

Anti-Als3 IFN-γ and IL-17A Production by Stimulated PBMCs.

Figure 3A:
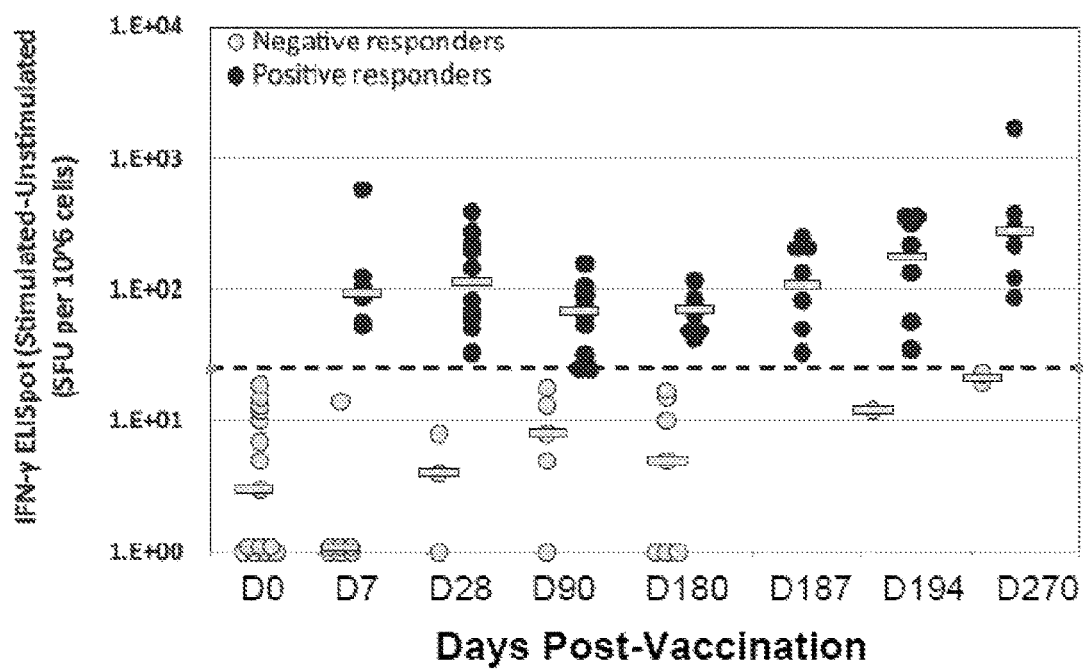
FIGS. 3A and 3B are graphs showing Als3-stimulated cytokine production by PBMCs for all subjects receiving the 30 µg dose through Day 270 post vaccination.
Figure 3B:
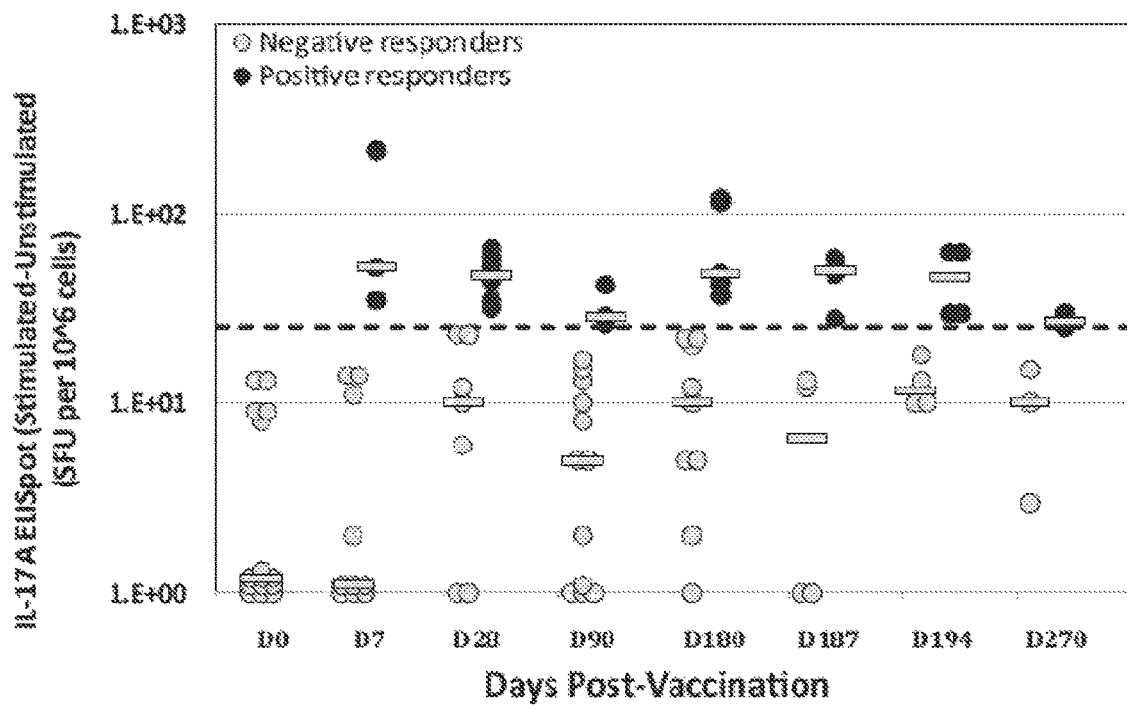

FIGS. 3A and 3B provide an overview of the IFN-γ (FIG. 3A) and IL-17A (FIG. 3B) ELISpot results for subjects receiving the 30 μg dose of vaccine. Subjects at each time point were segregated into "non-responders" and "responders," depending on whether or not their result exceeded the empirical cutoff of 25 SFU per $10^6$ cells. For both IFN-γ and IL-17A, the maximum response was seen on day 28 post vaccination. The mean responses (SFU per $10^6$ cells) for responders in each assay were similar on days 7 to 180, with a significantly greater number of cells producing IFN-γ than IL-17A.

Figure 4A:
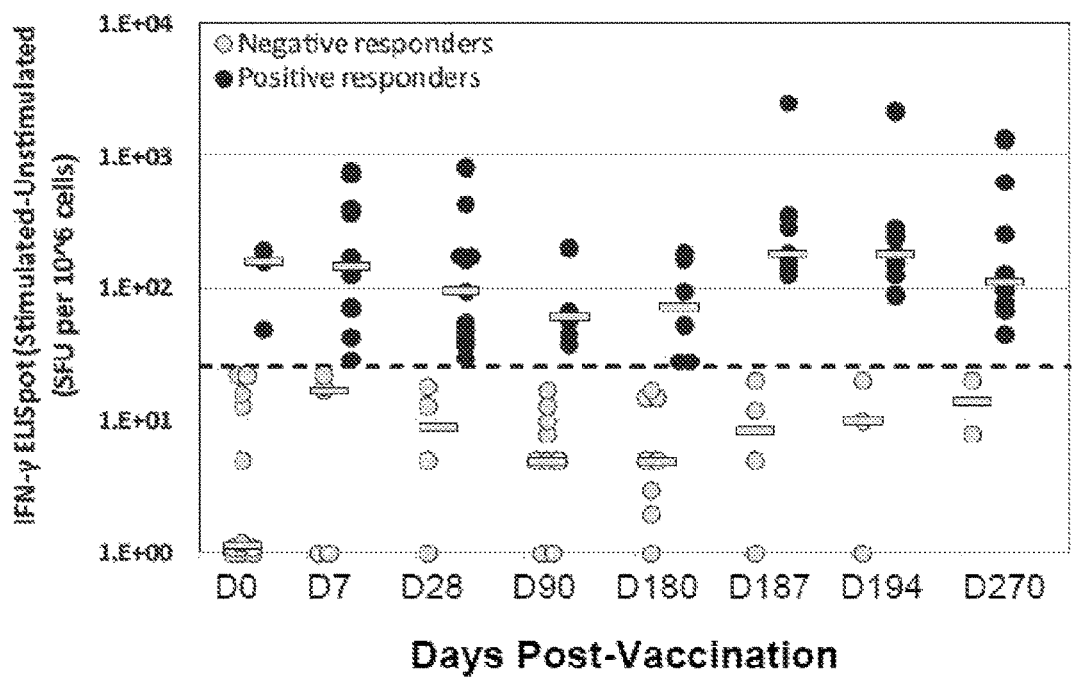
FIGS. 4A and 4B are graphs showing Als3-stimulated cytokine production by PBMCs for all subjects receiving the 300 µg dose through Day 270 post vaccination.
Figure 4B:
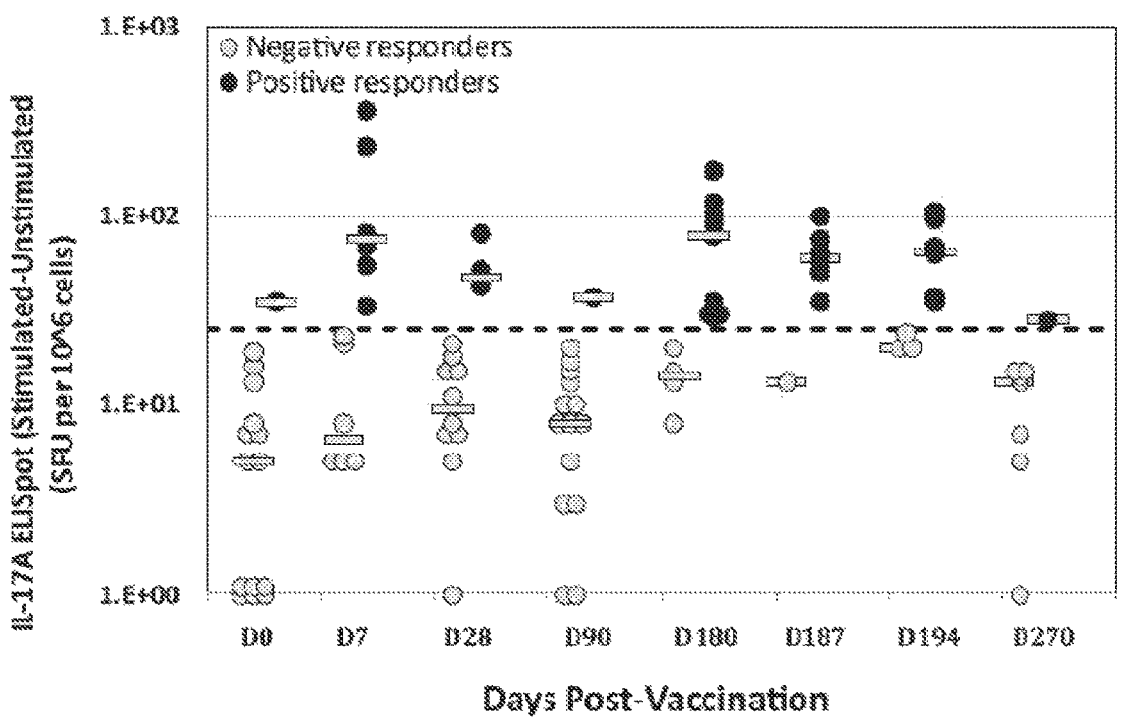

FIGS. 4A and 4B provide an overview of the IFN-γ and IL-17A ELISpot results, respectively, for subjects receiving the 300 μg dose of vaccine. In this case subjects receiving 300 μg of Als3p responded more rapidly than those receiving 30 μg Als3p, i.e., by day 7, and with a greater number of cells producing both cytokines. However, the drop off of response appeared to be more rapid, with a diminished response at day 90 post vaccination for both cytokines. Again, the IFN-γ producing cells far outnumbered the IL-17A cells in the responders at all time points.

Figure 5A:
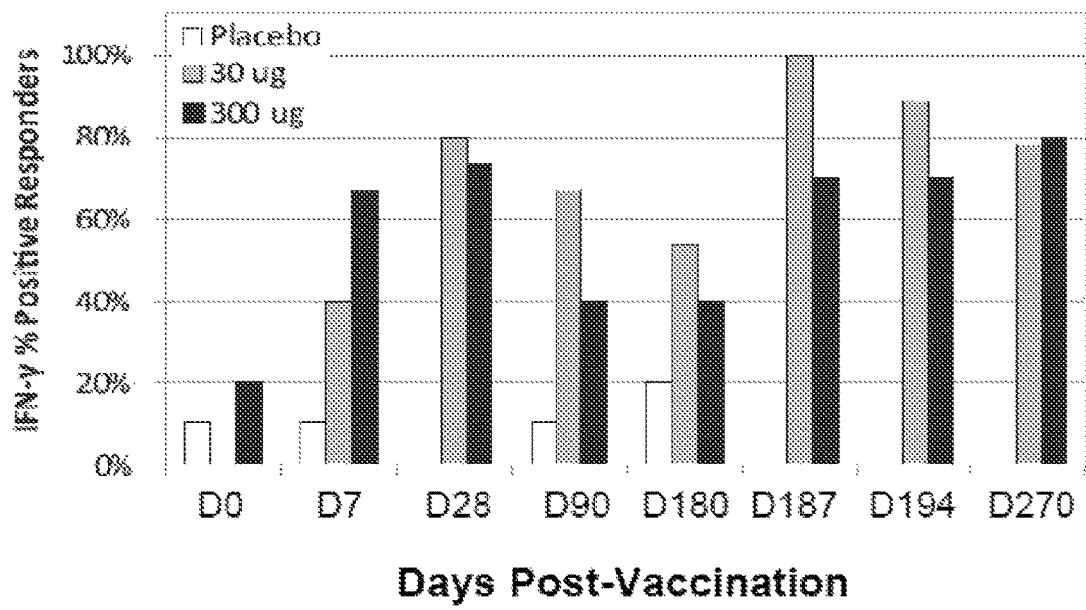
FIGS. 5A and 5B are graphs showing percentage of subjects responding with cytokine-producing PMBCs through Day 270 post vaccination.
Figure 5B:
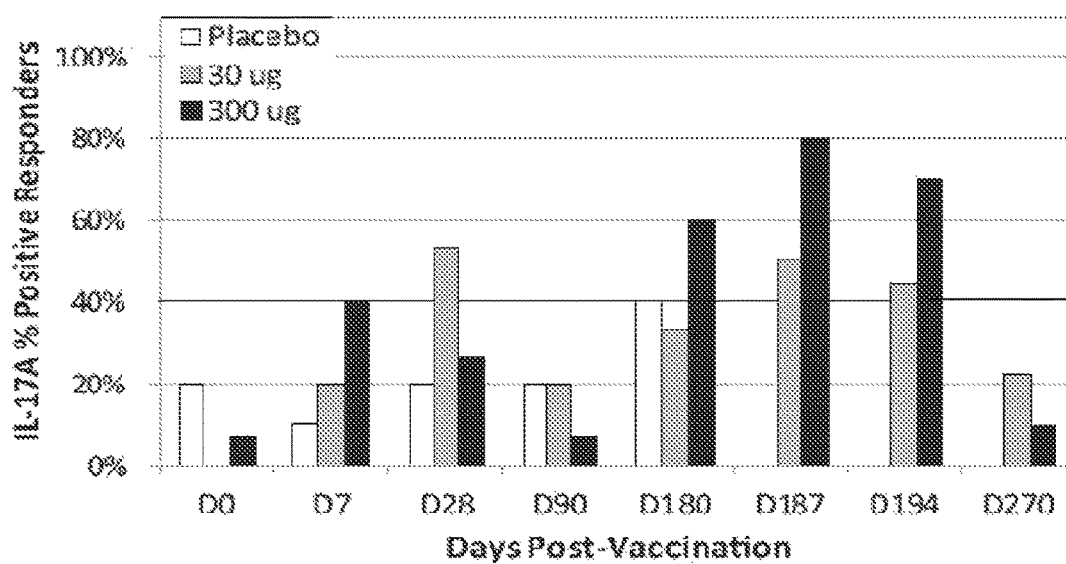

FIGS. 5A and 5B present IFN-γ and IL-17A ELISpot data, respectively, as the percent of positive responders for each group, including placebo recipients, at each time point. While this presentation reinforces the observations described above, it also makes clear that the IFN-γ response was more robust than the IL-17A response, with a greater percent of subjects responded at each time point and a greater difference from the placebo response. There was a more rapid rise in the percentage of both IFN-γ and IL-17A responders in the 300 μg dose group versus the 30 μg dose group on day 7 post-vaccination. However, by day 28 the 30 μg dose group showed slightly higher response rates than seen in the 300 g dose group. Furthermore, administration of the second dose at day 180 markedly increased the percentage of responders, with the IFN-γ response elevated most by the 30 μg dose and the IL-17A response elevated most by the 300 μg dose.

Figure 6A:
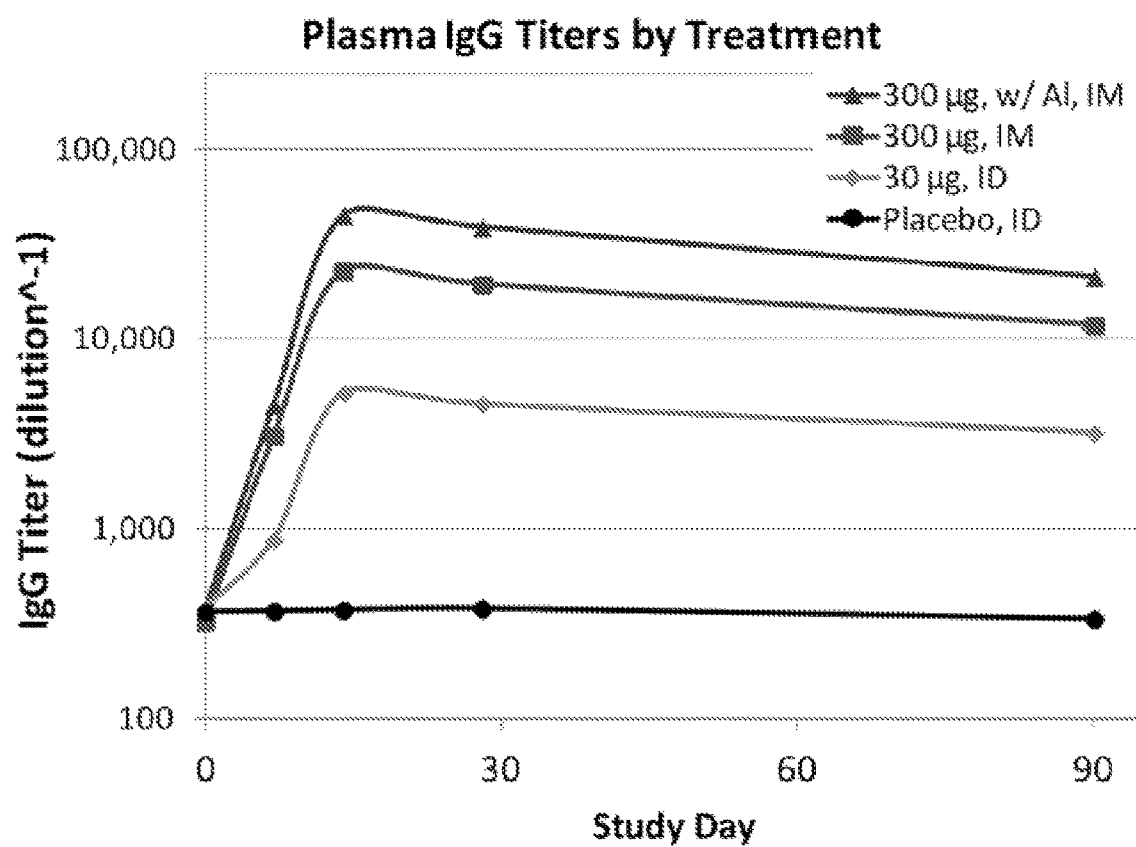
FIGS. 6A-6D are graphs showing anti-Als3 antibody levels in serum (FIG. 6A and FIG. 6C) and vaginal wash (FIGS. 6B and 6D).
Figure 6B:
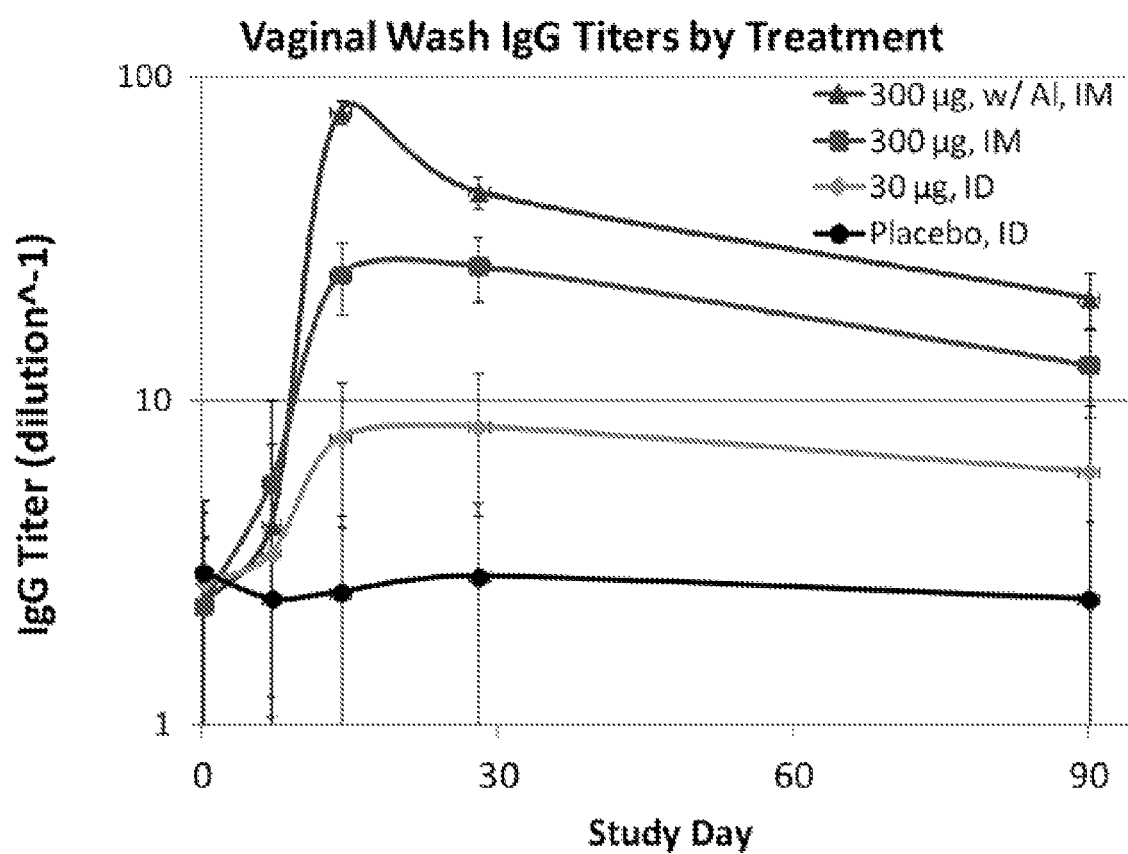
Figure 6C:
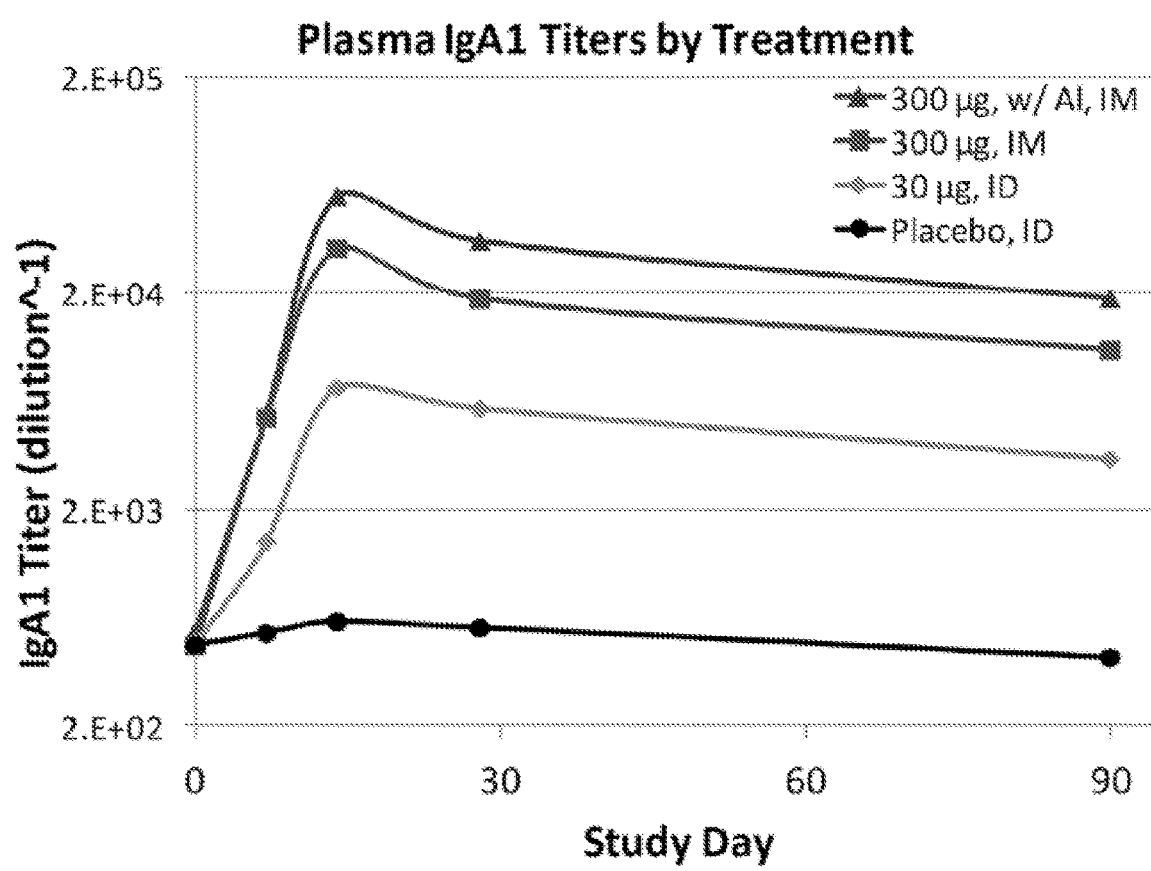
Figure 6D:
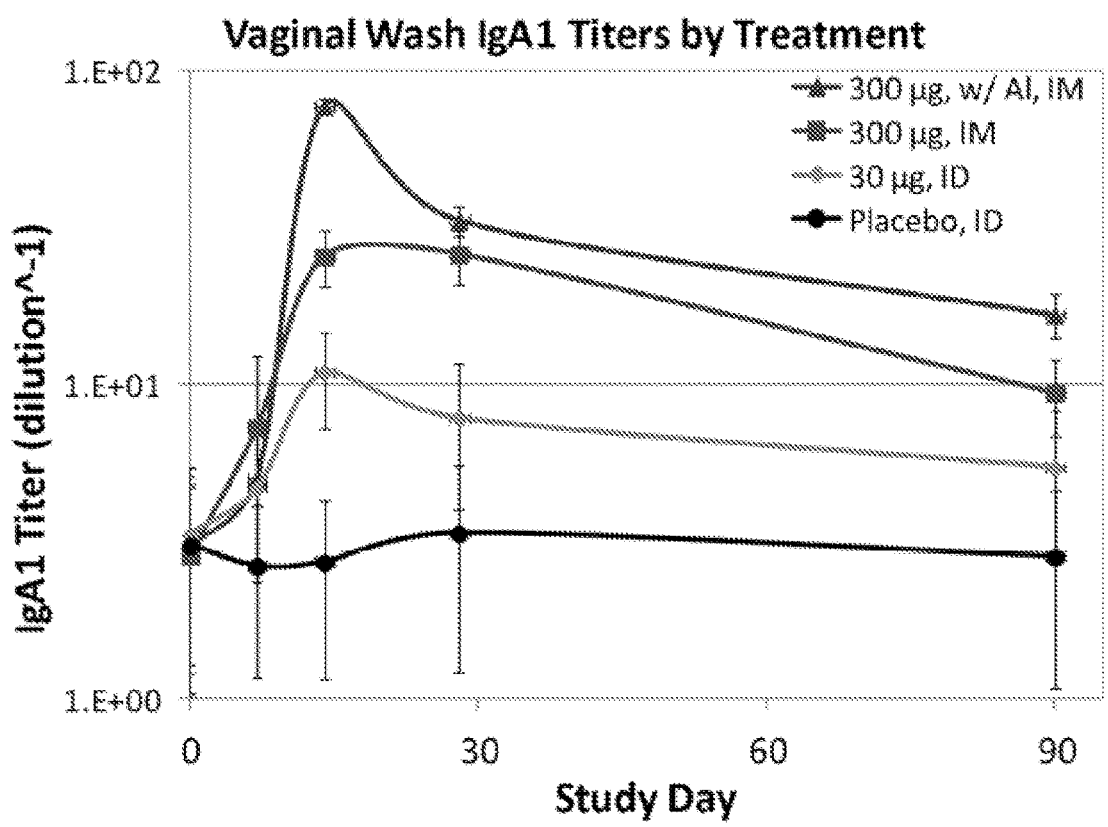

FIGS. 6A and 6B show the anti-Als3 IgG antibody levels in serum (FIG. 6A) and vaginal wash (FIG. 6B). FIGS. 6C and 6D show the anti-Als3 IgA1 antibody levels in serum (FIG. 6A) and vaginal wash (FIG. 6B). Responses were similar between IgG and IgA1. The 300 μg with alum has 2-3 fold higher antibody responses than the same dose without alum, whereas the 30 μg dose administered intradermally showed a similar antibody response to the same dose delivered intramuscularly (with alum). The 300 μg dose with AlOH induced significantly higher titers that the 300 μg dose without AlOH (Wilcoxon Rank Sum, p<0.001). The vaginal wash IgG and IgA1 titers correlated with the serum titers. Additionally, the mucosal antibody levels detected in vaginal washes reflect a very similar profile to that seen in plasma.

FIGS. 7A and 7B show the functional activity of the anti-Als3 antibodies, as assessed by a *C. albicans* opsonophagocytic killing (OPK) activity assay. OPK activity correlated with anti-Als3 IgG and IgA1 antibody titers, indicating that the vaccine-induces anti-Als3 antibodies directed an immune response against *C. albicans*.

FIGS. 8A and 8B show Th1 (FIG. 7A) and Th17 (FIG. 7B) T-cell stimulation by the Als3 antigen. The percent of subjects at Day 7 responding to the 300 μg dose give IM, with or without AlOH in the formulation, were significantly higher than that seen for the 30 μg Als3 dose given ID. By Day 14 or Day 90, the response to all doses and regimens reached similar levels for IFN-γ response. For the IL-17A response, the 300 μg dose groups are at a maximum at Day 7 and appear to decline at Day 14 and 90. It appears that the 30 μg dose given ID may have a low but more persistent activity for both cytokines.

FIG. 9 is a graph comparing post-vaccination sera (light gray bars) to pre-vaccination sera (dark gray bars, normalized to 100%) of each individual administered the Als3 antigen. Three separate assays were performed:

Adherence and Invasion Assays:

Live *Candida albicans* is mixed with vaccinee sera and then incubated with human endothelial cells. In the presence of post-vaccination sera, the cell-associated (adhered) and endocytosed (invaded) *Candida* was reduced to 59% and 54%, respectively, of the pre-vaccination levels of adherence and invasion, (p<0.05 for post-versus pre-).

Cell Damage Assay:

This assay measured the cell damage to human epithelial cells by *Candida*, again comparing levels of protection by post- and pre-vaccination sera. The cell damage in the presence of post-vaccination sera was about 52% of that with pre-vaccination sera (p<0.05 for post-versus pre-).

The blockage of adhesion and invasion of the vaginal mucosa is believed to be particularly important for preventing symptoms of vaginitis in patients with recurrent VVC. Anti-Als3 antibodies also exhibit the ability to target neutrophils to specifically recognize and engulf (phagocytize) *Candida*, as assessed using an opsonophagocytic killing (OPK) assay, an in vitro assay measuring the ability of sera from Phase 1 subjects post-vaccination to direct neutrophils to kill *Candida*. These data demonstrate that the anti-Als3 antibodies made in response to the NDV-3 vaccine were not only present in high amounts, but were also functionally active against *Candida* in vitro.

FIG. 10 shows the geometric mean functional OPK activity (line) in post-vaccination subjects in each treatment group compared to the geomean concentration of anti-Als3 antibodies measured by ELISA among the three treatment groups in the Phase 1 (bars). The correlation between the antibody concentration and OPK activity demonstrates that anti-Als3 antibodies made in response to the NDV-3 vaccine were functionally active in directing neutrophils to kill *Candida* in vitro. These data demonstrate that the anti-Als3 antibodies made in response to the NDV-3 vaccine were not only present in high amounts, but were also functionally active against *Candida* in vitro.

A Phase 1b study was carried out to estimate the effect of a single dose of NDV-3A, NDV-3 or placebo administered intramuscularly to patients (N=15 per group) diagnosed with recurrent vulvovaginal candidiasis (RVVC) on the following parameters. First, the safety and tolerability during the 12-months post vaccination period in the NDV-3A vaccine group, the NDV-3 vaccine group, and the placebo group were assessed. FIGS. 12A-12D show the antibody response results for comparison of the NDV-3 vaccine with the NDV-3A vaccine. FIGS. 11A and 11B show the difference between the NDV-3 vaccine and the NDV-3A vaccine in induction of anti-Als3 IgG antibody levels in serum (FIG. 11A) and vaginal wash (FIG. 11B). FIGS. 11C and 11D show the difference between the NDV-3 vaccine and the NDV-3A vaccine in induction of anti-Als3 IgA antibody levels in serum (FIG. 11C) and vaginal wash (FIG. 11D). Responses were similar between IgG and IgA1.

The humoral and cellular immune responses at predefined time points over a 12-month period in the NDV-3A vaccine group, the NDV-3 vaccine group, and the placebo group were also assessed. FIGS. 13A-13B show the Th1

(FIG. 12A) and Th17 (FIG. 12B) T-cell stimulation by the Als3 antigen. The results show a comparison between the NDV-3 vaccine and the NDV-3A vaccine. The percent of subjects at Day 14 showing an IFN-γ response to the NDV-3 vaccine was about 20% higher than the percent of subjects treated with the NDV-3A vaccine. Both groups retained a high (about 60%) IFN-γ response rate at Day 90. The percent of subjects showing an IL-17A response was lower for both treatment cohorts, with the NDV-3A patients showing a slightly (about 10%) enhanced response at Day 90.

FIG. 13 is a graph comparing the anti-Als3 IgG antibody titers in sera from the Phase 2a study with RVVC with healthy volunteers of the Phase 1a study. There are no remarkable differences between healthy volunteers and Phase 2a patients. Because RVVC patients tested positive for Candida albicans two weeks prior to vaccination (Day 0), the apparent lack of immune memory response to wild-type Candida infection is surprising. However, when recombinant Als3 is administered IM on alum, a memory response is triggered.

Recurrence Studies

Patients treated with NDV-3A were monitored for recurrence of RVVC and compared to that of placebo control patients. Time-to-first recurrence was monitored, as well as the cumulative number of recurrences at each time point. Recurrence was defined by several metrics and results were analyzed with respect to the corresponding recurrence definition. In some studies, recurrence was defined as the patient's observation of symptoms ("patient symptom score"). In other studies, recurrence was defined as the physician's observation of signs or symptoms of infection ("sign/symptom score"). In other studies, recurrence was defined as the physician's observation of signs or symptoms of infection in addition to a positive culture test ("signs+ symptoms & positive culture).

FIGS. 14A-14C are Kaplan-Meier curves showing the proportion of non-recurrence of RVVC over time in NDV-3A-treated patients versus placebo controls. In studies defining recurrence by sign/symptom score among patients of all ages (FIG. 14A), 30 out of 88 (34%) NDV-3A-treated patients experienced disease recurrence over the course of 97 days, while 38 out of 82 (46%) placebo patients experienced disease recurrence. The significance level of the difference between the Kaplan-Meier recurrence curves is 0.10 and vaccine efficacy was 33%.

In studies defining recurrence by patient symptom score among patients of all ages (FIG. 14B), 44 out of 88 (50%) NDV-3A-treated patients experienced disease recurrence over the course of 374 days, compared to 53 out of 82 (65%) placebo patients experiencing recurrence. The significance level of the difference between the Kaplan-Meier recurrence curves is 0.06 and vaccine efficacy was 31%. The lower significance value resulting from defining recurrence by patient symptom score indicates a greater statistical confidence in the results and, more broadly, indicates that the patient symptom score is a more accurate readout in comparison to the signs/symptoms score.

In studies defining recurrence by patient symptom score among patients under the age of 40 (FIG. 14C), 32 out of 68 (47%) NDV-3A-treated patients experienced disease recurrence over the course of 374 days, compared to 40 out of 63 (63%) placebo patients experiencing recurrence. The significance level of the difference between the Kaplan-Meier recurrence curves is 0.02 and vaccine efficacy was 42%. These data show a markedly improved vaccine response in patients under the age of 40. Specifically, NDV-3A increases the time-to-first recurrence ($p<0.05$) and that the proportion of patients that remain recurrence free out to 12 months ("cure rate") increases from about 30% in the placebo group to about 50% in the NDV-3A group. Placebo recipients are 2.5-times more likely to experience a recurrence within 3 months than the placebo group ($p<0.05$). The odds ratios for first recurrence measured by each scoring metric at the 3-month visit are shown in Table 3, and the odds ratios for first recurrence measured by patient symptom score for each patient cohort at each time point are shown in Table 4, below.

TABLE 3

Odds ratios for first recurrence at 3-month visit.

| | Number of subjects included | Signs + symptoms >2 & positive culture | Signs + symptoms >2 | Symptoms >2 |
| --- | --- | --- | --- | --- |
| All subjects | 170 | 0.90 (0.47, 1.75) | 0.60 (0.32, 1.11) | 0.54 (0.29, 1.01) |
| Subjects <40 years old | 139 | 0.60 (0.42, 1.91) | 0.53 (0.26, 1.07) | 0.43 (0.21, 0.88) |
| Subjects ≥40 years old | 31 | 0.93 (0.24, 3.62) | 0.92 (0.25, 3.42) | 1.14 (0.31, 4.16) |

TABLE 4

Odds ratios for first recurrence measured by patient symptom score.

| Age group by visit | Odds ratio for first recurrence (vaccine/placebo) | 95% confidence interval |
| --- | --- | --- |
| At 3-month visit | | |
| All subjects under 40 years of age | 0.43 | (0.21, 0.88) |
| All subjects 40 years or older | 1.14 | (0.31, 4.16) |
| All subjects | 0.54 | (0.29, 1.01) |
| At 6-month visit | | |
| All subjects under 40 years of age | 0.63 | (0.32, 1.26) |
| All subjects 40 years or older | 1.67 | (0.46, 6.05) |
| All subjects | 0.79 | (0.43, 1.44) |
| At 12-month visit | | |
| All subjects under 40 years of age | 0.54 | (0.27, 1.09) |
| All subjects 40 years or older | 0.86 | (0.23, 3.26) |
| All subjects | 0.60 | (0.32, 1.11) |

FIGS. 15A-15D are cumulative recurrence graphs showing the mean cumulative number of recurrent episodes in NDV-3A-treated patients versus placebo controls. In studies defining recurrence by sign/symptom score among patients of all ages (FIG. 15A), NDV-3A-treated patients experienced fewer cumulative recurrences compared to placebo controls at a significance level of 0.15. In studies defining recurrence by sign/symptom score among patients under 40 years of age (FIG. 15B), NDV-3A-treated patients experienced fewer cumulative recurrences compared to placebo controls at a significance level of 0.02. These results reflect the non-recurrence trends between NDV-3A-treated patients and placebo controls. Specifically, lower significance levels of the under 40-years old cohort relative to all ages indicates that patients under 40 are more likely to experience fewer cumulative recurrences as a result of the vaccine when recurrence is measured by signs/symptom score.

In studies defining recurrence by patient symptom score among patients of all ages (FIG. 15C), NDV-3A-treated patients experienced fewer cumulative recurrences compared to placebo controls at a significance level of 0.20. In studies defining recurrence by sign/symptom score among patients under 40 years of age (FIG. 15D), NDV-3A-treated patients experienced fewer cumulative recurrences compared to placebo controls at a significance level of 0.03. The mean number of recurrences per patient over a 12-month period was reduced by about 30% in response to NDV-3A treatment.

The onset of RVVC occurs mainly in subjects less than 40 years of age. In a study conducted on our behalf, we determined that, at the first age of onset of RVVC, about 90% of the subjects (n=127) were less than 40 years old. The studies presented herein clearly show that patients under the age of 40 years are more responsive to NDV-3A treatment in terms of time-to-first recurrence and number of cumulative recurrences. To determine whether this difference corresponded with a difference in antibody response to the vaccine between the two age cohorts, antibody titers were quantified over time and compared. FIG. 16 is a graph showing the results of the titer comparison. Vaccine recipients under the age of 40 years did not show a significantly higher titer response than vaccine recipients over the age of 40 years.

Example 2: Use of a Kit to Treat Vulvovaginal Candidiasis

A female patient presenting with symptoms including one or more of heavy white curd-like vaginal discharge, a burning sensation in the vagina and vulva and/or an itchy rash on the vulva and surrounding skin can be diagnosed at a point of care location (e.g., a physician's office or a hospital) as having vulvovaginal candidiasis (VVC). The physician can retrieve a kit that includes instructions for use and two containers: a) a container containing an Als3 polypeptide (e.g., Als3-2, Als3-1, Als3 (18-324), and/or Als3 (Ser/Thr-rich sequence)), e.g., in the form of a vaccine composition including an adjuvant, such as, for example, aluminum hydroxide (e.g., the Als3p vaccine may be formulated at a dose of 600 μg/ml), and b) a container containing an antifungal agent (e.g., fluconazole, e.g., in the form of a tablet for oral administration and at a dose of, e.g., 50, 100, 150, or 200 mg per tablet). The physician can retrieve a first dose of the anti-fungal agent (e.g., fluconazole) from the kit and administer it to the patient or instruct the patient to self-administer the first dose as soon as possible. Subsequently, or prior to administration of the anti-fungal agent, the physician can administer a volume (e.g., 0.5 ml) of the Als3 vaccine to the patient to provide a total dose of ~60-500 μg (e.g., 300 μg) of the vaccine. The kit allows the patient to begin the antifungal agent course of therapy immediately without having to visit a pharmacy to fill a prescription. This is more convenient for the patient and can lead to higher compliance since they receive the initial doses of antifungal agent and vaccine during the visit, as well as extra instructions from their healthcare provider for subsequent doses.

If the patient is diagnosed with uncomplicated VVC, the physician may send the patient home with instructions to monitor the condition for improvement and to seek additional medical care if symptoms do not improve within 1-3 days. If the patient is diagnosed with complicated VVC, the physician may provide the container containing the anti-fungal agent to the patient with instructions and an amount of the anti-fungal agent sufficient for the patient to take a 150 mg tablet by mouth every 72 hour for 3 doses or more. If the patient is diagnosed with recurrent VVC, the physician may provide the container containing the anti-fungal agent to the patient with instructions and an amount of the anti-fungal agent sufficient for the patient to take a 150 mg tablet by mouth every third day until they have taken three doses total. Additional doses may be included in the kit, if necessary, or the patient may be given a prescription that includes a refill.

OTHER EMBODIMENTS

All publications, patents, and patent applications mentioned in the above specification are hereby incorporated by reference. Various modifications and variations of the described methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

APPENDIX 1

| VVC Signs and Symptoms Questionnaire (example) VVC Signs and Symptoms Questionnaire | | | | |
|---|---|---|---|---|
| | Score*(circle one) | | | |
| Subject Symptom Evaluation (previous 24 hours) | | | | |
| Vaginal itching | 0 | 1 | 2 | 3 |
| Vaginal irritation | 0 | 1 | 2 | 3 |
| Vaginal burning | 0 | 1 | 2 | 3 |
| Investigator VVC Evaluation (on gynecological exam) | | | | |
| Vulvar or vaginal erythema | 0 | 1 | 2 | 3 |
| Vulvar or vaginal edema | 0 | 1 | 2 | 3 |
| Vulvar or vaginal excoriation/fissure formation | 0 | 1 | 2 | 3 |
| Total Composite Questionnaire Score (Subject and Investigator): | | | | |
| | (Sum of scores) | | | |

*Score Key: 0 = Absent, 1 = Mild, 2 = Moderate, 3 = Severe

Composite Questionnaire Score Key:

0-2 = not clinically indicative of VVC (asymptomatic)

3-6 = Mild Disease 7-12 = Moderate Disease

≥13 = Severe Disease

The invention claimed is:

1. A method comprising the steps of
   a) administering to a subject having vulvovaginal candidiasis (VVC) an antifungal agent; and
   b) administering an immunogenic amount of an Als3 polypeptide to said subject, to reduce VVC in said subject,
   wherein said Als3 polypeptide has at least 80% identity to any one of SEQ ID NOs: 1-5.

2. The method of claim 1, wherein:
   a) said immunogenic amount of said Als3 polypeptide is administered subsequent to administration of said antifungal agent;
   b) said antifungal agent is administered from 5 to 8 days after administration of said Als3 polypeptide; or
   c) said antifungal agent is administered from 13 to 15 days after administration of said Als3 polypeptide.

3. The method of claim 1, wherein said subject has recurrent VVC (RVVC).

4. The method of claim 1, wherein said antifungal agent is fluconazole.

5. The method of claim 4, wherein said fluconazole is administered in a dose of from 100 mg to 200 mg orally or a dose of 150 mg orally.

6. The method of claim 1, wherein a second dose of said antifungal agent is administered from 2 to 4 days after administration of said antifungal agent of step a) and, optionally, a third dose of said antifungal agent is administered from 2 to 4 days after administration of said second dose of said antifungal agent, or wherein said Als3 polypeptide is administered from 7 days to 21 days or 14 days after the administration of said antifungal agent of step a).

7. The method of claim 1, wherein from 5 to 300 micrograms of said Als3 polypeptide is administered.

8. The method of claim 7, wherein from 10 to 200 micrograms, from 20 to 100 micrograms, from 30 to 90 micrograms, from 40 to 80 micrograms, from 100 to 300 micrograms, from 150 to 200 micrograms, from 200 to 250 micrograms, from 250 to 300 micrograms, or 300 micrograms of said Als3 polypeptide is administered.

9. The method of claim 1, wherein one or more booster doses of said Als3 polypeptide is administered.

10. The method of claim 1, wherein said antifungal agent is administered from 5 to 8 days or from 13 to 15 days after administration of said Als3 polypeptide.

11. The method of claim 1, wherein said subject is less than 40 years old.

12. A kit comprising
    a) an antifungal agent; and
    b) an Als3 polypeptide, wherein said Als3 polypeptide has at least 80% identity to any one of SEQ ID NOs: 1-5.

13. The kit of claim 12, wherein:
    a) said antifungal agent is fluconazole; and
    b) said Als3 polypeptide is in a vaccine composition with or without an adjuvant.

14. A method of treating a subject with, or at risk of developing, recurrent VVC (RVVC), comprising administering to the subject at least 5.0 micrograms of an Als3 polypeptide to reduce recurrences of VVC in said subject, wherein said Als3 polypeptide has at least 80% identity to any one of SEQ ID NOs: 1-5.

15. The method of claim 14, wherein said subject has RVVC.

16. The method of claim 14, wherein the method comprises administering from 5 micrograms to 300 micrograms of the Als3 polypeptide.

17. The method of claim 14, wherein the subject has had at least one, two, or three prior VVC infection during the past 12 months.

18. The method of claim 14, wherein:
    said Als3 polypeptide is administered in a vaccine composition with or without an adjuvant.

19. The method of claim 14, wherein:
    a) said method further comprises administering one or more booster doses of said Als3 polypeptide;

b) said subject does not have a current diagnosis of VVC, or is not experiencing a current episode of VVC, at the time of said administering;
c) said subject does not have a VVC Sign and Symptom Composite Questionnaire Score of ≥3 at the time of said administering;
d) said subject has previously had a diagnosis of VVC or recurrent VVC; or
e) said subject is less than 40 years old.

20. The method of claim 1, wherein said Als3 polypeptide has the sequence of any one of SEQ ID Nos: 1-5.

21. The method of claim 1, wherein said Als3 polypeptide is administered as a vaccine composition with or without an adjuvant.

22. The method of claim 1, wherein said Als3 polypeptide is administered in either a single dose primary vaccination regimen or a multi-dose primary vaccination regimen.

23. The kit of claim 13, wherein said Als3 polypeptide has the sequence of any one of SEQ ID NOs: 1-5.

24. The method of claim 18, wherein said Als3 polypeptide has the sequence of any one of SEQ ID NOs: 1-5.

\* \* \* \* \*

SEQUENCE LISTING

<160> NUMBER OF SEQ ID NOS: 6

<210> SEQ ID NO 1
<211> LENGTH: 1119
<212> TYPE: PRT
<213> ORGANISM: Candida albicans

<400> SEQUENCE: 1

```
Met Leu Gln Gln Tyr Thr Leu Leu Ile Tyr Leu Ser Val Ala Thr
1               5                   10                  15

Ala Lys Thr Ile Thr Gly Val Phe Asn Ser Phe Asn Ser Leu Thr Trp
                20                  25                  30

Ser Asn Ala Ala Thr Tyr Asn Tyr Lys Gly Pro Gly Thr Pro Thr Trp
                35                  40                  45

Asn Ala Val Leu Gly Trp Ser Leu Asp Gly Thr Ser Ala Ser Pro Gly
        50                  55                  60

Asp Thr Phe Thr Leu Asn Met Pro Cys Val Lys Phe Thr Thr Ser
65                  70                  75                  80

Gln Thr Ser Val Asp Leu Thr Ala His Gly Val Lys Tyr Ala Thr Cys
                85                  90                  95

Gln Phe Gln Ala Gly Glu Glu Phe Met Thr Phe Ser Thr Leu Thr Cys
                100                 105                 110

Thr Val Ser Asn Thr Leu Thr Pro Ser Ile Lys Ala Leu Gly Thr Val
                115                 120                 125

Thr Leu Pro Leu Ala Phe Asn Val Gly Gly Thr Gly Ser Ser Val Asp
        130                 135                 140

Leu Glu Asp Ser Lys Cys Phe Thr Ala Gly Thr Asn Thr Val Thr Phe
145                 150                 155                 160

Asn Asp Gly Gly Lys Lys Ile Ser Ile Asn Val Asp Phe Glu Arg Ser
                165                 170                 175

Asn Val Asp Pro Lys Gly Tyr Leu Thr Asp Ser Arg Val Ile Pro Ser
                180                 185                 190

Leu Asn Lys Val Ser Thr Leu Phe Val Ala Pro Gln Cys Ala Asn Gly
                195                 200                 205

Tyr Thr Ser Gly Thr Met Gly Phe Ala Asn Thr Tyr Gly Asp Val Gln
        210                 215                 220

Ile Asp Cys Ser Asn Ile His Val Gly Ile Thr Lys Gly Leu Asn Asp
225                 230                 235                 240

Trp Asn Tyr Pro Val Ser Ser Glu Ser Phe Ser Tyr Thr Lys Thr Cys
                245                 250                 255

Ser Ser Asn Gly Ile Phe Ile Thr Tyr Lys Asn Val Pro Ala Gly Tyr
                260                 265                 270

Arg Pro Phe Val Asp Ala Tyr Ile Ser Ala Thr Asp Val Asn Ser Tyr
                275                 280                 285

Thr Leu Ser Tyr Ala Asn Glu Tyr Thr Cys Ala Gly Gly Tyr Trp Gln
        290                 295                 300

Arg Ala Pro Phe Thr Leu Arg Trp Thr Gly Tyr Arg Asn Ser Asp Ala
305                 310                 315                 320

Gly Ser Asn Gly Ile Val Ile Ala Thr Thr Arg Thr Val Thr Asp
                325                 330                 335

Ser Thr Thr Ala Val Thr Thr Leu Pro Phe Asp Pro Asn Arg Asp Lys
                340                 345                 350

Thr Lys Thr Ile Glu Ile Leu Lys Pro Ile Pro Thr Thr Ile Thr
                355                 360                 365
```

```
Thr Ser Tyr Val Gly Val Thr Thr Ser Tyr Ser Thr Lys Thr Ala Pro
        370                 375                 380
Ile Gly Glu Thr Ala Thr Val Ile Val Asp Ile Pro Tyr His Thr Thr
385                 390                 395                 400
Thr Thr Val Thr Ser Lys Trp Thr Gly Thr Ile Thr Ser Thr Thr Thr
                405                 410                 415
His Thr Asn Pro Thr Asp Ser Ile Asp Thr Val Ile Val Gln Val Pro
                420                 425                 430
Ser Pro Asn Pro Thr Val Thr Thr Glu Tyr Trp Ser Gln Ser Phe
            435                 440                 445
Ala Thr Thr Thr Ile Thr Gly Pro Pro Gly Asn Thr Asp Thr Val
450                 455                 460
Leu Ile Arg Glu Pro Pro Asn His Thr Val Thr Thr Glu Tyr Trp
465                 470                 475                 480
Ser Glu Ser Tyr Thr Thr Thr Ser Thr Phe Thr Ala Pro Pro Gly Gly
                485                 490                 495
Thr Asp Ser Val Ile Ile Lys Glu Pro Pro Asn Pro Thr Val Thr Thr
                500                 505                 510
Thr Glu Tyr Trp Ser Glu Ser Tyr Thr Thr Thr Ser Thr Phe Thr Ala
                515                 520                 525
Pro Pro Gly Gly Thr Asp Ser Val Ile Ile Lys Glu Pro Pro Asn His
530                 535                 540
Thr Val Thr Thr Thr Glu Tyr Trp Ser Gln Ser Tyr Thr Thr Thr Thr
545                 550                 555                 560
Thr Val Thr Ala Pro Pro Gly Gly Thr Asp Thr Val Leu Val Arg Glu
                565                 570                 575
Pro Pro Asn His Thr Val Thr Thr Thr Glu Tyr Trp Ser Gln Ser Tyr
                580                 585                 590
Thr Thr Thr Thr Thr Val Ile Ala Pro Pro Gly Gly Thr Asp Ser Val
                595                 600                 605
Ile Ile Arg Glu Pro Pro Asn Pro Thr Val Thr Thr Glu Tyr Trp
610                 615                 620
Ser Gln Ser Tyr Ala Thr Thr Thr Ile Thr Ala Pro Pro Gly Glu
625                 630                 635                 640
Thr Asp Thr Val Leu Ile Arg Glu Pro Pro Asn His Thr Val Thr Thr
                645                 650                 655
Thr Glu Tyr Trp Ser Gln Ser Tyr Ala Thr Thr Thr Ile Thr Ala
                660                 665                 670
Pro Pro Gly Glu Thr Asp Thr Val Leu Ile Arg Glu Pro Pro Asn His
                675                 680                 685
Thr Val Thr Thr Thr Glu Tyr Trp Ser Gln Ser Phe Ala Thr Thr Thr
690                 695                 700
Thr Val Thr Ala Pro Pro Gly Gly Thr Asp Thr Val Ile Ile Arg Glu
705                 710                 715                 720
Pro Pro Asn His Thr Val Thr Thr Thr Glu Tyr Trp Ser Gln Ser Tyr
                725                 730                 735
Ala Thr Thr Thr Thr Ile Thr Ala Pro Pro Gly Glu Thr Asp Thr Val
                740                 745                 750
Leu Ile Arg Glu Pro Pro Asn His Thr Val Thr Thr Glu Tyr Trp
            755                 760                 765
Ser Gln Ser Tyr Ala Thr Thr Thr Thr Ile Ile Ala Pro Pro Gly Glu
770                 775                 780
Thr Asp Thr Val Leu Ile Arg Glu Pro Pro Asn Pro Thr Val Thr Thr
```

```
                785                 790                 795                 800
Thr Glu Tyr Trp Ser Gln Ser Tyr Thr Thr Ala Thr Thr Val Thr Ala
                    805                 810                 815
Pro Pro Gly Gly Thr Asp Thr Val Ile Ile Tyr Asp Thr Met Ser Ser
                820                 825                 830
Ser Glu Ile Ser Ser Phe Ser Arg Pro His Tyr Thr Asn His Thr Thr
                835                 840                 845
Leu Trp Ser Thr Thr Trp Val Ile Glu Thr Lys Thr Ile Thr Glu Thr
                850                 855                 860
Ser Cys Glu Gly Asp Lys Gly Cys Ser Trp Val Ser Val Ser Thr Arg
865                 870                 875                 880
Ile Val Thr Ile Pro Asn Asn Ile Glu Thr Pro Met Val Thr Asn Thr
                    885                 890                 895
Val Asp Ser Thr Thr Thr Glu Ser Thr Ser Gln Ser Pro Ser Gly Ile
                900                 905                 910
Phe Ser Glu Ser Gly Val Ser Val Glu Thr Glu Ser Thr Val Thr
                915                 920                 925
Thr Ala Gln Thr Asn Pro Ser Val Pro Thr Thr Glu Ser Glu Val Val
                930                 935                 940
Phe Thr Thr Lys Gly Asn Asn Glu Asn Gly Pro Tyr Glu Ser Pro Ser
945                 950                 955                 960
Thr Asn Val Lys Ser Ser Met Asp Glu Asn Ser Glu Phe Thr Thr Ser
                    965                 970                 975
Thr Ala Ala Ser Thr Ser Thr Asp Ile Glu Asn Glu Thr Ile Ala Thr
                980                 985                 990
Thr Gly Ser Val Glu Ala Ser Ser Pro Ile Ile Ser Ser Ser Ala Asp
                995                 1000                1005
Glu Thr Thr Thr Val Thr Thr Thr Ala Glu Ser Thr Ser Val Ile
                1010                1015                1020
Glu Gln Pro Thr Asn Asn Asn Gly Gly Gly Lys Ala Pro Ser Ala
                1025                1030                1035
Thr Ser Ser Pro Ser Thr Thr Thr Thr Ala Asn Asn Asp Ser Val
                1040                1045                1050
Ile Thr Gly Thr Thr Ser Thr Asn Gln Ser Gln Ser Gln Ser Gln
                1055                1060                1065
Tyr Asn Ser Asp Thr Gln Gln Thr Thr Leu Ser Gln Gln Met Thr
                1070                1075                1080
Ser Ser Leu Val Ser Leu His Met Leu Thr Thr Phe Asp Gly Ser
                1085                1090                1095
Gly Ser Val Ile Gln His Ser Thr Trp Leu Cys Gly Leu Ile Thr
                1100                1105                1110
Leu Leu Ser Leu Phe Ile
                1115

<210> SEQ ID NO 2
<211> LENGTH: 416
<212> TYPE: PRT
<213> ORGANISM: Candida albicans

<400> SEQUENCE: 2

Lys Thr Ile Thr Gly Val Phe Asn Ser Phe Asn Ser Leu Thr Trp Ser
1               5                   10                  15
Asn Ala Thr Tyr Asn Tyr Lys Gly Pro Gly Thr Pro Thr Trp Asn
                20                  25                  30
```

```
Ala Val Leu Gly Trp Ser Leu Asp Gly Thr Ser Ala Ser Pro Gly Asp
         35                  40                  45

Thr Phe Thr Leu Asn Met Pro Cys Val Phe Lys Phe Thr Thr Ser Gln
 50                  55                  60

Thr Ser Val Asp Leu Thr Ala His Gly Val Lys Tyr Ala Thr Cys Gln
 65                  70                  75                  80

Phe Gln Ala Gly Glu Glu Phe Met Thr Phe Ser Thr Leu Thr Cys Thr
                 85                  90                  95

Val Ser Asn Thr Leu Thr Pro Ser Ile Lys Ala Leu Gly Thr Val Thr
                100                 105                 110

Leu Pro Leu Ala Phe Asn Val Gly Thr Gly Ser Ser Val Asp Leu
            115                 120                 125

Glu Asp Ser Lys Cys Phe Thr Ala Gly Thr Asn Thr Val Thr Phe Asn
130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
    290                 295                 300

Ser Asn Gly Ile Val Ile Val Ala Thr Thr Arg Thr Val Thr Asp Ser
305                 310                 315                 320

Thr Thr Ala Val Thr Thr Leu Pro Phe Asp Pro Asn Arg Asp Lys Thr
                325                 330                 335

Lys Thr Ile Glu Ile Leu Lys Pro Ile Pro Thr Thr Ile Thr Thr
            340                 345                 350

Ser Tyr Val Gly Val Thr Thr Ser Tyr Leu Thr Lys Thr Ala Pro Ile
        355                 360                 365

Gly Glu Thr Ala Thr Val Ile Val Asp Ile Pro Tyr His Thr Thr Thr
    370                 375                 380

Thr Val Thr Ser Lys Trp Thr Gly Thr Ile Thr Ser Thr Thr Thr His
385                 390                 395                 400

Thr Asn Pro Thr Asp Ser Ile Asp Thr Val Ile Val Gln Val Pro Leu
                405                 410                 415
```

<210> SEQ ID NO 3
<211> LENGTH: 425
<212> TYPE: PRT
<213> ORGANISM: Candida albicans

<400> SEQUENCE: 3

-continued

```
His His His His His His Gly Ile Gln Lys Thr Ile Thr Gly Val Phe
1               5                   10                  15

Asn Ser Phe Asn Ser Leu Thr Trp Ser Asn Ala Ala Thr Tyr Asn Tyr
                20                  25                  30

Lys Gly Pro Gly Thr Pro Thr Trp Asn Ala Val Leu Gly Trp Ser Leu
                35                  40                  45

Asp Gly Thr Ser Ala Ser Pro Gly Asp Thr Phe Thr Leu Asn Met Pro
        50                  55                  60

Cys Val Phe Lys Phe Thr Thr Ser Gln Thr Ser Val Asp Leu Thr Ala
65                  70                  75                  80

His Gly Val Lys Tyr Ala Thr Cys Gln Phe Gln Ala Gly Glu Glu Phe
                85                  90                  95

Met Thr Phe Ser Thr Leu Thr Cys Thr Val Ser Asn Thr Leu Thr Pro
                100                 105                 110

Ser Ile Lys Ala Leu Gly Thr Val Thr Leu Pro Leu Ala Phe Asn Val
        115                 120                 125

Gly Gly Thr Gly Ser Ser Val Asp Leu Glu Asp Ser Lys Cys Phe Thr
        130                 135                 140

Ala Gly Thr Asn Thr Val Thr Phe Asn Asp Gly Gly Lys Lys Ile Ser
145                 150                 155                 160

Ile Asn Val Asp Phe Glu Arg Ser Asn Val Asp Pro Lys Gly Tyr Leu
                165                 170                 175

Thr Asp Ser Arg Val Ile Pro Ser Leu Asn Lys Val Ser Thr Leu Phe
                180                 185                 190

Val Ala Pro Gln Cys Ala Asn Gly Tyr Thr Ser Gly Thr Met Gly Phe
                195                 200                 205

Ala Asn Thr Tyr Gly Asp Val Gln Ile Asp Cys Ser Asn Ile His Val
        210                 215                 220

Gly Ile Thr Lys Gly Leu Asn Asp Trp Asn Tyr Pro Val Ser Ser Glu
225                 230                 235                 240

Ser Phe Ser Tyr Thr Lys Thr Cys Ser Ser Asn Gly Ile Phe Ile Thr
                245                 250                 255

Tyr Lys Asn Val Pro Ala Gly Tyr Arg Pro Phe Val Asp Ala Tyr Ile
                260                 265                 270

Ser Ala Thr Asp Val Asn Ser Tyr Thr Leu Ser Tyr Ala Asn Glu Tyr
        275                 280                 285

Thr Cys Ala Gly Gly Tyr Trp Gln Arg Ala Pro Phe Thr Leu Arg Trp
        290                 295                 300

Thr Gly Tyr Arg Asn Ser Asp Ala Gly Ser Asn Gly Ile Val Ile Val
305                 310                 315                 320

Ala Thr Thr Arg Thr Val Thr Asp Ser Thr Ala Val Thr Thr Leu
                325                 330                 335

Pro Phe Asp Pro Asn Arg Asp Lys Thr Lys Thr Ile Glu Ile Leu Lys
                340                 345                 350

Pro Ile Pro Thr Thr Ile Thr Thr Ser Tyr Val Gly Val Thr Thr
        355                 360                 365

Ser Tyr Leu Thr Lys Thr Ala Pro Ile Gly Glu Thr Ala Thr Val Ile
        370                 375                 380

Val Asp Ile Pro Tyr His Thr Thr Thr Val Thr Ser Lys Trp Thr
385                 390                 395                 400

Gly Thr Ile Thr Ser Thr Thr Thr His Thr Asn Pro Thr Asp Ser Ile
                405                 410                 415
```

```
Asp Thr Val Ile Val Gln Val Pro Leu
        420                 425
```

<210> SEQ ID NO 4
<211> LENGTH: 303
<212> TYPE: PRT
<213> ORGANISM: Candida albicans

<400> SEQUENCE: 4

```
Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala
    290                 295                 300
```

<210> SEQ ID NO 5
<211> LENGTH: 108
<212> TYPE: PRT
<213> ORGANISM: Candida albicans

<400> SEQUENCE: 5

```
Ile Val Ile Val Ala Thr Thr Arg Thr Val Thr Asp Ser Thr Thr Ala
1               5                   10                  15
```

```
Val Thr Thr Leu Pro Phe Asp Pro Asn Arg Asp Lys Thr Lys Thr Ile
            20              25                  30
Glu Ile Leu Lys Pro Ile Pro Thr Thr Ile Thr Thr Ser Tyr Val
        35              40                  45
Gly Val Thr Thr Ser Tyr Ser Thr Lys Thr Ala Pro Ile Gly Glu Thr
    50              55                  60
Ala Thr Val Ile Val Asp Ile Pro Tyr His Thr Thr Thr Thr Val Thr
65                  70                  75                  80
Ser Lys Trp Thr Gly Thr Ile Thr Ser Thr Thr Thr His Thr Asn Pro
                85                  90                  95
Thr Asp Ser Ile Asp Thr Val Ile Val Gln Val Pro
                100                 105

<210> SEQ ID NO 6
<211> LENGTH: 17
<212> TYPE: PRT
<213> ORGANISM: Candida albicans

<400> SEQUENCE: 6

Met Leu Gln Gln Tyr Thr Leu Leu Leu Ile Tyr Leu Ser Val Ala Thr
1               5                   10                  15
Ala
```